US010927375B1

(12) United States Patent
Liggett

(10) Patent No.: US 10,927,375 B1
(45) Date of Patent: Feb. 23, 2021

(54) COMPOSITIONS AND METHODS TO REDUCE BETA-AGONIST-MEDIATED TACHYPHYLAXIS

(71) Applicant: Stephen B. Liggett, Tampa, FL (US)

(72) Inventor: Stephen B. Liggett, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/264,425

(22) Filed: Jan. 31, 2019

Related U.S. Application Data

(60) Provisional application No. 62/624,165, filed on Jan. 31, 2018.

(51) Int. Cl.

*A61K 48/00* (2006.01)
*C07H 21/04* (2006.01)
*C07H 21/02* (2006.01)
*C12N 15/113* (2010.01)
*A61K 45/06* (2006.01)
*A61K 31/7105* (2006.01)

(52) U.S. Cl.

CPC ........ *C12N 15/113* (2013.01); *A61K 31/7105* (2013.01); *A61K 45/06* (2013.01); *C12N 2310/14* (2013.01)

(58) Field of Classification Search

CPC ........................... A61K 31/713; C12N 15/113; C12N 2310/14; C12N 2320/30; C12N 2310/141; C12N 2310/11

See application file for complete search history.

(56) References Cited

PUBLICATIONS

Wang et al. (PNAS, 2011, vol. 108, No. 15, pp. 6246-6251).*
Lo et al. (Respiratory Research, 2017, 18, 194, pp. 1-9).*
Mellios et al. (PNAS, 2014, vol. 111, No. 27, 9947-9952).*
Liggett, Desensitization of the beta-adrenergic receptor: distinct molecular determinants of phosphorylation by specific kinases, Pharmacol. Res. 24 Suppl 1, 29-41, 1991.
Kohout et al., Regulation of G protein-coupled receptor kinases and arrestins during receptor desensitization. Mol. Pharmacol. 63, 9-18, 2002.
Lohse et al., What is the role of beta-adrenergic signaling in heart failure? Circ. Res. 93, 896-906, 2003.
Liggett, Phosphorylation barcoding as a mechanism of directing GPCR signaling. Sci Signal 4, p. 36, 2011.
Hanyaloglu et al., Regulation of GPCRs by endocytic membrane trafficking and its potential implications. Annu. Rev. Pharmacol. Toxicol. 48, 537-568, 2008.
Lefkowitz, Arrestins come of age: a personal historical perspective. Prog. Mol. Biol. Transl. Sci. 118, 3-18, 2013.
Lipworth, Airway subsensitivity with long-acting beta 2-agonists. Is there cause for concern? Drug Saf. 16, 295-308, 1997.
Newnham et al., Subsensitivity of bronchodilator and systemic b2 adrenoceptor responses after regular twice daily treatment with eformoterol dry power in asthmatic patients. Thorax 50, 497-504, 1995.
Kalra et al., Inhaled corticosteroids do not prevent the development of tolerance to the bronchoprotective effect of salmeterol. Chest 109, 953-956, 1996.
Harvey et al., Airway response to salbutamol: effect of regular salbutamol inhalations in normal, atopic, and asthmatic subjects. Thorax 37, 280-287, 1982.
Bhagat et al., Rapid Onset of Tolerance to the Bronchoprotective Effect of Salmeterol. Chest 108, 1235-1239, 1995.
Grove et al., Bronchodilator subsensitivity to salbutamol after twice daily salmeterol in asthmatic patients. Lancet 346, 201-206, 1995.
Booth et al., Salmeterol tachyphylaxis in steroid treated asthmatic subjects. Thorax 51, 1100-1104, 1996.
Israel et al., Use of regularly scheduled albuterol treatment in asthma: genotype-stratified, randomised, placebo-controlled cross-over trial. Lancet 364, 1505-1512, 2004.
Salpeter et al., Meta-Analysis: effect of long-acting b-agonists on severe asthma exacerbations and asthma-related deaths. Ann. Intern. Med. 144, 904-912, 2006.
Sears, Role of b-agonists in asthma fatalities. In Fatal Asthma (Sheffer, A. L., ed) vol. 115 pp. 457-481, Marcel Dekker, Inc., New York, 1998.
Nelson et al.,The Salmeterol Multicenter Asthma Research Trial: a comparison of usual pharmacotherapy for asthma or usual pharmacotherapy plus salmeterol. Chest 129, 15-26, 2006.
Grainger et al., Prescribed fenoterol and death from asthma in New Zealand, 1981-7: a further case-control study. Thorax 46, 105-111, 1991.
Wang et al., MicroRNA let-7 establishes expression of b2-adrenergic receptors and dynamically downregulates agonist-promoted downregulation. Proc. Natl. Acad. Sci. U. S. A. 108, 6246-6251, 2011.
Deshpande et al., Bitter taste receptors on airway smooth muscle bronchodilate by localized calcium signaling and reverse obstruction. Nat. Med. 16, 1299-1304, 2010.
Aisenberg et al., Defining an olfactory receptor function in airway smooth muscle cells. Sci. Rep. 6, 38231, 2016.
Kim et al., Coupling of Airway Smooth Muscle Bitter Taste Receptors to Intracellular Signaling and Relaxation Is via Galphai1,2,3. Am. J. Respir. Cell Mol. Biol. 56, 762-771, 2017.
Kim et al., beta2-Adrenergic Receptors Chaperone Trapped Bitter Taste Receptor 14 to the Cell Surface as a Heterodimer and Exert Unidirectional Desensitization of Taste Receptor Function. J. Biol. Chem. 291, 17616-17628, 2016.
Xue et al. MicroRNA-Let-7f reduces the vasculogenic mimicry of human glioma cells by regulating periostin-dependent migration. Oncol. Rep. 35, 1771-1777, 2016.
Barnes et al., BLIMP-1 and STAT3 counterregulate microRNA-21 during plasma cell differentiation. J. Immunol. 189, 253-260, 2012.
Panebra et al., Common ADRB2 haplotypes derived from 26 polymorphic sites direct b2-adrenergic receptor expression and regulation phenotypes. PLoS One 5, e11819, 2010.

(Continued)

*Primary Examiner* — Amy H Bowman
(74) *Attorney, Agent, or Firm* — Thomas|Horstemeyer LLP

(57) ABSTRACT

Described herein are let-7f miRNA inhibitors and uses thereof. In some embodiments, the let-7f miRNA inhibitors can be capable of reducing method of reducing β-agonist-mediated $\beta_2$-Adrenergic Receptor ($\beta_2$AR) down regulation in a subject in need thereof.

8 Claims, 9 Drawing Sheets

Specification includes a Sequence Listing.

(56) References Cited

PUBLICATIONS

Panebra et al., Variable length poly-C tract polymorphisms of the b2-adrenergic receptor 3'UTR alter expression and agonist regulation. Am. J. Physiol. Lung Cell Mol. Physiol. 294, L190-L195, 2008.

Schmittgen et al., Analyzing real-time PCR data by the comparative C(T) method. Nat. Protoc. 3, 1101-1108, 2008.

Livak et al., Analysis of relative gene expression data using real-time quantitative PCR and the 2(-Delta Delta C(T)) Method. Methods 25, 402-408, 2001.

Qiu et al., GATA transcription factors regulate the expression of the human eosinophil-derived neurotoxin (RNase 2) gene. J. Biol. Chem. 284, 13099-13109, 2009.

Mialet-Perez et al., b1-adrenergic receptor polymorphisms confer differential function and predisposition to heart failure. Nat. Med. 9, 1300-1305, 2003.

Sandelin et al., JASPAR: an open-access database for eukaryotic transcription factor binding profiles. Nucleic Acids Res. 32, D91-94, 2004.

An et al., An inflammation-independent contraction mechanophenotype of airway smooth muscle in asthma. J. Allergy Clin. Immunol. 138, 294-297.e294, 2016.

Liggett et al., Altered patterns of agonist-stimulated cAMP accumulation in cells expressing mutant b2-adrenergic receptors lacking phosphorylation sites. Mol. Pharmacol. 36, 641-646, 1989.

Campbell et al., Mutations of the human beta 2-adrenergic receptor that impair coupling to Gs interfere with receptor down-regulation but not sequestration. Mol. Pharmacol. 39, 192-198, 1991.

Swift et al., Pleiotropic b-agonist-promoted receptor conformations and signals independent of intrinsic activity. Am. J. Respir. Cell Mol. Biol. 36, 236-243, 2007.

Bouvier et al., Two distinct pathways for cAMP-mediated down-regulation of the b2-adrenergic receptor. J. Biol. Chem. 264, 16786-16792, 1989.

Han et al., The Drosha-DGCR8 complex in primary microRNA processing. Genes Dev. 18, 3016-3027, 2004.

Chendrimada et al., TRBP recruits the Dicer complex to Ago2 for microRNA processing and gene silencing. Nature 436, 740-744, 2005.

Moore et al., Agonist-induced sorting of human beta2-adrenergic receptors to lysosomes during downregulation. J. Cell Sci. 112 ( Pt 3), 329-338, 1999.

Mizuta et al., The dopamine D1 receptor is expressed and facilitates relaxation in airway smooth muscle. Respir. Res. 14, 89, 2013.

Liggett, Bitter taste receptors on airway smooth muscle as targets for novel bronchodilators. Expert Opin. Ther. Targets 17, 721-731, 2013.

McGraw et al., Targeted transgenic expression of b2-adrenergic receptors to type II cells increases alveolar fluid clearance. Am. J. Physiol. Lung Cell Mol. Physiol. 281, L895-L903, 2001.

Kim et al., A CREB-mediated increase in miRNA let-7f during prolonged beta-agonist exposure: a novel mechanism of beta2-adrenergic receptor down-regulation in airway smooth muscle, The FASEB Journal, vol. 32, p. 3680-3688, 2018.

Wang et al., MicroRNA let-7 establishes expression of β2-adrenergic receptors and dynamically down-regulates agonist-promoted down-regulation, PNAS, vol. 108, No. 15, 6246-6251, 2011.

Lo et al., Reduced suppressive effect of β2-adrenoceptor agonist on fibrocyte function in severe asthma, Respiratory Research (2017) 18:194.

Mellios et al., β2-Adrenergic receptor agonist ameliorates phenotypes and corrects microRNA-mediated IGF1 deficits in a mouse model of Rett syndrome, PNAS, vol. 111, No. 27, 9947-9952, 2014.

* cited by examiner

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: forward CREB binding site 1 sequencing primer

<400> SEQUENCE: 1

tgtgtgtttt gcacaccagt t                                              21


<210> SEQ ID NO 2
<211> LENGTH: 21
<212> TYPE: DNA
<213> ORGANISM: Artificial Sequence
<220> FEATURE:
<223> OTHER INFORMATION: reverse CREB binding site 1 sequencing primer

<400> SEQUENCE: 2

agacaattca actgggaatc g                                              21


<210> SEQ ID NO 3
<211> LENGTH: 25
<212> TYPE: DNA
<213> ORGANISM: Artificial Sequence
<220> FEATURE:
<223> OTHER INFORMATION: forward CREB binding site 2 sequencing primer

<400> SEQUENCE: 3

gctacctcct aaatatgaag tctgt                                          25


<210> SEQ ID NO 4
<211> LENGTH: 21
<212> TYPE: DNA
<213> ORGANISM: Artificial Sequence
<220> FEATURE:
<223> OTHER INFORMATION: reverse CREB binding site 2 sequencing primer

<400> SEQUENCE: 4

tgaaggcaga gtccaaaatc t                                              21


<210> SEQ ID NO 5
<211> LENGTH: 24
<212> TYPE: DNA
<213> ORGANISM: Artificial Sequence
<220> FEATURE:
<223> OTHER INFORMATION: forward CREB binding site 3 sequencing primer

<400> SEQUENCE: 5

tcgttgtatg ttagtgcatt tgga                                           24


<210> SEQ ID NO 6
<211> LENGTH: 23
<212> TYPE: DNA
<213> ORGANISM: Artificial Sequence
<220> FEATURE:
<223> OTHER INFORMATION: reverse CREB binding site 3 sequencing primer

<400> SEQUENCE: 6

cagaaaaaca tgacagcctc taa                                            23
```

<210> SEQ ID NO 7
<211> LENGTH: 21
<212> TYPE: DNA
<213> ORGANISM: Artificial Sequence
<220> FEATURE:
<223> OTHER INFORMATION: forward CREB binding site 4 sequencing primer

<400> SEQUENCE: 7
acacccacca ctgggagata a 21

<210> SEQ ID NO 8
<211> LENGTH: 22
<212> TYPE: DNA
<213> ORGANISM: Artificial Sequence
<220> FEATURE:
<223> OTHER INFORMATION: reverse CREB binding site 4 sequencing primer

<400> SEQUENCE: 8
actgactttc tatcagaccg cc 22

<210> SEQ ID NO 9
<211> LENGTH: 8
<212> TYPE: DNA
<213> ORGANISM: Artificial Sequence
<220> FEATURE:
<223> OTHER INFORMATION: CREB binding site consensus sequence

<400> SEQUENCE: 9 tgacgtca 8

<210> SEQ ID NO 10
<211> LENGTH: 22
<212> TYPE: RNA
<213> ORGANISM: Artificial Sequence
<220> FEATURE:
<223> OTHER INFORMATION: Mature Let-7f miRNA 5p

<400> SEQUENCE: 10
ugagguagua gauuguauag uu 22

<210> SEQ ID NO 11
<211> LENGTH: 22
<212> TYPE: RNA
<213> ORGANISM: Artificial Sequence
<220> FEATURE:
<223> OTHER INFORMATION: Anti-sense mature Let-7f miRNA 3p (*)

<400> SEQUENCE: 11
cuauacaauc uauugccuuc cc 22

<210> SEQ ID NO 12
<211> LENGTH: 87
<212> TYPE: DNA
<213> ORGANISM: Artificial Sequence
<220> FEATURE:
<223> OTHER INFORMATION: pri-miRNA let-7f (human chromosome 9q22.2-31.1) DNA

<400> SEQUENCE: 12
tcagagtgag gtagtagatt gtatagttgt ggggtagtga ttttaccctg ttcaggagat 60
aactatacaa tctattgcct tccctga 87

<210> SEQ ID NO 13
<211> LENGTH: 114517

<212> TYPE: DNA
<213> ORGANISM: Artificial Sequence
<220> FEATURE:
<223> OTHER INFORMATION: Sequence surrounding and including pri-miRNA let-7f human. GenBank Accession No.: AL158152.18 (AL158152v.18)

<400> SEQUENCE: 13

```
aaaagcaggt tagttgcttg ccacacacag tatccaatta acaaagtgag atctggtaca     60
aaacaagtga atttattcca aagctagctt atggaaagag gcacaaggcg ccgtgacttt    120
aaatgtgctg cttcactttt ggagcagaaa acttttataa ggtaggccgt gggccgggcg    180
cagtggctca tgcctgtaat cccaacactt tgggaggccg aggcgggtgg atcccaaggt    240
caggaatccg agaccagcct gaccaacgtg ggaaaacccc gtctctacta aaaatacaaa    300
aattagctag gcatggtggt gtgttcttgt aatcccagct acttgggagg ctgaggcagg    360
agaattgctt gaaccgggac ccaggaggcg gaggttgcag tgagctgaga tcacgcctct    420
gcactccagc ctgggcgaca gagtgagacg ctgtctcaaa aaaaaaaaga aaggtagggg    480
gtgaagtgtg catgggcagg gggtcccaat gctagcttgg tgacttatct atccaacagt    540
tgagttggca ccttcttggg caaaaataag ttgtaaacgt ggccacacca gcatgctttt    600
gacatgccct ctgcatgggt acaagttctg aggcaatccc ctggaggtga gagttccatg    660
gggtatgttt cagtctgcaa atcaactgtc aactgtcttg gagcacatag ttagatgaat    720
ttgccttgta ggtagtgtct ggtgagggga ggtgaagatt atatttgcat ttctgaaggc    780
caaagtagga agcaggaaac agagagggaa agaaaaagaa ataaataaga gaattttttt    840
ttaaatttaa actatctctt ggctgggcaa ggtggcttat gcctgtaatc ccagcacttt    900
ggaagaccaa ggcaggcaga tcacttgaga ccaggagttc aagactaccc tggccaacat    960
ggtgaaaccc cgtctcaact aaaaatacaa aaattagcca ggcgaagtgg cacatgcttg   1020
tagtcccagc tacttgggaa gctgaggcag gagaatcgct tgagcccaga aggcggaggt   1080
tgcagtgagc tgagatcgcg ccactgcact ccagcctggg caacacagag tgagactctg   1140
tctcaaataa ataaataacc gcctgaccat cacctgatgg ttgcctgaca ttccctccca   1200
cccctggagg ccctctcctg ccctgctcat gtctgcctga ctacctactg taacataatg   1260
atggtggttt tctctgggga gggctctggg aagggttgtt atatacaagg ggaacttgag   1320
ctttaactat catttgaatt tttatggcac aaatgtgccg acatattaac tgtattattt   1380
tttaaagtta gaaaaaattt tctagctcac aactgagttc tgatgtttgt tgattctgaa   1440
tcttcagcaa acctctatga gttgtaatat ttttacagta ggagctttgt ttttacaatc   1500
taaaatatct ttaaatgaac tgaaatttat ttttatttaa aatgtttttc ctaagaattt   1560
ctaaaggact gtgtttggaa aaaatctgct ttttaacaga tgtcttacat tccctcctca   1620
gtcctgtctc taaatattac ttggtaaaag taacacacta tttttctaga ctctgactaa   1680
tgcttctttg ggtttttttt tttttttttt ttttttggcc accgcccatt cagaacacaa   1740
cctctattac cagatgtttg tcttcctgct ttctatattt aaaagtcaca gatgagattt   1800
agctggtata gccacatagt tatttttttg tcaacagttt aaagttttga caatcggcat   1860
tggcaaacta atttgaagac caaaacaaaa aaaatcttga tttaattaaa gagcttaaga   1920
aagatttcag cctgtctgac ttccgcaggg caggccagga ggtcagaatg gcgctcagaa   1980
gtcctcctcc acaggaattc taacccggag cgcctgctgg ctactgccca gaaactgagt   2040
catgaagaaa ccccacgtgt aaaataatcc ttcaggcaaa tgggaaacgg taccttagaa   2100
tggactgtat cagagccatg gactcaagat ttgaatgaaa tacagagcca gctaagttcc   2160
```

```
ctcccgctgg agccattcat tcagcacttc attatggagc atcttagagt ccttcctggg   2220
cttagggaca caaatggacc acgggctgcg tcggctcctc agcagttcaa ctaagtgggg   2280
aggcaagctc tgggaacaga ctgcagcccc aggccagatg gcttcttacc gggaacatac   2340
caggtcatgt gaggccaaga gccctctggg aaggcagaga aggctccaca gaggagggga   2400
catgactcgt ggatttgtat gcagaaaata gagggacaag aattctggac aacaaaacaa   2460
tagatactag cactcccggc ctttcattct gaaaagccaa atcatccttt gtccacggac   2520
tgtagggaga ggttggggta gaaataaagt cagtgagtca ttctggtggc aaatttcaaa   2580
cagccccaac ccccactttt taaaacagtc cacaaacagg tgagcaagag tagcgcattt   2640
cttctctttc tttaaaccaa ctcagtgtag acttcaagcc cccatctctc cccaggcagg   2700
tgaaatacct gatctcagtc atgccaggcc tccaagaatg tgccacggtc ccaagaccat   2760
ccgcagccct acaggttggg ccaggtcctc tgctccccat cccagggcct gggctgttga   2820
gatgtggagc ctctggggag ggaccactag caaagctgga acacgtgtgt attctctctt   2880
taaaggatag aaatgtgcct agaggccagc atttccaaac atgcagaggg cctctctcca   2940
gctgggccgg gggtgagagc aaccctggca ttaagcctgt tcccattcca ccatctgcat   3000
ggatggctct gtccgaggtt tttaaccaca gacatcctgg taatcgggtt ccaggagttc   3060
agagacctgt cttctaattt ggcatcctct cttgacccca agaaaatcac ttttatcttt   3120
ctctttgtgt gaagtcagct ggccacaccc ccagccattc aatttgtcta cagattcttg   3180
ggcaaatgtc tttcagttcc aactccctgt ctccaaccct gggtcagtct ctgggtctct   3240
ttccacttcc ctccacaccc ctcagggcct gtctaaagac gcatcctcca cattctttcc   3300
ccacttccaa gtcccatggt ttccctggct ttgtctgata ggtaccaaaa tgggtcccag   3360
ctggagtcca gcttgtcccc cacagtgggg gccaatgtcg catcatcccg cacagcacag   3420
tcccctcacc tctgagacct cacttctgct gtgtttccac ccttcccccg gtgacatctg   3480
ccctcctggc ccacttcaga ggaattttct ccatgcactt ccccagaccc caggccagtg   3540
accttctctt agtctgagaa cttggcaaat tcttctcctc agacagcact cacttcctgc   3600
agtgagcatg ctgccccaga caactgcggg ctcctgggag gcaagggtgg ctcaggacaa   3660
agatttcccc agacccgcag agcccgctgg tgtccaaggg gagcagagga ggagaagaat   3720
ctgctacaag gagattctac aggagattct acagtgtgga gaaaattgca acgaggcaaa   3780
accacatcag catcatgagc tacaggcagg aatggaacag gttccacaga gtcaggaaag   3840
ggtccacctc catttaagtc gggcggcctc tggacagggg cgcaggggtg tggggcagac   3900
ctccccctct ctgcccctc atttgccccc ctgccagcct gcgtgtcccc tccctcggtt   3960
gcgctcccac cacctttgcc cttgtccctg aatccccagg catctggcct ctctggaacc   4020
agtcactggt catgtctgag gttccaggtc ccctgctccc tctgacctca gaagcagtgt   4080
agacttactg cccgctctcc tcccttggcc cctctggctg tctgacccct tttctgggtc   4140
ctactcctcc tcctggccca actgtcagtg ctgcccacac ccctcactgc ctcctgggga   4200
ggggtcaccc cactgcgccc atccctccca gccgctgtgg cctgggagct ggcattcacc   4260
acccagagcc aaacacaagg ccctggagct tgtcctgccc cagggccacc aggatgaagg   4320
ctggctgtcc tgctgcctcc tgtaccctct ctgtttcatt tccatctgta aaaggcagtg   4380
ccaagaatgg tggttgtcag aagctatggg gagcgggaat ggggagttgt tgttcaatgg   4440
ggacagagtt tcagtttgaa ctgaaccaat aaaaacgttc tggagatgaa tggtggtgtt   4500
```

```
ggttgcacaa tcatgtgaat gcatttaatg ccactgatct ggacaattaa aaatggtgag   4560
gatggtaaat tttatgttat gcatatttta ccaaaatttt ttgtttgttt ttttcgagac   4620
agagtcttgc tccaacctgt tgcccaggct ggaatgcagt ggcgccatcg tggctcactg   4680
caacctcctc ctcccagatt taagcaattc tcctgcctca gcctctgcag tagctgggat   4740
tacaggtgcc caccaccacc cctggctaat ttttgtattt ttagtagaga tggggtttca   4800
ctccactggc caggctggtc tcaaactcct gacctcatga tcctcccacc tcggcctcca   4860
aaagtgctgg gattataggc ttgagccact gcacccagcc taccacaata tttttaaatg   4920
agaagaaaga gcattgccca atagtgccta ctttgcactg ttgcttactg attaaatggg   4980
atgatgtttg cagaatactg aatgcaatgc ccgcatccaa taacagttca ataaatgacc   5040
tctaaattat ctctagatct tcagtcacag tctccagttg cctgccagac actcccacat   5100
acccttcata cctcgtcttg gggcaaatga aatgcctgct ggggctgacg ctgccaagag   5160
cagagcccag actgaatccc actcccatta cccctcagcc tgttctccac acacagaggc   5220
ctgacagagg aaacaggggt gggacgagac aggcctgggc agtgcagctc ccagagtggt   5280
ccccacttgg aaagtggggt gcagaaaata agagtcagga tttagaaaat ctatgccaat   5340
ctgacagtgt ctgatgaata gaataattaa agttgggttt gtattctgga tgtcttttaa   5400
aaatattttt ccagtagttt atctttacgt tatgaaagtg ttgatctgtg ttatattaga   5460
aatttttaaa aagagaccag gcaccatggc tcatgcctgt aatctcagca ctttgagagg   5520
ccaaagtgga tggatcactt gaggccagga gttcaagacc agcctggcca acaaggtgaa   5580
accctgtctc tactaaaaat acaaaaacca tccgggcgcg gtagcaggtg cctgtaatcc   5640
cagctactag ggaggctgag gcaggagaat cgcttgaacc caggaggtgg aggttgtagt   5700
gagccaagct cgcaccattg cattccagcc tgggtgacaa gagcaaaact ctgtctcaaa   5760
aaaaaagaag aagaagaaga agaaagaaag aaaaagaaat ttttaaaaag aactaggcct   5820
ttaccataga tagtttgaaa agccccaagc taggctgtgc caggataaca gatcaattcc   5880
taaatctcag tggcttaacc aacgatagcc tgattcttgt ttgaattccc acggggtggg   5940
ctaggtggct ctccccaggt ccagaaccca aggcctgggg ttgctgtgca ggggacagtg   6000
gacagaggag gctggagctt aactgcccac ctgctgctgt gtgtcctagg accagaagga   6060
ccatacagcc tggcggaggc tgagaaacac agcacagcca gtggatagtg ggtgacaaga   6120
gggtctgcca ccttgtagat ctgaacctgg gctctgctcc tgggatccgg gtttctgtaa   6180
aggagctggt cttcactgtc attaggtgcc tgagtcttaa aagcaaaggg ccatctttgg   6240
cccttgtctg cctgtttttg caggtcctgc ctgcaggcag cccccagccc agccccacag   6300
cttcccattt cccgcaaact atcaagcaca cactgcattt cttcagtgcc caataaactg   6360
tgaacactct tgttaaacca gactactcac tatcttcaca ttttccagct ccctgccttg   6420
gctccaaaca gttggtttcc tggaatctac ctctcctcag tcctctcctt cattcttgca   6480
tgtccaagca ccacccatcc ttcaagcctc agctcaaatg ccaagtcttc caggaaggct   6540
tgtgcacaag ccaagaatga gcattagaac acccaactga tagtggctta agtaacagag   6600
acgtttatct taccagaagt ctccagcaag gtggttccag gttctttcag cagctcgctg   6660
atgtcaaggt caatggtctg gatcagcatc tctgctgacc ttcagggctt tacttcttga   6720
tcacaagaca gctgcagtag tgccgtgatc atgtcgttac acaactgcag tcaaggcaga   6780
aagaaggaga ggcagcagga aaaaaaaaag gtgggcagtt ttccttttct attatagaag   6840
gaagcatttc ctagcaaacc ttctagcaaa attcccctga catctcattg gcgaatacta   6900
```

```
gtccatgtag ccaaacctgc cctaaatgtt ggggtatctg ggatagtatc tggcctgggg   6960
gatgaccttt acataatggt ctcatccatc atggacctgt ctcaggagtt aagagcagcc   7020
agggtgctcc tagcaagaca gaaggcagct gggcgcagtg gctcatgcct gtaatcacag   7080
cactttggga ggccaaggtg ggtggatcac ttatggtcag gagttccagc ctggccaaca   7140
tggtgaaatc ccatctctac taaaaataca aaaattaacc aggtgtggtg gcaggcacct   7200
gtaatcccag atactcagga ggctgaggca caagaattat ttgaacccag aggcagagga   7260
tgcagtgagc cgagattgca ccactgcact ccagtctggg caatagagca agactcagta   7320
tcaaaaaaaa aaaaaagaag gcaatggctc tagtagagtc agcaacagac agaggctgcc   7380
acaccttccc catcctttct gtttccactt gcaagtagtc ttgtattctc taaatgttta   7440
cagcttctta tctcccatgg ctcataatat ttcctacctt ttcgttatca gttaggattg   7500
caaacctggc ttgcagtggc tttgttgttc tcacataact ataggttgga gagaagtgag   7560
cattgacatg ggtccagcag ttcactaatg tcagcgtcca tatctgtgct tctcttggtg   7620
gtttctctca tggttacaaa acgtctgcta caactccagc ttttgagtct tcacacaatg   7680
tggaaagata tggggaggtg tggtgacatt tgcatgtttc tttttcagg agtgcaaaaa   7740
agtttcttcg aagcctctga gcagacttca acatgtttca ttggacaaaa gcctatcaca   7800
tgaccacccc ttgacgtcag tctgatgagg ggagtagtca gcgtttctgg ccttgatgga   7860
agatggttag ggatgtcatg actggtgggc cagctgggat gcctgcagct ctccttctgt   7920
atctgtcatc tcctttggac tgagagctct gtaagagcag ggatattgct tatttctttt   7980
tttattatta ttttattttg tgtagagaca gggtcttgct atgttgccca ggctagtctc   8040
aatctcctgg gctcaagcaa tcctcccgcc tcagcctccc aaagtgctgg gagtgcaggc   8100
atgagctact gcgcccagcc tgtttcttat ttatgacttg gacctgatta tacaggagtg   8160
ttgtggtaag taactgggac agtgcatgct gagaactcat gtgtgctgag ccatccaaga   8220
gtggctgtcg ccatcatgaa caaggagcag tcacagcacc ttcagccccc cagggcccat   8280
cttgtgtctt gaacatattt gatgctgggt gcctgcatgc tgaatagggg ctgagagtgt   8340
ggggtgtggg ttttcactcc ttcctccctg ctccccatgg tctcatgagc atgtctagca   8400
gtgtaacaca cccatgcttt tttgtgtgtt tgatacagag tcttgctctt tcacccaggc   8460
tggagtgcag tggcgtgatc tcggcccact gcaacctccg cctcccaggt tcaagcgatt   8520
ctcctgcctc agcctcttga gtagctggga ttacaggcac ctgccaccag gcccagctaa   8580
tttttgtatt tttagtagaa acggggtttc accaggctgg ccaggctggt cccgaactcc   8640
tgacctcagg tgatccaccc tcctaggcct cccaaagtgc taggattaca ggcatgagcc   8700
gccgcgccca gccacaccca tacattttac catgaacctt cacatctata ggacaacctc   8760
atctgtgagg caacatagct tgccaggaaa agagaaagag tcatatggaa catgacacat   8820
tgcagccttg gaaaggttat cctacctctc tgtgcctcag tttctctgac ttaatgaaag   8880
ctaatttctt gagcctctta gggctgtgga gatgaaataa gagataacac atgacaatgc   8940
cggcccaaca tgggtgctca actagtgccc cttgtttgga ctggctgatc ctccaggaac   9000
ccccaggcag gcagacgaga caggcactga gggctgggaa aggccaagtc agagtccaca   9060
gactggcgat gcccaggatc agagaggaag ggctgagaga tggcctcgtt caacacacgt   9120
gaatgaagaa ggaacaggag aggccagggg ctacctgcct cagatggtcc ggctgtggtg   9180
gggtggtggc cctatccccc aactcctccc tgctaacctg aggccaggat gctgtgccta   9240
```

```
ggagtagctg gattttagta ggttcatctt ctcaattaca caggaccaca gactctttca   9300
gtaaagagcc agaaagtaaa tacttaagac tttgcaggtc atgcgtggac tctgttgcat   9360
atctttgttt ttgttgtttt gtttttcgct ttttgtttta tataatgcct aaaaaatggc   9420
caggcacggt ggctcatgcc tgtaatccca gcactttggg aggccgaggt gggcagatca   9480
cctgaggtca ggagttcaag accagcctga ccaacatggc gaagcctcgt ctctcctaaa   9540
aatacaaaat tagccgggca tggtggcaca tgcctgtaat cccagatact cgggaggctg   9600
aggcagaaga attgcttgaa cccaggaggc agaggttgct gtgagccgag atcacgccat   9660
tgcaccccag cctggacaac aagaatgaaa ctccgtctca aaaaaaaaaa agagtctaaa   9720
aaatctaaga accatcttgg cacacgagct gcaaagaaag gagctgcagc tggatttggc   9780
cgcctggctc cccgacacgt cctggcaccc ccgaagcact caaggagctt ccttgcttca   9840
tcccctggag gaaagccggg cctggccatg gcgctattgt gacgtggctc ccagagcagt   9900
ttcaggcctg ttctagcatc tggccggggc ggcagcctga gagccatgga gccgctgggt   9960
gcaacactgt cctgcccgtg tgcatggagc tgcttacgtt gcctgcactg ctgctgtcct  10020
gttcccacaa cttctgcaaa cagtgcctgg agctgatctt ggtttaccag aattgcaccc  10080
aggtccaggg atggttctgt tgtccagtgt gtaggaaagt aagaggaaaa tcagggccct  10140
ttgactccac gagggagcag acttctttct ggtctgcact cttcgaactc tagcccatga  10200
gaaaactggg gactttgggc cccaaaatga agaccagcaa ggcagaccca catctctgaa  10260
gggttgtgag agggcatcgg caggggagga caggcttttc ctttaggctt agaagatcca  10320
tcaggaccca cagggaggag ctacaggagg atgtacattg tggcctaagg ttggagagaa  10380
ctttcttaca gaacagcttg ttcagtatgc gctggggtag gtagggccat ttattagcac  10440
ttgctaggtg ccttgtcact gtggtggaag accagagaag cagagctgat gagggttcag  10500
atttcaccct ttaaggagag atagaccaca catataatgg gagaccccac agtgcaggtc  10560
tgcaatgcac cgcaggggac aggaaggcca caggggaggc actgctgcat agaatctacg  10620
gtaggactga tgctgatgga gagggcaatc taggaagaga cagtggcaga tagcaaggcc  10680
cgagaaagag agcctaagaa aggaggtgct taagggcctg gcccagagat cacggaggct  10740
tgagcataag gtgctgtggg agacacctgg ggctttaggg tacccacccg aagggtaagt  10800
aggacatatt ccaggaggcc ctacacatca agcaaagggc tttgcatttt atcctgtaag  10860
cagaggggag ctagtgacat attttaacct ggaaagggtc atcataacgt tgacttctga  10920
aagcacaatg tcacatgctc tcatggaaat tctttgtgta acatttcgcc agctggactg  10980
taggaatcat gactggtgtt gccccagacc ctttggatat ttgtggaagg aaggaaggaa  11040
atctagaagg aataggttgc aggcagagga atcctgaggg gctggagggc agggagagag  11100
gcaggcggtc atcacctggc ttttggggga ggggtgccat gaggtgactg cagagacagg  11160
ggcaacagct cagaagcacc acacatttgg atggatcatt ttatttgtca acctggaatt  11220
ttcacttatt tgtatgttta tttttaaatc atatcaaaga aatagtgtag aaaagagttt  11280
ataatgaaaa gcaatgctgc catcccaccc ctagtcccac tctccagagg caatctctcc  11340
taactttttc tacctcattc ttcctgcagt caccaccata gctctgagta tgtgtttatc  11400
tcaccattct tcgcccactg gttttagacg ctactggcat ttgctgcctc tccgacgact  11460
gagcttctcg tgcacagctc cttcctcatc ttccctccct gagcaggtcc atggcaacct  11520
taatttctct attgtgattt taagttaatg caccaagcaa ctagagataa tggcaccctc  11580
tgaagctcca ctttgtaagg gaggcggtcc ttgtcccctg ccctgctctc tggctttcct  11640
```

```
gctcccaggt gacagacaca caggctcctc agactccggg agcccataag gaacctgcaa  11700
agggcacagg aagtacactg gaggtcttcg cagaaatttt gttgagcctg gatttggggg  11760
ttgggcaggt catgcaggtg cggtcccaag agggttgagc agaagtagct gtgcgtcctc  11820
accctgacag aacacagagg attgagcaga gggacagtgc tggctgggat actggctgca  11880
cctgcggcct agaagggcgg gaaagagctt tggactgatt gagtagaggc agagatttga  11940
gaagggaggg aggaagagga ctggtgtgcc cagctctgaa ggcagaccct ctgggacatt  12000
ttcagtgctc ttcagttttc tttgaaaaga aaaaaggccc agatcccagg cgcaggccca  12060
ttcatcttcc ctggagtatt cattctgctg aatcctggaa aagatttata caccagcagc  12120
attctgtagt gagtgttatg ctggaattca aacccaggtc cacctctttt caagacaagt  12180
tcttttctca tttccgaggc accagggaaa agaaatcact tccctgcact ggttctgttg  12240
gggccaaaag atcaggagat gattgccatt gaaaaggtag tttgttactc agagttccca  12300
agaggaggga gccccccacc acgcagggcc acatggggaa gccccagggt tgatcaggaa  12360
gcaaaaggaa tggcagggaa ctgtggtcca gggcctttgc tgtggtttcc acaggaagaa  12420
atggggaggg gagggtaagc aggctaaaga ctggctagtg tgaatcattt cagtgggctc  12480
tgaggcatag gagctgtgcc ttgctctctg gtaattaggg cagatggaca gtggcctgcg  12540
tgtgagaagg ttggatggtt gggggtgtgg gatctgggtt ggttggtttg catctgaaaa  12600
gcacagtccc aggtgagatc ctttactctg tctaggagtt ggctaaccct gggagggcag  12660
gccccaggtg ccaaaacatc aaaatacaga aaataaaaga cacagtgaga cctggtcctt  12720
cgttctctgc actccactgg catatccaac tgtgcagtca ttgactgtga gcatttctta  12780
ccactggact gagtttctgt ggaagacaga gtaggtccta accaaaactc aatggactga  12840
aggaacgcag attccagttt cacctgatgg agtttgtagt gactttcaca acagatactg  12900
gtaacaggcc cacagcaggg ccagcctgga agtgtcatcg tgcagggttc tcacagtcac  12960
ttccctctcc aggtcttgtc agccttcccc agggtggaat gtgagttctt tcctcctccc  13020
agatggtgtt ttagtgacca ggaagggaca tatttcaacc tcccccaaag atgaggtggc  13080
ctttggcctc aggaatttgc cacaaactca tgtgatctct gtgttttagg acatttattt  13140
gaagggcagg ggaacaaatg gattgcaggg aaacatcctg gctgaaaata tcctggaaaa  13200
gcttaaggaa gtacttgaga cacttcacac cggggagcaa aaccagctcg ctcagatgtg  13260
tgaaaagcgt ggaaaaatca tgaatctggt attaaattat actttttaaa attttctttt  13320
tgcctagctg cccaatctgt caaattactc ggtaagccta catagttgaa accagatgtt  13380
tactcaggag tatagtagag gattactttc caaatccaca gcccagtgct aactttattc  13440
ttgatttgta acgtggagcc cagggacgaa tgtgtgtgtg tgtgcggggg gtgagggggt  13500
gcatgtgtag ggggggtgca tgtgtgtgtg cgcgcacaca cacacatgca gtattcagcc  13560
ctgcagccca cagtggggtt gaaggggtca catgtagaag ggctcaaaca ggtacagtga  13620
tttatgagat ttatgagact ccagccaccc tcagtcatct cggagagagg gtgcggtagg  13680
atgagactgg cgaaccggct attccttctg ttgcctcctg aatggctggt gaggagggac  13740
tcctttggag agctgagtgt aattctggcg tttggatgct cagcacacgt tttccgcaca  13800
gtgtgccata tgaacccttg gttgtttctg tgcaatgctc tgtacattgt acatttctac  13860
acacatatct acagtgtgcc ttgtacaaaa ctagatgtgt tctacaagac actccacatt  13920
cccttgctaa gggatcttca aagggaattt tgaggtaatt ttccccttgg gcactgactt  13980
```

```
taggatggat ccttctgtca gatgggatac ccctttaaaa ggctttaatt ctttgctgtt  14040
cacaaagcac gtttacaacc tttagcctac ttgactcccc gagcaacccc ggaggggcag  14100
gagaaggcag agtttccatg tttcatagat taggtagcat cagccaccag ccttaggggc  14160
ctcatctagg ttgcttcgtc tttgctcatt atcaggtgta aactaagttg acaatttttt  14220
tttcgagacg gagtctcgct ctgtcgccca ggctggagtg cagtggcgcc atctcggctc  14280
actgcaagct ccgcctcccg ggttcacgcc attctcctgc ctcagcctcc cgagtagctg  14340
ggactacagg cgcccgccac aacgtccagc taattttttt gtatttttag tagagatggg  14400
gtttcaccgt gttagccagg atggtctcga tctcctgacc tggtgacccg cccaccttgg  14460
cctcccaaaa tgctgggatt acaggcatga gctaccgcgc ccggcccccct aagttgacaa  14520
tttacttgga agaagtcaaa agtattcatg agacttcata attctgccgt aacttgaaac  14580
tctgaagcca actccaaaag cagagatgtg gctctgaaag aggctctgga agagggtctc  14640
ctagctctga atcaagtctg ccgcggtgag gcagggtctc cctgagatcc tctaccctca  14700
accagctacc tgggccaccg cctgagccac tcctctcttc cttgcagctt gcacttctgc  14760
tgagatcaat gacactgctt gggacaggct aggtcaagcc cctgaggtgc aattatatat  14820
tcctctttag actatgcctt taagaattgg tttagttttt cacaagtttg ctatggttct  14880
gcctcatctt cagcagtcac ctctatggtg ttcattcaga gcctgcccct gaactgagta  14940
aggaaggggt ggaagcagaa gaagcaggca gaggggatgg ctcctctttg atcccctcca  15000
tctagaaatg tgctcagctt tcagtcccgt agtggggctc actttgtttg tgaaggtcct  15060
tgtaatatta tcaatagcta ccaggggttt aatgtcatcc aggtgtcagg cactactcca  15120
ggcatcttac gtgcatcgcc ctatttaatt ctcatggcag tcctatgagg caggtggtgt  15180
ggtaatgtgg gaaaagctct gaccttagac tcagaaggac cttgtcttct aatcccagtg  15240
ctgtcccttc ctggcaagtt atttgcagcc ttctgagctt cgtcacccat aaaaccgtac  15300
tatgtaggct gggtgcagta gctcacactt gtaattccag cactttggga ggctgaggcg  15360
ggcaaatcac ttgaggccag cagttggaga ccagcctggc caatatggcg aaactctgcc  15420
tctactaaaa atacaaaaaa ttagccgggt gtggtggcac gtgcctgtag tcccagctgc  15480
ttaggaggct gaggcaggag aatcacttga acctgggagg cggaggttgc agtgagctga  15540
aattgcacca ctgcactcca gcctgggtga caaagcaaga ccccgtctaa aacaacaaca  15600
acaacaacaa aacaaaacaa aacaaaacaa aaaccatact atctaaagca aagggtggtc  15660
gtgtgaggat tccgtgaaat aacaacatgc acttactaaa tcaccaccag accatcctag  15720
tactatcatc acctctgttc tacacacacc agggtgtcct gtgcaactga cttttaatac  15780
ttgcttcaca cattcacaat gtcatcagcc tgggtagggc aggtctctag tgcatagggt  15840
tggaaaagga aggaaagaaa gtttcactga cttttcttct ctcaatcagt tgtgcctaag  15900
tgatgaaaag ccaatatgca ggatattcaa gctctctggg gaccacagtt ctcaccaggt  15960
agccaagatt gctgatgtgt acacagaaag gaaagctagc tttgctgagg acattcagca  16020
ggtgctgcag agatctgaga gcacagccca ggaaacggag gtatggcttg aatggttcct  16080
ctcctgtccc cacattaaca ggaagacaat gtttggttct ggtttcaaca gttttctctt  16140
cagagcacta ggccaacaaa ggtagtgtat aaatgcaaag gagaaatcat agattgcatt  16200
ctctagagac aggttcccct tgagtctgtc ctgaaacatg ccaagttttg aaatgcgcac  16260
cttaagaact gggtcagtcc tgattgcttt caggacttca aaaaatgaac agttaatagc  16320
caattaattt accttccctg agttcagaag atggagctaa gagtctaggg agaccaaagc  16380
```

```
agttagagta cataggacag agttcagaga ggagatggtt acacaaacag agatcctgga  16440
gacctgtcag ggtcttcct tgagtactca gcagtgaact gatcagcata tgtctgtgaa  16500
gacactaccc aaggtcagac aaggaaacat aaaaatattg agggaagagc acctgatgct  16560
tgcacaggac aaggaacaat gcctatttcc acaagaccgg aaaaactcat acatcatgga  16620
acactgggaa gagcactcag aaggtcttgc ctccaagtag tcagaataat tagccctaga  16680
tggaccactg ctgtggaccc acctaaaaaa caataaaagc aagacctgaa aggatcaaac  16740
tctttccaag tacctccact gcatcccata acaaaattga agatttatag gaatacaaaa  16800
atatccagct cccaaccaag taaaattcac aatgtctggc atccaatcaa agattaccag  16860
gcaggcaaag aagcaggaaa acatagtcta taatgaggac aataatcaca caatcaaaat  16920
caaatcagaa ctgagacaaa tgttagaatt agtagatgaa gacactgaaa cttattataa  16980
ttatattcca tatttcagaa agttacagac agaaaatata aaaatattca aattagatct  17040
acatctatgt actcaaacaa aaatttaaaa ttttcaaatt tttaaattat ttttatttat  17100
ttattttttt ttttgagaca tagtctcact gtctcccagg ctggagtgca gtggcacaat  17160
ctcaggtcac cggaagctcc acctcccggg ttcacgccat tctcctgcct cagcctccca  17220
agtagctggg actacaggcg cccgccacca cgcccagcta atttttgta tttttagtag  17280
agacggggtt tcaccgtgtt agccaggatg gtctcgatct cctaacctca tgatccgccc  17340
acctcggcct cccaaagtgc tgggattaca ggtgtaagtc actgtgcctg gccaggatcc  17400
ctttcttaga aggcaggaaa ctgagatcca aggctgccca gctagcaaga accaagattc  17460
tcctgggtct gtgtggcttc ttcattggtg tgctttcccc tactttttgc tgccccatct  17520
ggaaagacct gatcatgggg tgatgctggt actgggtttt atttctttta tttatttttg  17580
agagagggtc ctgctgtgtc acccagtctg gagtgcagtg gcacaatcac ggctcactgc  17640
agccttgacc tcctgggctc aagggatcct cccatctcag cctcccgaat agctgggact  17700
gcaggcatgt accaccatgc tcagctaatt tttgcatatt ttgcagagat ggggttgtgc  17760
catgttgccc aggctggcct caaactcctg agctcaagca atccacctgc cttgggtctc  17820
aaagtgttgg gattacaggt gtgagctgcc gtgcccagct tggtgctggg ctttaggggt  17880
gaactgaaga ccaccagttc cggagtatga gatcttgact ttttctagaa atattagaat  17940
ggttgcatct gagatttcat ttatttccct ctaaattatt caggtgattt cttccatgtg  18000
gctattcttt caacaatgat ctgcatttgg ctgtagcaga agtccatgag cagtggcttt  18060
aaaaaattag ggttctatt tttttacttt aatgaaatgt cccaaggtag gaagtcaagg  18120
ctggctggct tgggatccgt gatgctccag ccctttctc tcagccattt ggtaggtgct  18180
cttgtcagca cgtagtcaca ggatggctgt cccatatagg catcctgtcc atgatcccgg  18240
caaagggaaa gggaagggtc aagactggtc ccaggggcac atgcccactt ttaagcagct  18300
tcctaaaagc ccacctgact ggattctact tctgcttcca ttgcacacct ggttactccc  18360
aatgtcaagg gaagcaggaa atgaatgtag tatttttagc tgcccacatt ggttcccccca  18420
aagaatcaga gttctttggg tagaaaagtg gtgaaaaacg ggtagtgggc tggcaaccag  18480
cagtgtctgc caggcctggg gcctccctgc ctcagggtgg aagcccgggc agagcagaac  18540
ctgtgggctg gagggcctcc ctgcagggct tgcctaagtg tgtgttagtg ctcccttggc  18600
aggacacaga gaggctcatc agacctgtcc accagcacca ccagcacaag gaccatgatc  18660
aaaaccatcg gaaactgcct gatcagcggc atccacagcc gcagccacat ggttacctca  18720
```

```
aagcaggagc tggagcatgc ctccgagttg gagaggctgc agtgggtggc ctgggacctc  18780
acagtccccc gccagctctg ccaccagatg ctgaggctcc tgcagcagca ccagaatgcg  18840
atatagtttc tgcgagaaag gacaaaaagt tcaggacgga gatgaagagg ctcatgcacg  18900
atggcatggt cccccaggtc cctgaaaagg acaacatgtc tatcaggcac taatttcaag  18960
agctcattaa aggaatagat attgctgact tggtcctgcc tgagttagcc caggcgctgg  19020
ccaccgtggc caggctgccc gaggcctgca ggatgggcag ggccacgcag agcgaactgt  19080
tggaacaaac gctccaggag attttatgca agtcagagtt gggcttgctg ccaaaaccga  19140
acaaagaggc aaagcttcct ggggacccat gttattcctc ctccacttcc tccactggtg  19200
tgttctccac acaaggaagt gggcttaagt ctagggaatc aacagcgtaa agtcatattt  19260
tggcctcaaa atgtcaaaaa ctttgatcat tttgcctgta atttgaaagt tgctagactt  19320
cacttcttaa aaagaaaaaa aaaaaaaaaa ctttccacat tgtgatctct ctcttgattt  19380
gggttattct gctgctaatt aatcatccaa agtttttttt tttttccat ttttaatgga  19440
aacctgcttt aaaagcttgt tgctgaaagc taacatagga gggctttaac tagtgggaga  19500
tgctgagctt ggctgggctg gaggtggtgc aggaggtgag ttcttggcac aactgaacag  19560
aacagcatcg tgctctgatg acttactgtg caatttcagc tcaattgagc ttcaaatact  19620
agacattaca acggcaatga ctccacagaa atgaagcctt ggttagctct tgtccatgga  19680
ttttgttctt tttccttcac aacagtccta actacagttt attaaatgct taccatagac  19740
tactatgcac cctttatatt aatgagttaa tttaattctc aaaataacta aaagagctga  19800
gaattattat ctccacctta taggtggaca ctcagggtca aaaaatgtaa ataactggtt  19860
taggatcaca tatttactta aacagtgagc cgtaaaacaa attcaagtcc atctgggtga  19920
ggcctgactt cttgtaggat attcctaagt ctctgaaagc agtactgatt tggaaacatc  19980
accttaaaga acactgctgg cctgccgcgg tggctcacgc ctgtaatctc agcactttcg  20040
gaggccaatg cgggaggatc acttgaggcc aggagcttga gaccattctg ggcaacacag  20100
gaagaccctg tctctacaaa aaaaaaaatt tttttaaatg gtcaagcatg gtatccccca  20160
cctgtagttc cagctacttg ggatgctaag gtgagaggac agctttagcc taggagttcg  20220
aagctgcagt gagctatgat cgtgccactg cactccagcc tgagtgacag tgacatccta  20280
tctcaaaaaa aaaaccacta ttacaattct ccagaagttc actcactctt ctttccagtc  20340
cactagtttt tattaaacat ttatcttaaa attcagtgtt tatgaattac tttgtgaatg  20400
tctattatga caagcactga gtttaatgct ttacatacat tacgttatga gaactccatt  20460
ccacctgagg aggtaagcat tagagtgcct agtgccgaac gaacagacag atgaactgag  20520
gtgaaaggag atcagcagtt tgtcgaaaat cgcaaatagc atggtagaaa tgtgggttct  20580
agatgttact ctcaagccag tcctcctcct aaccacttta ttagtaacat ctctggttgc  20640
atgtgacaga aattccatcc agctccaggt gagaaaagag ggaaatgtac agcttctgat  20700
gctcaacggg gaagggatgg agtgtccttg aggatgcctg gatgtgggga ctcagctgct  20760
atcatgacct ctttctctgt tttttgtctc tttttctttt ttctttttga gacagagtct  20820
tgctctgtca cccaggctgg agtgcagtgg caccaatcag ctcactgcaa cctccgcctc  20880
ctgggttcaa gcgattcatt ctcctgcctc agcctgccaa gtagctggga ctacaggcgc  20940
ccgccaccac acttggctaa tttttgtatt tttagtagag acggggtttc accatattgg  21000
ccaggctggt ctcaagctcc tgaccttgtg atccgcccgc ctcagcctcc aaagtgctgg  21060
aattacaggc gtgagccacc gcgcccagcc ttgactctgt ttcttgactc ttgctttgct  21120
```

```
ttttctgctg tggactgact tcttctcaca tgtcattaca gcttgggatc tgcagctaag  21180
aggacttcct tctcccagtc catgtttaca tttccaggaa gggacactgg ccttattgag  21240
gtactgtccc cttataggac ttaccagtgt gtgttaccca ctcacctctg tggttaaggt  21300
actgtgatta acagctgaga ccacaacccc acaactaaag tggggcagga gctgtatttc  21360
aaaagaagag gcatgcttcc aggccagagg acacaaattt agatgacttc aggggccagg  21420
cttgtagtaa gaatgaagca ggctcaatgg ggactgtgac aaatagcaga gcccacgctg  21480
cacataaaga aaatattgtc atgttggaat gtaggctgag tgtagccaga gatgccaatt  21540
ttttctgaga gaagcaagaa atctagattt tttttttcct gttaaatgtc ttgattcttt  21600
tgcatgctgt cagctagtta aaaatagctt taaaacattg cgtgggtata agaaggcact  21660
tctgtgaacc agatgtgacc cccaggccat caccagtttg caaacccctg gttgtaggta  21720
gaaaatataa taaatgtcca ctccaccccg ggaatgctcc ctggggagat tcactatgcc  21780
tggagcctcc agctgtgggt tttctctctt tctgctgtaa ctcttcaaaa ggcagctctt  21840
ctgagcacac agaaaatggg aggctcctag gtgaggtttt ggaaggcact atccagacat  21900
caccctcatg gtcaacacat ccaccatgct ctgtgctaag acagacctgg gttgactgtt  21960
gcagaagacc cagcgtatta ggcagggttc accagagaaa caaagccaag aggagatata  22020
tccagatata aacagattta ttatgaggaa ttggcttgtg tgatttatgg aggttgagaa  22080
atcccacagt ctaccatctg caagctggtg acccaggaaa gctagctggt ggtgtggttc  22140
aaaggcctga gaacttgaga gctgatggtg tagattccag tctgagtctg aaggcctgag  22200
agccaggagc actgagacca ggagaagatc aatattccag ctgaaatagg tggtgcaaat  22260
tcaaccctcc tccacctttt tgttccattt gggctttcaa tggattggat gctgcccacc  22320
cacactgggg agggccactt gctttcctca gtccaccaat tcaaatgctg ctgccttcca  22380
gacaccctca aagacacacg tggaaataat gcttggccac atatctgggc accctgaggt  22440
tcagtcaagc ggacacataa aactatcaca ttcaggaata agagcaggaa gtctaacctg  22500
tgaatagttg ggagaccaag aggcaaactc atctttgcaa caccatgtga tgagtgtagg  22560
gccggaggag agcagctaca caaaggcaga gcactaaatc tctcctagag aaaggggctt  22620
agggagggtg aaggtcacaa tttccaggag tatgtgtttg ctttacctta gttgtcttgg  22680
ttacaaggaa aacagactca tttgtccagt tgcagaaagg tagagggagg gttctgtcct  22740
aaggctgcat ggagacagat agacaggtag agttgcaatc atgagatggc aaggcctctg  22800
ggacacgggc cttagggaca aggggcctct ggctgtggtt tggagtttgg ctactctagg  22860
aacctcagct gcaggatttt ggtctactca ctactcagca tctctgccca gttttctcct  22920
gggcccagtc agctgcttct ccctcaactt attcatactt tctgtgagtc ctgactttca  22980
tgagctaggc tccccttgtg gccactcctt ttatttgtgt ccttcaagct cagcctccac  23040
tttttttttt ttcaggtgga gtctccctct ctcgcctagg ctggagtgca gtcgtgtgat  23100
ctcagctcac tgcgctcact gcaaccctct gcctcctgcg cccaagtgat tcttgtgcct  23160
cagcctcctg agtagctggg actacaggca tttgccacct tggctggcta attttttttt  23220
ttttaagtaa aggtgggatt tcatcacatt gcaccatgtt gcccaggctg gtctcaaact  23280
cctaagctca ggcaatctgt ctgcctcagc ctcccaaagt gctaggatta caagcatgag  23340
ccaccgcgcc tggccatctc ttcactttta attctacgct tcgagagata tttactgggt  23400
acctactgcg tttgccaggc cctgttctag aatgtaaaat acagtagtga aaacatgcca  23460
```

-continued

```
gacaagttcc tcgccctcat gggggtagaa catcaataaa acaagcaaga tggagccaga  23520
gagtgccaaa atgttacagt gttacaaaaa cagagtggtg aaatctcatt aaagatggag  23580
atttacactg ggtggccagc aaagtcctcc ctaaataggg gaggttcaag tgccatctgg  23640
gtgacaagga ccagccagac gaagatggga caagcatgcc aggtgacctg agcagtggca  23700
ggagtggtga atggagaggg aggcccaggc tggacacggg agcaagctcg gacttgaacc  23760
caaggaatac catgcgctgc tttgctctgc aagcaggttg ttctgtttga ccccagacaa  23820
acagcgaaat gcatgctctt cctaaccctt gccaaataat gatcattaat gacaaccagg  23880
ctgtttatca ctcagcaatc ccaaatcact ttcctaggta tgatctagct gaaatacgga  23940
gtctctatcc aaaggaactc cgttcctagg aaacggagtt gctggacatt cactcatgtt  24000
tgttctgttc caaaggctgc atgttctctc cacaaaatgc ctacatgcat gtctaccaca  24060
tcgggccagc ttccggcaga agtataccca aatttcaggg gcttacatga gatggaagtc  24120
atgtctttct cacttaaagt ccaagcttgt gtagagggtg ccctgtgatg ctaccagggg  24180
actcaggtta gctcttcact gctgcttgca actggtggac atagtggctc tccaccacac  24240
cccaatcaca tccaagtagc tagaaatcag aaagcgggag acagagggaa tccagaaccc  24300
ccttccatcc tgctcacagc tcaccagcca gaacttagtc acacaggtac agtcagggag  24360
taatttaagt ctaccatcac caaaaaactg ggtttctgtt tattatagaa aaaggagaca  24420
ttggatattg gggaacaact atcggtcact ggcatggctt ttattttat attttttcct  24480
agttatgaaa gcaatacata ctaccaggaa tccagatata tatataaaga aaataaaggt  24540
taggagtaat tccagatcta actgttgtta taagacaaac aaattttttg taaccttact  24600
tctcacttaa tagtatatcc tggccgggca ctgtggctca tgcctgtaat cccagcactt  24660
tgggaggccg aggtgggtgg atcacgaggt caggaattca agaccagcct ggccaagatg  24720
gtgaaaccct gtctctacta aaaatacaaa aattagctgg gaatggtggc aggagcctgt  24780
aatcccagct actcaggaag ctgaggcagg gtattgcttg aacccgggag gcaaacgttg  24840
cagtgagccg agatcgtgcc actgcactcc agcctggacg acagagcaag actctgtctc  24900
aaaaaaaaaa aaaaaaaaat agtatatcct gataatcttc ccgtatcaat aaacatagat  24960
ctacattact atgagaactt tttttttccc ttgagacgga gtctcgctct gtcgcccagg  25020
ctggagtaca ctggcacaat ctcagctcac tgcaaactct gcctcccggg ttcaagtgat  25080
tctcctgcct cagccttatt tgtctgtatc tcttggatgc ctgtcaggtg ctaggccctg  25140
tggtggtgac tgggtgcaca agagagagca agacaaagtt ccagctcaat gaattttatt  25200
tcccctgttg tttacaaatg ctttgatttg acttgtagat atttgtcaac cattagtatc  25260
ttggttctat tgaaggagta agaacatttt aagctgaaat tcttctttct tttcaattga  25320
gatggagtct cactctgtca cccaggctgg cgtgccatgg catgacctca gctcactgca  25380
gcttctgcct cctgggttca agcgatcctc tcacctcaga ctctcgagta gctgggatta  25440
caggcgcacg ccaccacgcc cggctaattt ttgtattttt agtagagatg ggatttcacc  25500
atgttggcca agctggtctc aaactcctga cctcaagtga tccccccgcc tcgtcctccc  25560
aaagtgctgg gattacaggc gtgagccact acgcctggcc acgatcatac cttttcatgg  25620
catgtttgga ccgtaattta tgcagtcacc tatggtgtac tggtagatgg ttgtgatttg  25680
aggctactat aaacaagatg atgaacagcc tgtggaggat ctttgtatgt ttgtcctgtt  25740
attttctagg cataaattcc tagcagtggc aaaatgctgg attaaggaac actttcaaag  25800
attccgattc ttgctgccaa attggcccct agacttgcag aaatttatac taatgcctcc  25860
```

```
aatgtttcct tctacaatgc cactgatcaa ctaagagata agaaagcttt cattgtttaa  25920
aactttgtct ttatttgatt actagtgagg atgagcatct tttcatattt attggccatt  25980
ttcttttgta aattgtcagt tcacatcctt tttaaacagt ccatatttta ataggagtgt  26040
tcactttatc ctattgattt gaaaaaaaaa atccacttta ttaaggataa catattagca  26100
aatgcttatg tagtacttat gtgtaccaag cactgttctt agttcttaag atgtttatat  26160
taatcttttc aacagcctgt aaggtaagta ttgttatccc tattttatag atgaagaaac  26220
tgaggcacag aaaagatata caatttgccc ggtacatagt tgtacagcta ggaagaggca  26280
gaactgggat tcacacttag tagtctggtt ccagatcctt gcttttaacc actggacatt  26340
caaattaatg ttttgtctct tagagatttt tttagacttt tacaatattt ccaatttttg  26400
tcttttaact tcaaagtttt taaaattcag ttttcattta tattgtcaaa tccattaaca  26460
ttttccaaat ggattctact ttagcgtcat ttagttgacc ttcaagggta aaaaatgaag  26520
cacagatagg aaggtaaagg gtaatgtatg tcatatgcac ttttgcaaac tcaccaagaa  26580
gtttccgatg aacatatgaa gaaaatgtca gaagggctca tagtgctata aggcttctta  26640
tttcttctaa aacacactgg cccaccagcc tctactacca acctctaatt gaggctcaca  26700
gtacctctta actctgatat ccaacaatat cctggtttat ttgctaatgc tttcttccca  26760
cctcagccta cttcatcatt attagatatc atttaatcct accctactgc tgtgctaggt  26820
acttggcata gacaggaaca aaacagtttc tgcccttgaa gagttccaca tcccctgcag  26880
cataaccaca ctcttcccct gaactgtact cgatctagct ctggggcctg ctctctcctt  26940
tctcaatata tcttctaacc tcaagaagtc ctccccaaat cctacccatg gcttaagctc  27000
aagtttcccc ccctctagtt tcttgttcac tttagctcac aaaataaagt ccccattaaa  27060
aacaaaacga aacaaactcc tttggcactt attgcataca ctaatatgag tgctaaaagg  27120
ggagctgata ccaccaccta agatcataaa tgtaaacgta cagcatgtca agtactattt  27180
cccatagttc tattacagac aaggacccac ttttttaaaa gtgttgcaca aagtcacaat  27240
gaattacaaa aagcagagct acagcccagg tcttgcggtt cccagccata aaatcttaaa  27300
actggcagag acctcaaacg acaccttaac tagtgatttc agagtcctag catgtgaaag  27360
ttgtaatggg gatggaggaa ctgggctttg gattaatttt aaaacaacaa aatcaaggat  27420
tgctttgaaa aacatttgaa gacaaaaatc ttcaaaacat gggttggaaa agataacaaa  27480
aaaaagctca gggaggctga ggtgggagga tctctagagt ccggatgtcg aggctacagt  27540
gagccgtgac ccacgccact gcactccagc cctggagaaa gagcgagaga ccgtgtctcg  27600
aaaaaacaaa caacaaaaaa accctcagac cccaaaacgt caaggaataa aagtaaaagg  27660
ttgggcggac acaactcctc catttgacag atgagcaaac tgaggcacag aactccagga  27720
ggcctggcca aggcctcctg gagggaacag ggtcagttga cggaaaagag ccagaggctg  27780
cacgctggac agcgttcgga ccttccgggt cgcgcacgtg taaattgccc ccaggagcct  27840
gagggagcaa agcagccgcc ccgccccgcg ggcagcgcgt tcagcggcca cgtgacacag  27900
ccagcccatc acgcgcaaag ggcagggcct ggaggacacc acccccgcca ctctctcagc  27960
cctccactag gaaagaagga gatggtattg gtgggcgggc cagacccgcc tcccccacgg  28020
tggccacccc gcgcgaggcg ggcccagccg ccgccctcca gtgaggggac ggacgagctc  28080
agctaggcca aggcgaaaga gcgacgcgca cttcaatcag acggcttcac caatgggctt  28140
gcgcgctttc cgcggcgccc gcccctgcat cggcctcccg gcgaccgcgc tgctttccct  28200
```

```
caggccgccg cggcggcgcc cgcccgcgcc tccatccggg tcctggcgcg gtgctctccc 28260
ggcagcgacg ggcgcgaggg ccggggcatt cccacggccg cgacggccct ctccgcgagc 28320
gcgaggtggg tatggcggac gcggcagcga gcgcgggtcc gtcgccattt tatttcgcgg 28380
agactcgcgg cagcgggtgg gcagaatggg agagccgtgc gccggcccgc gcctgtccgg 28440
ctaacgcggg ctgggactgg tggggcggcc tgccccctcc agcgggcggg tggccccggg 28500
gggccggcgg gctgctagcg gaagtcgcgg gcgctcgggg cacgggggag gggtgccgcg 28560
tggccgccgc ggggccggct ccaacccccct ccgcttcccg cccagctcct caccgacagg 28620
gcgggggagg gggggtcatt cttcacattc cttaccccgc ccttcccccc gcttcaatca 28680
aacttggggc gggcggaagg cccgccttcc ggccggcgcc tgttggccgg cgccgcctct 28740
gactgtggcg tgactggttg taggcgccgc caggtgcctc tgacgtcact tccgctatca 28800
agtttgtggg ccggggagac cttggccttg gggttggga tgaaggaggg aaggtaggaa 28860
gtgcgagggg cggggggaca gggcgggaag gcgcgggcgg ggagggcggg agagtcgtgg 28920
ctggctgcat gcccctgctc cccgcggcca agtgcagcct cccttcctga agcagctgct 28980
gcggctggag gtccgctgcg gcagccgtcc ttggcgaggg ggaggggaac gcgggagcgg 29040
gaggaaatcg tatcccgggg gacggggctt ggagatttgc gactcggtgt caccggaaac 29100
agcgctggcc ttttgagtcg acgctgcaaa ctcttggaac cgagtgcctc tcagaaggct 29160
tgctaataaa cttcccgggc gggctctagt gtgaggaatg tggtaacctg tatgtccttg 29220
gccagtaatg cccttcggtc tttcaacttt ttacagtaga ttctgtgtca gaggtaatgg 29280
tatgtattct tcaacttacc ggtttttaaa aaattgacta acgagagggc gggcagacag 29340
gaaaaaggca gggaagacag tgaatgttaa aattttgagg taaatcagga gactggttga 29400
gttttgcttt ttaacttcat tgataatact gctttcttgg catacagttc ctaaagttaa 29460
agcatcatgt ggcattcctt tgcatttatt tctgttggcc tgaagtataa gaacattgaa 29520
tgtcaaattc caaatttatg tgtagtttag gaaataattg tttatatcca gaattctttt 29580
ggtgtttggc ggggtctggt tttatttact gtatattcgg gaagtatgtg tagttaggga 29640
agtaaaaact tggaagttac tttgggtttt gtgagaatgt ttgattcatt atacatattt 29700
gttaaaagtt tactttgaaa cttcaacttt gagaatagac aaatttcttg acgtcctgta 29760
aattcagtgg tattatatag cattttaaaa tttatcactt aggtgcaatt acagtgtgag 29820
gggaaaagtt aacttttttg aatagttaca ttgcagtgac agcaagagag tatttttatg 29880
tgtagacagg ctgtgggttc ccctcactta aattgaagct ctgttgaact tgagacactt 29940
aagaatcttg caagtgtgaa aagtggagtg aaacaaaacc atttctaaaa cgaaaatgtg 30000
taactgcgtt cagttttaca cagtgaagaa ataagtatta aacaagttag tctcaaacgt 30060
ttatatctta aggtcatttt attcctgtta tcattaacta gacatatctt ggtttagaga 30120
gcagcacaca agacattgtg tacttttaat agctaagata gtataataac tactcatatg 30180
ggaattaccg agtgttaaga gcgccaaact agtgtttcaa actgtaggtc ctgagttata 30240
gggtcatgaa gtcactttag tgggtggtga tccgaatttt ttaaaaagta gaaaatattc 30300
cattgaatac aaaatagcgt gttgattcag ctcgacacat gtgtattcct gtaaaataat 30360
cctgtgaagc tgagtgtcaa aagttgaaaa acaacttctg tagggtgttt ttctcgttta 30420
tagcattgtg taaagtatta tagtttaata ttttttaacg agtattaaat gggctgttta 30480
tatttggtgg aacatgagcc acctacttta gtttcacaag ttgggaagta aatttgccat 30540
ccaggaccag tatgcgtttt aatcatagta tttttaatag cctgtgaagc ttttctttag 30600
```

```
accataagag gtcttttcca tcccataata tttattgcca attatttatc catgtctaga  30660
tgagactaga agaatccgaa tccccagtaa tgagttgtca gcattgctta atgtgacctc  30720
aggactgatc atcatatgct ttttgcctgt gtaggtgttc taagcgttgt ataatcactt  30780
aagaatggac ttcattaaat agacaaaata tgagagccat tacactattt ttggtattaa  30840
gtctttgaaa tccagactgt tttacacttg caacacatac acttggggct aatcacattt  30900
caggtgctca gtagcaacat gtgactaaca gctaccaaat gaacagtgca gttctagtgc  30960
actgttttta aaaaaattag attttttttt aaaattagat ttctctagct gaatagttgt  31020
agtttcagat aaacagccaa aaatgttctg tctctccaca gcttcatctc aattgtgaag  31080
aaattgcatt aggtgatttt tttttttttt tttttttaaa taatagaaac aacgtctcac  31140
tatgttgccc aggctggtct ccaactcctg agctcaagtg atccttcttc ctcagcctcc  31200
caaagtgcta agattacagg tgtgagccac cgggttcctg gccgaatcag gtgatttctt  31260
aggccctttc taaatacaag gtttaagtgt tttgaggcag ccgacagcta tacctttaag  31320
tctcttgctt ctctaagaat aagacatttt ggatcatttg ttctaccata acgtaatgaa  31380
tacaagttgg gagcattttg ctcttctgtt aagcacagtt ggccttcctg tccaaggatt  31440
tttgcatcct tgaattcaac taacctcaaa tggaaaatat ttgggggaaa aaaagtatgt  31500
acaacaaaaa taatatgatc aaaaataata cagtataacg actatttaca taacttttac  31560
attgtattag gtattgtaag taatctatgt aggaggatgt gtgtaggtta catgcaaata  31620
tgacaccaca ttttataagg gacttgagca tctgaggatt ttcctctggg agaaggaggt  31680
atcctggagg caatcccctg aggatacttt tctactttgt gtgaattttt cattaacagg  31740
aagttacagt acttttctgg tcacctgaga aacccacccc atatttttat tagccaaata  31800
tataattctc gaatgcttag aattcatttc ttaatgattt cactgttgtg cagtatagac  31860
tgtgaattgc ctactaagga tacagttaat tatagtaaac tgtggaatct agattaaata  31920
attacaccct actttttttc ttggcttgtg gatgtgtaga ctacatagtg gtttttttcaa  31980
cccaggaaca taacagtata atggaggata ggaaggcaga agatgtttaa agggttgaga  32040
aataatggta tatgtataat ggtcagtaag cagaacaagc cagccaagtt ggatattctt  32100
caagactatc ttaagtgtct gctatgtgtc taagtgaaag gaaataagca atagtccttt  32160
tgggaaacct gacctagtac ttagctattt cagacttaat gtgatgtttg atagagtagg  32220
aaataagatc ttaaattaga attaggttaa attgctttag agaaacttat ttataaatgt  32280
aaagaattta ttatctcatg tgttgcacat gctctatcga agggagcaaa atactattgg  32340
agagtttgct tattaatgta atactcagcc tgcatcattg tcggataatt ttgttgataa  32400
ttcaactatt tgagattgaa agaaatctgt taaagtagcc agtgttgtaa ttttgatctg  32460
tgtttgatta cagcgtatga aacaaaaatg agactggagg aaatagttta cttgtgaact  32520
ttttgagcta ctttgtttta ggagtattta aattaatgta aaagtgtagg gaaatgtctt  32580
agctcagaaa atttaaactt actagatatt aagtgcttaa aaggtagagt atgcttgcat  32640
ttcaactaaa gtttagagtg ttttaggaaa ttagaggcta ttttaaaaaa tattttgaag  32700
ttaggagtgt gttcctaagt gttttcacca taagaaaata agtctgtggg gatagtacat  32760
atgttaatta acttgattta gctataatat aaacctattt tatgtacacc ataaaaaataa  32820
caatttttat gtcaatttga aacaaattca ttacaaaaat gaaattagga atgtgaatgt  32880
taataagtta tgaaaactta cttgatgtaa atgtagatat agacaagtct ataactaata  32940
```

-continued

```
gatttgcctg ctttgtagca tgctttaaat tgataatatt tttaactatc acaagtatat  33000
ctggaaaggt aaaattcctg ttaggatagt ttgtcaaatt aatttattaa gtacagttgc  33060
catttgttga gttaatttct cagtcattca atatctttgc atgtatccca gtcctgacag  33120
caaccccatg aggtgtggct gttacagttc ccccaaatgg cgatgagaga acacagccac  33180
taagtagctg cttggctgct tgaccctgaa accattgccc ttaaccattt tcctgtactg  33240
gtatgctgag ctgaatgaaa tgaagataca ttttgtgtaa gttgaatttt gacttttagt  33300
tgccataaat taattaaata atttattatt gtatatattt ttttgagaca gttttgctct  33360
tcttgcccag gctggagtgt aatggtgcga tcttggtcta ctgcaacctc tgcctcctgg  33420
gttcaagcga ttctcctacc tcagcctcct gagtagctgg gattacaggt gcctaccacc  33480
atgcctggca aatttttgta tttttagtag agatgggttt tcaccatgtt ggccaggctg  33540
gtcccaaact cctgacctca ggtgatccac tcgcctgggc ctctcaaagt gctgggatta  33600
taggtgtgag ccactgtgcc tggccagttg ccgtaatata tatatatttt ttttgagacc  33660
gcatcttgct ctgttgccca ggctggagtg cggtggcatg atctcggctc catgcaacct  33720
ccaccttcca ggttcaagcg attcttctgc ctcagcctcc cgagtagcta ggactacagg  33780
cgcatgccac catgcctggc tgattttttt atttttagta gagagggggt ttcaccatat  33840
tggccaggct ggtttcgaac tcctgacctc atgatttgcc ctcctgggcc tcccaaagtg  33900
ctgggattac aggcatgagc cactgtgcct ggccatttgc cataactttt aatgagaggg  33960
tagttccagc tacagattga ggtagtatgt gaataaggat agaaagtgga tataaaagta  34020
tttttgttac tttttaagaa agaattatca gaaggctcaa attctgataa ttttagctaa  34080
tagtattcta cctaagaagt aaacaaaggc ccagaaatta gatgatatgt ccaaggacat  34140
agtaaatggg gagccagcat taactgtaga cagaaaaact tcaagtccta aatgtatact  34200
agctatcaac ccactctttc ccagtacgca agcattacat agttgtgatt agttagttag  34260
ggcttttaat taacttccaa atgaatattt ccatgggttc ttgtaatcca taaattcatg  34320
gattatgttc agtgtttatg agagctggcc ctaactgaac attgctcggc tgtttggttt  34380
tagtttccac catttgctgt aatcagtgtt ttctaaactg caggctggga accattagat  34440
tataaaatca gttcatgtat ataataaaat aacatattag agtaagtatt gatttgtgaa  34500
caatattatt tattggatta cttatataca tatacttttc aaaaaattga gggtcatgtt  34560
aatagcactt ggtatgtaaa ttaccagaat gctttctagc aatatggtat ttatttacat  34620
agctggattg agaaagaata atacaaagta agcatgtgac accaaggttg gaaaaaaaat  34680
gtgtttttga atgtttgatg aggattcaaa catgttttaa atgagaaaat cggtaggagg  34740
ttgaggattg tagtagaagt accagatgct ttttctttta gctgtttttt ttcgttgctg  34800
ttgtttggtt ggttttggtt ttggtttttt tttttttttt tttggctgtt attgttttaa  34860
aagtaaggac taggccgggt gcagtggctc acgcctgtaa tcccagcact ttgagaggcg  34920
aaggcaggca ggcaggcaga tcacctgagg tcaggagttc gagaccagcc tggccaacat  34980
ggtgaaaccc cgtctttact aaaaatacaa aaatgagctg ggcgtgatgg tggatgccta  35040
taatcccagc tacttggggg gctgaggcag gaaaatcgct tgaacccagg aggcggaggt  35100
ttcaggagcc aagatcacac ggttgcactc cagcctgggt gacagagcaa gacctcgtct  35160
ctaaaaaaat aaaagtaagg acagtgctga ttcatgggaa atattttggc ttataaaggg  35220
cctgacgtta gggacaagtg tgtctgtgag ttcctagttt gcataacctg gccttgtaga  35280
attgaaatgg tctcaaatgt agtatagttt agtgatgcag tactgtctct aatttggggc  35340
```

-continued

```
aagttattaa gcttcttacc accagttttc atctagagat gatgaagtag ttggacctta  35400
catattttgg atatatggta ttaataaatc tttccctttt tgttacagac gtgttgatac  35460
tgcagctagg aaagctgagg gacttcggct aaatttcttt tgcaagattt caatggcaga  35520
gaattagtag ggccaggatt tgaaccctgg tttttattga ctccaaatga gtaatgctgt  35580
gaacattcaa atacacgttt tttcaattct cttgcccttt ttttttgcgg ggaggggcag  35640
ggtctcactc tcttgctctg actggagtgc agtggtgtgg tcatagctta ctgcaacctt  35700
taactcctag gctcaagcaa tcttcctgcc tcaacctcct gagtaactca gctgggacca  35760
taagcctgca ccaccacacc cagccatgtt cagttctcta gagtatatac ctagaaatgg  35820
aattgctggg tcatatggtg aactgttttt tactcatcac taaccagttc tgacaccaac  35880
aatcaattct tcaactcgac accaacagag tgtcctacaa ttaaatttaa ttctgaaact  35940
acctgaagtt agtacaaact tcacaggttg agggctcaaa cacgtaagac tgccccccgct  36000
tcagatgcag gtttctacct gaatttttaa ccaaccagct ataaattagg gggtttcaca  36060
acctcttcca ctgggtctat aatttgctag gatggcttac agaacacagg aagacactca  36120
ttatcactgg tttattataa aggatttaaa tgaatagcca gatgaagagg tccttaagct  36180
gaagtccagg agggttccta gcacaggagc ttctgtatct atggagttag ggttacacca  36240
gcctcctggc atgaagatgt gtttttcaac tcagagctgt ccaaaccctg acacttaagg  36300
ggtttttatg gaggtttcat acttaggcat gattgattac attattggcc tttgatgatt  36360
ggcttactct ctgtcctctc tgctttacct ggaggttgag ggggtgaggc tgaaagttcc  36420
acccctctaa tcacaccttg gtctttctgg tgactatccc cctcctgaaa ctacaggagc  36480
caccaatcga ctcagtagca ttaaacagac attcatcact taggaaattc tgagggtttt  36540
aggagctgta tgccagccag gatcttcaaa tggagacaaa gacgaaatac gtgtttctga  36600
ttccacttaa caactgtttg acttgtctac aagttttgtt ctccaaagca gctgcaccat  36660
ttcacattcc caccagcaat ctaagggttc caattttctc cgcatccttg tcaacacttt  36720
tattaatctt attagccatc ctaatgaata atgtatcttt tcatgtgcct gttggccatt  36780
tgtgcttatg agtcatatct ttggtgaaat atctattaaa atattttacc attaaattag  36840
gttgttttaa gttactttaa tgtgtgtttt gcacaccagt ttacaaagaa tgcagatcca  36900
ttttttttgc atgtggctat acagccgtca gcattatttg ttgaaaaaac gattcccagt  36960
tgaattgtct tgtcatggtt gaaaatcagt tgacccatgt atgggtttat ttctagactt  37020
taaattctat tatattgagc cgtatgtttt ttattacgtt ttgtaatttt aaaaattagt  37080
gcttttggtt actaaatcac tacaaaataa atttagtccc tatcttaaaa gataatcttc  37140
gtagtagcta cctcctaaat atgaagtctg taaattaaag ggtaataata cagtttagat  37200
tacttgggtt tattaaagat tttggactct gccttcaatc cacatattac ctttctatct  37260
aaaggaaagg atcctgaccc tgaatcagat ccaggtgatt atctttgatt tagtcctaat  37320
aagaccactt agtgtttgct cgcatgggat aaatgagtag gttcctttaa aaattagttt  37380
ctatttgtgt gtgtttttta tattatctcg ttgtatgtta gtgcatttgg attatgcatg  37440
atgtacagga cttttgggtt ttgaagtcat tggattttta attagaggct gtcatgtttt  37500
tctgtaatga ttttttgttg tttcttgaag gataagttat ttcatgcatt ttcatttgta  37560
ggaactgtaa gaaaaccagc agttaataat agtaaaaggt ggtggtaaga gggtgatttc  37620
tgaatcttgt aaatacatgg ttttaggagc ggattcagat aaccaagcat ttaaaatact  37680
```

```
attaatgaaa tacaggaaat gaaaccacag catagattat gcatgtagcc aaaatgttca  37740
gttaaacttc attttcaacg taagtgaatg aaaatggtct aatactattt ttcttatcac  37800
tcacacagga aaccaggatt accgaggagg aaaaaaagcc ttcctgtggt gctcaactgt  37860
gattcctttt caccattcac cctggatgtt ctcttcactg tgggatgagg tagtaggttg  37920
tatagtttta gggtcacacc caccactggg agataactat acaatctact gtctttccta  37980
acgtgataga aaagtctgca tccaggcggt ctgatagaaa gtcagttaac taattgtaca  38040
atatttaaga ttaacttgtc ttaaagagat gtagtgcagc atttgtttat ggcctggaaa  38100
taaattaatt tagagataaa gtctgtagca agtacactgg atgggggtgg ggaaaccttt  38160
tgcttcttgt cttatttctc tgtgtcagaa taaatgtatt tttttatttt gatttatgct  38220
gataatttta tgttgaaatt ttctttcgaa agagattgta ctttccattc cagaagaaaa  38280
cattgctcta tcagagtgag gtagtagatt gtatagttgt ggggtagtga ttttaccctg  38340
ttcaggagat aactatacaa tctattgcct tccctgagga gtagacttgc tgcattattt  38400
tctttttatt tagatgatat taaaactcag aagaattaat tttgacattt tgtatttaca  38460
gtttatcagt taattttctc tgttcaagta gtacagtagg cacagattaa catttaaatt  38520
tttcacatat ggtatatttc agaaatttga agttaagcaa aaattttaat gagtagagaa  38580
agtaagtagc cttcaggaaa tcttcataga ggaccaggcc cttttggaat tgtgaatagg  38640
tttattgcct tacatcctgg tacacatgtc caaggtcagg tcctgggtgg taaaggtaaa  38700
tacaaattgg aagggcactg tgtgagccaa aatgagtcag attagtcatg attcatttcc  38760
agtttgggtt ttgggtggtc ttggagaatg ttgtaagcac tgcttcattg ataggttgat  38820
tgagccagac tttactcagc agcctggaaa aggagagatg ggctctgggt tctacctttg  38880
ctcactggta agttgctaag atttcagctt tgccctcaaa ccctgaagta gtccttcatt  38940
cacacagtgg gatcactcga aaatgtcaga tggggaagtc cataggttgt tactttaaag  39000
aaaatagaaa aaatgctgga aaaggtttct tcaattttaa tacccatgaa ggcccatgtt  39060
ttagctttcc tccgatgggc aaaccataca ctaacttggg ccttgtaatc aacaagcaag  39120
gctaaaagct ctctaagtgc ttgctgttta aactattttg tgttggaaga agagttggaa  39180
aagaggcagt gtggaggtga gggagaagtt ccctccctcc aatcatttcc aataaatgga  39240
aatttaagga gaaatttgtg tttatcctta atatctaaga taatcactgt gcagtgccat  39300
tggtactttt catgagagta gaaacatcaa acttccttgg atgggcccaa cccaggtgac  39360
ttaactctgg accaaatgta tgctttttgt tttatccact gtggacagct gcatagataa  39420
ttggtctttg ttctaaactg cacataaaaa catgggagaa aatgacattt gttgcctttt  39480
gatgtgccaa agaagagtgg gaatgttcta agaattcttt ttggcttaat ctttgttgaa  39540
ttgaaaatat gtataactct tctgctgaaa gtgtagcaag tacagtcatg aaattttgtg  39600
gtcttcctga catgttcttc cagcataacg ttgccacctt cagttggaaa cgtatcctta  39660
tctaataatt aagccctgga gaaaaattaa tttatatatt ttattaatta cataaggaca  39720
ttgttattag ctaagcagag taagtaaatc gaaataaaac tttaaaaatg cctttatgga  39780
gagaatgact atctctgaaa gcttgttttt aatgatgata aaattcatga tcagaatttg  39840
tttctgtttg ctttaattca ggggtcaaaa actgaaatac catcagaggc ccaggagggg  39900
ctagttgtaa ctggcaaata tagtaaatta atttgctctg gttgataggt agcaagcagg  39960
gtttatatac attgtcacct acttttccag ttaacaggag agactggaga ttttatgaaa  40020
tttgatattt aaatgttggt aactgggttg ggcaccatgg ctcacacctc taatcccagc  40080
```

```
acttcgggag gctgaggcgg gtggagcacc tgaggtcagg agttaaagac catcctgacc  40140
agcctggtga aacacagtct ctaataaaga tacaaaaatt aggccgggtg tggtggctca  40200
tgccggtaat cccagcactt tggggaggcc aaggtgggcg gatcacctga gtcaggagtt  40260
tgagaccagc ctgcctaaat ggtgaaaacc tgtttctact aaaaatacaa aaaagtagct  40320
gggcgtggtg gtgggcgcct gtaatcccag ctactctggg ggctgaggca ggagaatcac  40380
ttaaacccag gaggcagagg ttgcagtgag ccgagatcac accactgtac tccagcctgg  40440
gtgacagagc gagactgtcc aaaaaaaaaa ttgataatta aatgttaaaa gtcagcgact  40500
ccagtaatac gtggtgggct gagtattaga ctactggctt acatcctctg atgtcattac  40560
tttcttgttc gtttgtgact tgaggttgga ttttaagcaa atgtatttgt ggctttttac  40620
caaggtcata tggccagata acttttcaaa agcattagtt aaagaattct gattagtttg  40680
aattagaaac aaaactcaaa gaacatgacc taatttaaca ggttaatttg aagtgcatct  40740
gccaagtaga agaccagcaa gaaaaaaaaa atgggttcct aggaagaggt agtaggttgc  40800
atagttttag ggcagggatt ttgcccacaa ggaggtaact atacgacctg ctgcctttct  40860
tagggcctta ttattcaccg ataacctgtt tccttgctac tttgctttgg tgtaagcaga  40920
gttctttctg taggtttttt caaatgaaaa cattgcaaga atatcaaaga gagcagtgtt  40980
tgcgttagtg attataaact gcagcatggt gctgacattg ataactgaaa gtcaactaat  41040
gagaatttga gacttctgaa gtacacttag ttgctagtgt ctcccttttg gtgtcactgg  41100
aaagtttaga aagcatggtt ttgtttttgc tcaggtttct ctttctgtga tgcagagact  41160
ctcagctgtt cctcctctat gtctacatta tgtctgaagg aaagaattta acaaaacttg  41220
aaatactgct gtttttctac aatgtttgta aatatttatc ttgctgcttt tctaggtttg  41280
tcttctggat ttaaaatttg gggcggctgg ggtggaattg catggtttgg gaatgggtaa  41340
ttgagctgct gctcattatg gtatgtaaca gtgatttgtc tgtttaatat gtacaagaac  41400
tggaaggtca ataaaatgaa agtggttgtc ttgactgggt aatagtgtta catattttgt  41460
taaaagttat acatcttttc aataaaaaca ctgcatactt caaaactagt gctttttaag  41520
tcatccttaa cccttatccc catccttgca gtagtagatg catttttcat ttgtaattat  41580
tatgatttgt tcttagtttc atttttcatt agcaataatt tggtgattgg atggtcattt  41640
acagatgttt taataaagct aacacgagca atttccagct cttccatttt tgtaaacact  41700
tgtgtgactt tgtacagaca attaactgct caggatcacc ctccttttg ttttgtttt  41760
gagatggtct cattccgtca cccatgctgg agtgtagtga aatgatcaca gctcactgca  41820
gccttgacct cccggactca agcttcctag taactgggac tacaggtgca tacaaccatg  41880
cctggctaat tttatttttg tagagacggt ttcaccatat tgcccagact ggtcttgaac  41940
tcctgattat cctctggctt ttacctccca aagtgctggc caggacagcc tcctttcttt  42000
acttgagtaa ttatttgagt ttgctcaggc agacactacc ttgtaaaaac tcttatgtct  42060
catttcacta gtctagtttg agcatttatc attctaggaa tgagacgaat ttgtgcatta  42120
gcattccatc tttttccaac tactatgaac agtagtattt ttttttattt tattttattt  42180
tttgagacaa aatctcactg tttcccaggc tagagtgcag tggtgtgatc tcagctcact  42240
gctgcaacct ccacctcctg ggtagagtag acaggattta ggtaattttt tgtattttta  42300
ttagagacag ggtttcacta tgttggccag gctggtcttg aactcctggc ctcaagtgat  42360
ccaccggccg tggccttcca gagtgctggg attacaggtg tgaaccaccc ttgcctgatc  42420
```

```
atgagcagta atacatttaa aagtctccag gggtgagaaa gttgaaagga aattcagtgg  42480
agtttcccat cctgcccctc tgctgcctag ccccttgctc cagtggaagg aagaatcgtg  42540
atctagggat gttctcatac ttggggcttt aaatttcctt tatgaattga gatggttggg  42600
tatgttttct aaggtacctt acatggtaca gttctttaaa gttgaagatt taagttgtgg  42660
caaaattgca tcaatttcat gtgcactgat ttaggcgaag atgcgtagga aaagagcaag  42720
gaaatgaggt gtgataggat tggggtaatt tcaaaatgag tatttctgcc tggcctagtg  42780
gttcacgcct gtaatcacag cactttggga ggccaaggca ggcagatccc ctgaggtcaa  42840
gagttcgaga ccagcctggc caacatgatg aaaccccatc ttactaaaaa aaagtagctg  42900
gcatggtggt gggctacttg tgaggctgat gtaaggagaa ccgcttgaac cagggaggtg  42960
gaggttgcag tgaccagaga ttacgctatt gcactccagc ttggacgaca gagcaagact  43020
gtcttaaaaa tgtttctagt ttcacttatt ctaaatttat gtctaaccat ttttagtgaa  43080
gtatttgagt cacatcagct agccttttc ctacagcgtt gaagtaattt tctaggttcc  43140
ttgctctccc cccatttat ttcctacttt gctttctgtt gttggggtcc tatggggagg  43200
gctgggaaag gagttgggcc ctcttaggac tggtcatcaa tctttgttct gagcagtgtt  43260
ttgttttctg gttgaatggc tgacctgaag gaagcatcag actccttggg attctgaaat  43320
cctatttctt gatagaaacc cataacttat tttagtttga cttaaaaacg atccataagt  43380
aagcatgcag ggttggtgta actgcattga actggtaaca tcagaaacac gggtagaaat  43440
gaggtacccc agtgatacgg aagctttgtg actgatgtcc tggattcttt ctagcttttc  43500
ttccagccct aacacatggt ttccattctc aaggttacct ctgtaacaac tgactgctat  43560
aactggccac gtcgttttc cattcatgaa gatggaaaaa ggaaaaggca gaagggacac  43620
ttttatggtt gaattcattt agttttctca agaaatgcca cctagtgact cctttacgtg  43680
taatcccttg gaactatcac agactagacc aaggaatcct ggaaagtggt cctggcagga  43740
ctgattgcca ggctgaatac aatcagggtc ccactagtaa ggaggggaga aaggaaataa  43800
cacagatagt tatctgcagt aattggcatt aggaaaaaaa acttgacaaa gactgacaag  43860
ctctgttcca ctcctgccat ttaaagaaaa acacacacac gcataaaaac accaagtggc  43920
ctcagatggg cagcactcct cctgaccctg ggcttcagaa attttcactg ggagtctgat  43980
gaggctcagc cacagttgtg tgggactgtt ctcaatttca agcagaggag cagagaaagc  44040
tggttagttg cggaggcttc ccacattact tggaccctac aatatatatg acttctatca  44100
caggacatgg tacagaactg gaacaataaa gcatttttta aaatttaatt tcttgagcaa  44160
ttttagtttc acagcaaaat tgagcagaaa gtatagtgtt cacatatact tccctgttta  44220
ttacgcacac actgccttcc tcactactga agtcctgacc ataatggtac attttaataa  44280
agcagtttgt ttttcccttt tctttgaagt tgttccatca tgagaattag gctaaaagtc  44340
ttagcttact gccccatgga aggaaggaca aatagcaatg accaagcaac gtatttttag  44400
ctttgaggcc aaaattggct gaaaatgaca gaagcagtta cttcagagaa aatgattttt  44460
tgcagttctg cataaatttg aagaggtaaa cctggattgc tgagaacaat gagttatatg  44520
cagtggacta gaggaagatg catattcaac catgtctttt tttccatcca agaagagtta  44580
ctagcaagca gtaagatgag aggaaatgaa accagtcaga ctgctgagtg ctggagaagc  44640
ggtccctgtg cacactccgg catgggcatg gtaggactac ctgtatggat taaggggagt  44700
caagggtcag gggatggttg atctgcattt ttttccccag ggcataacct gagaccacaa  44760
agcttctagg gaagggttgt gtacatcatg gccccacagc agtgagaggc ttgaagaatg  44820
```

```
ctctggctaa agacacggag gtgctgtggc aggcactgtt acttgcctac ccaaatatcc  44880
ccttgctggg agaaccttga ttttgttgag gtatggatct caggaaagtt accctagttt  44940
tttgtctagg ggtaggcatg tgaccagatt tgatcagtga gatgtaaaga ccagtggtag  45000
ggagagggtt tctttctttt cttctccctc ccccgaccca ccccagagtc tcgctttgtc  45060
acccaggctg aaatgcaggg gcgtggtcac ggctcactgc tgccttgacc tccccaactc  45120
aagcggtcct cctacctcag cttcccacat aacttggact ttacgcgcac accgccatgc  45180
ctggctaatt tttttctgtt ttacagacgg agtcttgcta tgttgcccag gctggtcttg  45240
aactccgggg ctcagacagt cctcccacct tgggctccca gagtgctggg attactgctg  45300
tgagccactg cacctgcctg catcatgctt aggtttgaat gtggttgtgt gatgatcaga  45360
gctgctgcag ccatcttgtg accacgaagg gtaggttagg tcaataatac caaccaagag  45420
ttctgacatt actgagctgt tgagtcaatg ccagcatctg ctctcctcta cactttgtat  45480
tatatgagaa aaatgaacta ccttatagtg aatggggggtt atgagacttg cagggaaaag  45540
ctctcctcac aggatcccac atagggaagt ccagggaaag cccctaaatg tgagggaaga  45600
ggaaaggtgc taaggggcca tcaggaagaa gcctatggct tagataagga tggtagacaa  45660
tggatctctg acatctgtag caggaccctg aacgtgagca tgaacatgaa gtggtaagag  45720
gctgatggca agaccacatt tctgaaactg ggatcttaca agtggcaggc agcaaggacc  45780
aagctcaaga cagtatggac caaacagtaa ggacacccct tcttagtgct gacatgagtt  45840
aagccctttg gaaatttaga tcctcttgaa tttgataaac taactctcct aaaaactgct  45900
ttaaatcgag acagttctct taaatggatg aaatttcagt gttctgccat tagtagacat  45960
gggggctcaa gatactcggc aacaaaagtt tttgttacat ttttgctctc ttgaatggca  46020
actgtaaact ttgaacctct gcagttaccc taatgcagaa cttattattt atagactttt  46080
tgatgattta caatgaaata ctgatataga aacagatgtt taaaagaaaa ctgtatagct  46140
tgtctcactt aagtaacgta gcctaagttt cttaaaccca agatctcatt ttagctacct  46200
aggtatattg tccagagtac tgaatatgag cacatttcac atgacaggct cttaaatgca  46260
agtgtgtgtg cgtgtatgtg tctgtggtgt gtgtgtgtgt gtgtgtagtc cttgcattgc  46320
ctggcatctt gttacagtaa ttcatgcaca taagaaccat gtccttgctt tgccttgcct  46380
ggtagagaac tatgcaaagc aagaacaagg ctccagtatg aacaagtttg tattagcatg  46440
gtatcatgaa atgtaagaac tccctgtgta tgctgtatgt accctttcct tcttaaaata  46500
tgcccagcac ccttctatgt ctttgtcttc tcattagtct tggaaatact ggtcataggt  46560
cctcatgggg aactaacttc tctaagcttt caggttgtat catccagccc attggcagct  46620
acttaggaag ctttttatac tctaccctga agtgtggtgt tttaactagg tctgaaagca  46680
gaggagtgac ccagtagagg gtcactgacc aaaatgagaa atgaggtggt tgagaaaatc  46740
tgaaaagatg cacaaggttt caggtataat acatttgtct aatatctccc aagattgcaa  46800
ataagtttcc ctaagtagtc ttatgattat tttattatct tgggcacttc agtatagggg  46860
aaagaagggc agagtatggt gaatggcaga gcagaagatg cctaaatagt tgggaaaaat  46920
aatcctgtga ctggaaaact gcattaaaaa taatatctgg ccaggcgcgg tggctcacgc  46980
ctgtaatccc agcactttgg gaggctgagg cagacggatc acgaggtcag gagatcaaga  47040
ccatcctggc taacatggtg aaaccccatc tctactaaaa atacaaaaca aattagccgg  47100
gcatggtgat gggtgcctgt ggtcccagct actcgggagg ctaaggcagg agaatggtgt  47160
```

```
gaacccggga ggcggagctt gcagtaagcc gagatcatac cactgcactc cagcctgggt  47220
gacagagtga gactccatct caaaaaataa taataataat aatatcttgt tgatacatcc  47280
ttcttttgtg attgggggaa atggtgactt aatccctaaa ggaatcatgt aatatgtaga  47340
cctttgaata tggctttttt catttagcct gtttttaagg ttcattcttg ttgtgatata  47400
tatattttg aaataggttc tcactctgtt ttccaggctg gagtgcagca ttgtgatctt  47460
gactcactgc agtgtcgacc tcctgagctc aactgtttct ttatatttct gagtagtatt  47520
ttcttgtata gatatcaaat cttctttatc ttcttttttt tttttttttt tttttttttt  47580
agacagagtc tcgctctgca cacccaggct ggagtgcagt ggtgctatct cggctcactg  47640
taagctctgc cacccgagtt cacgccattc ttctgcctca gcctcccgag tagctgggac  47700
tacaggcgtc cgccaccacg cccagctact tttttgtatt tttagtagag gcagggtttc  47760
accatgttag cagggatggt ctcgatctcc tgacctggtg atacgcccac ctcggcctcc  47820
caaagtgctg ggattacagg cgtgagccac cgcacctggc cttttttttt ttaattttaa  47880
tttttttttt ttttatgttt ttgagatgga gtctcactct gtctcccaga ctggagtgcg  47940
gtggcatgat tttggctcac tgcagcctcc actttccagg ttcaagccat tctcctgcct  48000
cagcctctgg aataggtggg attacaggcg cttgccacca cgcctggcta tttttatgtt  48060
tttagtagaa acggggtttc cacatgttgg ccaggctgag gtcaaactcc tgacctcagg  48120
tgatccacct gccttggcct ttcaaagtgc tgggattaca ggcgtgagcc accacaccgg  48180
ccttgtttat cctttcacca gttggtgggt atttggattc ttttttttcta gctttggttc  48240
ttatgattaa tgctgctaca cagcattaat gtccacaatt ctttctgtgg acatctgttt  48300
tcagttctct gggagaaata cctaggagtg gaattgctga gttgcatggt aaatttaacc  48360
ttctaggaaa ctgtcagacc gtcaaactat tcaattgttt cagcaccatt tgttgagaag  48420
actgtctttt tttagtcgaa ttggcctgac accttaattg aaaattaatt cactatatat  48480
aggtggcctt attgcttgac ctctattctg tttcattaat ctatatatct atctttatgc  48540
tagtaccaca ctgttttggt tactgtggct ttataaagtt ttgaaatgag tagtataagt  48600
cctccagtgt tgttcttttt caaaattgtt tttgctactc taagttacat gcatttctat  48660
gtaaacttta caatcagcct gtaagtttct taaaaatctt ggattttgac ggggatagct  48720
aattgataac aatgctgagt tttcctgtcc acgaacctgg aatgatctct ccatttcttt  48780
agatctataa tttgagcagt gttctggagt tttcagtata taagtcttac acttctttta  48840
ttaaatttat tcctgttaca ttcttttttt tttttttttt ttttgagacg gggtcttgtt  48900
cttttgccca ggctggagta cagtggctat tcacaggtgt gatcatagtg tactataacc  48960
tcgactcctg tgctcaagtg atcctcctgc cccatcctcc acatagcagg gactacaagt  49020
gtttgccact gtgtgcagct ctttattgtt tttgataata ttgtgaacat attgttttct  49080
taatttgata ttcagattgt tcattgctaa atacagttga cattcatata ctgatctgtg  49140
tcttgtcacc ttattgaact catttattag ttctggtagt atttgggggg attgtttagg  49200
gtttactaca atttggatca tgtcatctgt gaataaagac agttttacta tttcttatca  49260
atctggatgc aatttctctt ccttctcctt aaaaaattgc cttattccat tagttagaat  49320
cttcattaca ttattgaata gaagtggtaa gaagaggtat cttactttgt tttatgctgc  49380
tataataaaa taccacagac tggctaattt atgaaggaca gaaatttgtt tctcgcagta  49440
ttgaagactg ggaagtccaa gatcaaagca ccagcatctt gtgtgggtct tgctgcatcc  49500
tcacatagtg gaaggtggaa ggagaagaga gagcaaatcc actcccacaa accctttta  49560
```

```
tagggtcatt aattcattca tgatggtgga gctctctcat gactaaacac ctactctaga  49620
attgctattg gaatttcttt ttatattttc tatctatgta ttgatattct ctatttgttt  49680
atatattata ttcttggttc tctctagttc tttgttcttg gtttccttca gctctttgag  49740
catatttagg acaggtgatt taaagccttt tatattaagt ctgggcttcc tcaaggatgg  49800
tttctattaa tttctttact cctgttggct agccatactt tcctgtttct ttgtatgcca  49860
tacaattttt ttcttaaaaa tgggatattt gggctgggta tggtggctca cgcctgcaat  49920
cccagcacat tgggaggcca aggcaggcag atcacttgag gtcaggagtt caagaccagt  49980
caggccaaca tggtgaaacc cgcctctact aaaaatacaa aaattagcca ggtgtggtgg  50040
ggtgtgcctg taatcccagc tatatgggag gctgaggtaa agagaaagta ggcttgaacc  50100
tgggaggcgg aggttgcagc gagccaagat cacaccattg gactccagcc tgggcaacag  50160
agtgagactc catctcaaaa atatataaat aaataaaata aaataaaata aaataaaggg  50220
ggatatttgg aatattataa tgtgaaaagc tgattctccc acctccccag tgtttgctgt  50280
tgttgattgt aggtgtttgc catcatccat ttgtttagtg acttttccaa attatatttg  50340
caaatactat attccttgtc ttgtgtggtc actgaagtct cttctcttat tttagcagtc  50400
agttatttca cagagatgtg ccttaatggc tggggccaaa aagaaaccaa aaccaaaaaa  50460
ctctcctagt ctttgcagat tggatctgag ctgagggatt ccttcaatgc ttagccaggc  50520
tatctatgac tgtgacttag tctttacctc ctacttgcac agagtccaaa aatcagccaa  50580
aggtgcaagc ctagggttct atcattcttt ttttatgagc atgttcccag cctcatgcat  50640
gcatattgca ctctgggttc tccagtatac gcagtagccc ttcaaaacca ttaattccca  50700
agaaacttct gcctcagctt tcttctttcc agatgtttga ttctatatac cacccaccag  50760
ctcctgcccc atccaccaca ccttgatcca gacagctatg tgtagtatat gtctgaatgc  50820
ttttgacaga tgtcacctgg aaagccactc taggctgaag ggttgtaaa agagcttatc  50880
ctatgcacca gtcccttagg gaattgtcag gtcaaaactc agagccaggc cgggcgtggt  50940
ggctcacgcc tgtattccca gcactttggg aggctgaggt gggcggatca cgaggccagg  51000
agatcgagac catcctggct aacacggtga aaccccatct ctactaaaaa tacaaaaaaa  51060
ttagccaagt gtggtggcgg gtgcctgtag tcccagctac ttgggaggct aaggcaggag  51120
aatggcatga acccaggagg tggaggttgc agtgagctga gatggcacca ctgcactcca  51180
gcctgggtga cagagcaaga tactgtctca aaaaaaaaat aaataaataa ataactcaga  51240
gccataattt ttgggaaaca tggttattgg catcagaaag ccacactagg aatgcagatc  51300
cctgttccca ttgctattgg tgacctggga aatggaattg ataagaaagg aagcaaaaaa  51360
attttttttc gttaagcact tcactggttg ccgccagttt tgtattagaa tccagagttt  51420
gaaaaagttg attctgtcag attttgccag cttaatggat gcttcagtgg agggactgga  51480
ctgattattg gaactcccta ctccatcatt tatgtggcat cacctaactg cttttgcttg  51540
ccttagaact tccagcacag atacgaaaaa aaatggtgag agaagacatc cttgccttgt  51600
tcttacatgg aagacattga gtctttcact gttaggtatg ttagctatag ttattttaa  51660
gaaaatcttt atcaagttta ggaaatttcc cactattgct agttttttga gagttcttat  51720
gaatgctatg aattttgtca aatgattttc tgtatttatt agtatagtca tgatcatatg  51780
atttttaaaa tatatatttt gaaatttctt ttttgtcttt tatctttgtt tttatgttat  51840
tccaatgaat ttttaaaatt tcaatagctt tgggggtaca aatggttttt ggttgcatag  51900
```

-continued

```
atgaattata tagtggtaaa gaaagtctga gattttagtg cccttatcac ctgagtagtg  51960
tacgttgtac ccaatatgta gattgttatt tctcaccctc cactcccctc ctgcttctca  52020
ttttccatag tccattatat cactctgtat gcctttatgt acccacttat accatacgtt  52080
gtcacttaca agcttagttc tcacttataa gtgacaacat atgatatttt gtttttcatt  52140
cctgagttac ttcacttaaa ataatggcca ccagctccat ccatgttgtt gcaaaagaca  52200
ttaatttgtt cttctttgtg gctgagtagt attccatggt atacatatac cacattttct  52260
ttatccgctt attggtcgat gggcgcttaa gttggttcca tatctttgca actgtgaatt  52320
atgctgcaat aaacatacct gtgcaggtgt ccttttgata taattacttc ttttcctttg  52380
agtagatacc cagtagtgag attgctggat caaatggtag atctactctt aatttttttg  52440
gaaatcttca aacttttcca tagagatggt actaatttgc attcccacct gcagggtatg  52500
aaagtgtttt ttcaccacat ccacaccaac atatattgtt gtttagcttt ttaaatagcc  52560
gttattgcag gagtagggtg gctttacttt gcatttccct gatgattagt gatgttgagc  52620
atctttacat acatttttttg gccatttgta tatcttctgt tgagaaatgt ctgttcatgt  52680
catttgccca ctttttgatg ggatgatttg taggtgtttt tttcctgctg atttgcttga  52740
gtttttttgta gattctggat attaggccat tgtcaaatgt atgctttaca aatatttttct  52800
cccattctct gggttgtctg tttactctga tgattatttc ttttgctgca cagaagtttt  52860
ttagtttaat tagattccat ttatttattt ttgttttgtt acatttgctt tgggggtctt  52920
agtcatgaat tacttgccta ggccaatatc caaaagagtt tttcctaggt tatcttccag  52980
aatttgtatg gttttgggtc ttagatgtaa gtcttccatc catcttgagt tgatttttgt  53040
gtaaggttag aaatggggat ccagtttcat tcttctacat gtggctagcc agtttcccag  53100
caccatgtat taaatagggt gtccatttgc caatttatgt ttttgtatgt tttgtcaagg  53160
atcatttggc tctatgtatt tggctttacc tctgggttct ctactcagtt ccattggtct  53220
acatgcctac tgttatacca gaactatgct gttttggtac tgtattagtc tgtttttgca  53280
ctgctgtaaa gaaataccca agaccgggta atttataaag aaaagaggtt taattggctc  53340
atggttctat aggctgtaca ggaagcatag cggcttctgc ttcttgggag gcctcaggaa  53400
acttacaatc atggtgaaag gcaaaaggga agtaggcaca tcttacgtgg ccagagaagg  53460
agtgagagag agaggtggga ggtgctacac tttttttttt ttttggagac ggagtttcac  53520
tctttttgcc caggctggag tgcaatggca ccatcttagc tcactgcaac ctccgcctcc  53580
caagttcaag cgattctcct gcctcagcct cccaagtagc tgcgattaca ggcgcccacc  53640
accatgcaca gctaattttt ttgtatcttt agtagagatg gagtttcacc atgttggccg  53700
ggctggtctc aaactcctga cctcaggtga tccacccact tcggcctctc aaagtgctgg  53760
gattttcaca tggggcatga gacaccacgc ccagccggca ctacacgctt taaaaacaac  53820
cagatcttgt gataacttac tcactgtcat gagaacagca ccgaagggat ggtgctaaac  53880
cattcatgag gactccaccc ccatgatcca gtcacttccc accaggcccc acctccaaca  53940
ctggggatta caatttgaca tgaaatttgg tggggagaca gatccaaacc acatcagtaa  54000
ctatagcctt gtagtataat ttgaagtctg gtaatgtgat gcctccagat ttgttctttt  54060
tcttaggatt gctttggtta ttcaggctct tttttggttc catatgaatt ataggatgtt  54120
ttctttaatt ctgtgaaaaa taatgtttgc attttgatag gaattgcatt gaatctgtag  54180
attgctttgg gcagtatggt cattttcaca atattgattc ttccaatcca tgagcatggg  54240
atgtgtttac atttgtttgt gtcatctatg atttctttca gcagggtttt gtagctctcc  54300
```

```
ttgtatagct ctttcacctc cttggttaag tatattccta ggttggtttt ttgtttattt  54360
gtttgttttg cagctgtgat aaaaagggat tgagctccta attggattct cagcttggtc  54420
gttgttgatg tgtagcagtg ctactgattt gtgtacattg attttgtaat ctgagacttg  54480
actgattttt ttgtttgttt tttgagatgg agtcttgctc tggagtgcag tggcccagac  54540
ttggctcact gcaacctccg cctctgaagt tcaaacgatt ctcctgtctc agcctcccga  54600
gtagctggga ctacagccac ccaccaccat gcctggctaa tttttgtatt tttagtacag  54660
acagtttcac catgttggtc agactggtgt cgaactcctg aactcaggtg atccacctgc  54720
cttggcctcc caaagtgctg ggattacagg cgtgagccac cgcgcccagc caactgaatt  54780
tgtttatcaa atctatgcgt ctttttgagg agtctttagg gttttctagt tatatgatga  54840
tatcatctgc aaacagctat agtttgactt cctcttttcc aatttggatg ccctttattt  54900
ctttctcttg cctgattgct ctggctatga cttccagtac tatattgaat agaactggtg  54960
aaagtaaaca tccttgtctt gttccagttc tcaggggggga atgctttcac tttttccgca  55020
ttgagcatga tgttagctgt agctttgtca tatacggctt ttgttatttt gagataagtc  55080
ccttctatgc ctagtttgtt gagtgttttt atcataaaga aatgctggat tttattgaat  55140
ccttttttctg caactattga aatgatcatg tagtttttgt tttaaattct gtttatgtga  55200
tatatcacat ttattgacat gagtatgtta aaccatccct gcattcctcg gatgaagtcc  55260
acttgatcat ggtgtattat atttttgata tgctgttgga ttttcttagc tagtattttg  55320
ttgatgattt ttgcctccat gttcattagg gatattggtc tgtcattttc ttttttttctt  55380
tttttgtatg tcctttcctg gtttggctat cagggatata ccggtttcat agaatgagtt  55440
agggaggatt acctctttct cagtcatttg gaatagtttc agtaggattg gcaccagttc  55500
ttctttgaat gtctgataga atttatccat taatccatct ggtcctgggc ttttcttgtt  55560
ggcaatcttt tttgaaatta ctgattcagt ctcactgctt gttattggtc tgttcagggc  55620
ttctgtttct tcctgattta atctaggagg gttgtatgtt tccaggaatt tatccatttc  55680
ctttagcttt tctgtttatc tccatagagg ggttcatagt agacttgaat gattttttct  55740
gttgctatgg tgttcattgt aatgtctcca gtttcatttc taattgagtg tatttgagtc  55800
ttcttttctt ggtcagtctg gctaatggtc tatcaatttt gtttatcttt tcaaagaacc  55860
agcttttttg tttcattgat attttgtatt tttttaaatt taattttcat ttggttctgt  55920
tcagatcttt gttacttcct ttcttttgct agatttgggt ttagttcttg tttctctagt  55980
tccttgaggt atgatgttag gttgtcaatt tgtgatcttt tagacttctt gatgtaggca  56040
tttagtgcta caaactttcc cttagcactg cttttgtcct atcccagagg taatgataac  56100
ttgtgtcact attatccttc atttcaagga atttttaaat ttcctttatt ttttcttttt  56160
gagacagaat cttgctctgt ctcccaggtt ggagtgcagt ggcgtgatct tggctcactg  56220
caacctctgc ctcccaggtt caatcgattc accagcctct gcctcctgag tagctgggac  56280
tacaggcgtg tgccagaatg cctggctaat ttttgtattt ttagtagaga tggggttttg  56340
ccatgttggc caggctggtc tctaactcct gacctcaggt gatctgccca ccttggcctc  56400
tgaaagtggt gggattacgg gcatgagcca ctacacccag cctaaacttt ccatcttgat  56460
ttcattatta acccaaaaat cattcaagag cagactgttt aatttctgtg tatttgtata  56520
gttttgaggg tccctttttgt agttgatttc tagttttatt ccactgtggt cttagaagat  56580
atttgatatg attttgatat ttgtaaattt attgagactt gttttgtggc ctctcatatg  56640
```

```
gtctgtcttg gagaatgttt catatgctga aaggaagaat ttgtattctg cagttcttgg  56700
gaagaatgtt ctgtaagtat ctattaggtc catttattct agagtatagt ttaagtccat  56760
tgtttctttg ttgactttct gtcttgatct gtctagtgct gtcagtggag tgggtgaagt  56820
ctcccactac tcttgtgttg ctattttatt tcttaggtct agtagtaaat gttttacgaa  56880
tctgagagtt ccagtgttag gtgcatataa atttaggatt gtaaaatctt cttgttcagt  56940
tgatcctttt atcattatat aatgaccttc tgtgtctttt ttttttttaa actgttgttg  57000
ctttaaagtc tgttttatct gatataagaa tagctactac tgactgggtg cagcagttca  57060
cacctgtaat cctagcactt tgggaggcca aggcgggtag atcacctgag atcaggagtt  57120
ccagaccagc caggccaaat ggtgaaaccc tgtctctagt aaaaatacaa aattggccca  57180
tgtggtggct catgcctgta atcccagcta ctggagaggc tgatgcagga gaattgcttg  57240
acccaggagg cggaggttgc agtgagctga gatcgtgcca ttgcactcca gcctgggcca  57300
caagagtgaa accctggctc aaaaaacaaa aaaacaaaaa aagaatagct actgctgctc  57360
acttttggtt tctatttgca tggaatatct tttctacccc tttaccttga gtttatatga  57420
atccttacat gttaggtgag tctcttgaag actgcaaata tttggtttgt gattttttta  57480
agccattctg tcaatctgta tcttttaagt ggagcattta ggccatttac attcaatgtg  57540
aatattgaga tgtgaggtat tgttccagtc atcatgttaa ttgttaccta ggtacttgtt  57600
ttcttcatgt tgttattgtt ttatgggccc tgtgtgtttt atgctttcaa gaggttctct  57660
tctggtgcat atcaaccttt tatttcagga tttagaactc attttagcat ttcttgtagg  57720
gctggcctgg tagtgacaaa ttccatcagc atttgtttgt ctgaaaatga ctttattcat  57780
gtatgaaact tagttttgct ggatacaaaa ttcttagctg acagttattg tttaaggagg  57840
ctaaaggtag gaccccaatc ccttttggat tgtaaagttt ctggtgagaa gcctgcagtt  57900
agtctgatag gttttccttt ataggttacc cggtgcattt gtctcactgc tctcagaatt  57960
ctttctgtca tgttgacttt agatagactg attattatat atgccttggt gaagtccttt  58020
ttgtgatgaa tctcccagga attttttgag cttcttgtat ttggatatct atatctctag  58080
caaggccaga gaagttttcc tcaattattc cctcgaataa aatttccaaa ctgtttgctg  58140
tcttctctct cagcaacacc agttattctt aggtttggcc attttacatg atcccatatt  58200
tcttggagac tttattcact tcttttgatt tttttcttta tttttgtctg attattaatt  58260
tgaaaactat atctttgagc tctgaaacta tttattctac ttgttctagt ctattgttaa  58320
aacttttcca tgcatattgt acttccctaa atgtgtcttt catttccaga agttctgatt  58380
ggcttttctt taaaatatct atttctttat aaaatttttt attcatatcc tgaagtttta  58440
aaaaatttct ttatattggc tttcaccttt ctctggtatc ttcttgagta acttaataat  58500
caatcttttt aattctttgt ctggcatttc agagatttca tcttggtttg gatccattgc  58560
tggagagcta gtgtgatctt ttgggggtgt aatagaatcc tgtttttttc atattaccag  58620
aattattttt ctgttttttt tctctctctc atttgggtag aatatatctt ctaattagtc  58680
ttgaatttat tttttattca attgttggtt ttttttattt atcttttctc ccttaaggat  58740
gtgactttat tgtagcctat ttcgactctt ggtgctttca gaggtgaaga ctattaattc  58800
cttggttata gaaagtcttt gtttgatggc tttctcagat aatggttgta gtagcattgt  58860
gctcactgtc tccaatgggg ttggaattgc agaggtatct tgaagcttac cttgttctcc  58920
tgtgttgtgc acttatattt gtttattttc cctgtatttt atttactggg ttgaatattt  58980
taggcttcag gccagtaggg gagacatctc tggtagaaac tggttgtggt tattgtagta  59040
```

```
ggtaaatgca gtacccaatg gcgggctgaa gtcccaatct tgacataggt gataggtgga  59100
gctctcagtg aaacacactg aggtcttatc agggggtaga ttgggagcca catcagctcc  59160
cccgcaaggc gcagggaagc agtccacctc ccagacacac tcctgactca gtgttccagc  59220
tatgcagatc agacaggcac ctcattttgt ctgcaggaac gttgatgttc caagttgaga  59280
ggaatcgtga gtctacctct catccaagtc tgaacataga aggtgctctc tactgtgggg  59340
atgcagttac cctgaagttt tccagcaagg ctctctatgg tgtacccaca catgctccca  59400
ctggaaaagc cccagttgtt tctgcagtgg tggacaaggg gaaaaagaag tccccttctc  59460
caagaccctt catgagcacc agggttacct gtgtgttggg gtagagcttc agactttccc  59520
tgctgagctc agtattgtaa ctgtgcctct gctgaaagag actttccatc agcagaaaga  59580
tccaggactc aaggcctgca tctggatttt tttgttccat ggggtgttcc cttgatgtgg  59640
tgcacaccca attcccctag gaagttttcc cctaggagta ggattcccta agaaacagac  59700
cactgtgaat gctgctgctc tgctgcgtct agccacctag tggagctgcc acactccagg  59760
ctggtgctgg ggagtgtctg caagagatcc agtgatgtga ccagtcctta attgtcccag  59820
cagcaagtac caacacccct tctgatgcgg gtcacagggg agtgatgtag actctgtgag  59880
attccttggt tgtaaatagc cttcatgtat tggctgtctc aaatgctgct tgtagtacca  59940
atgaatctgt catgtggaca gatcaggacc tcctggttag ccagggtggt gcaggcgatg  60000
gtgatagctg aggtcatgca caagttttct ctttcctggg cacagggtta ttctacccaa  60060
cgatgctata atgtatcagt tggcctccag ccaggaggtg gtacttgcaa tagagcacca  60120
gctacagtag aagtggtggg attaactgct ttgctttatg ttaattgcct tatgttaccc  60180
cagagaggta ctctggattc tcaggcaatg gccatagggc tcccaaaagt tgctgtccct  60240
tgtagtgaac taccagggct ggtgtagggg caaagccagg taggggctgg gttaggcagg  60300
tccatgcttt ggctctccat gtgcagggca agcagaggct cctgaggggt ttagggggca  60360
tttctctggc cactggggta atgtttcagg aaggaacata gctgcctctg ccacataaaa  60420
gagttcacaa gcctcaccca gctctcatgc acttggcaag gcaggtctct cacctatagt  60480
gttcactagc agccgctagc taaattccag gccgtgtaag ctcagaactc aaaactgccc  60540
taggccataa gccttccctg tggagacagg aaccagtgtt caggccatgc cccctcccaa  60600
tctacctgca aagcaagagt gcccggttcc tgtgcctgtg gctgcagcac acttcttact  60660
cacccactgg ttctggtcaa gggagttcat ccccactcaa gattatatga atttcagttg  60720
ggagcttctt tcaacctgca acctctgcct gagctagttg acttccgtga ggccctctgt  60780
gacgtagaat caggagtggc ttccctcggt ctgtgctgga gactaggaat gcatgcaagg  60840
ctctgcttgc tgctgctcct acttttatat taccccacca ctccctatat tagttccagt  60900
gctgggtatg gttaaggcct tcccctgtgg gctgaattgc caggttacct ggtggggatg  60960
tatatcctgg aggcagtctc tccccctgtc acactctgag gacttacaat ttttcacctg  61020
gctcacagtg ggtgtaggct gcagcctgct gcttctttca aagggtctat ggtttctgtt  61080
tttctgttca gttcctgcat tgcttcttag aaaaaagttc acagtatgaa tttctactca  61140
ccattttgtc tttccaagtg ggagagtcat gctgacactg tttccaatcc accatcttgg  61200
gaagaaaaac aaaacaaaat gtgatttttc ttagcctatc cacatggtag tttagattga  61260
ttgattttca aatattgaaa cagccatgca tgcctgtaat aaaccctact tgtaatcatt  61320
tattacttta tttaaatgtg atctcttttc tttgaaatat atttaaaata gtctttgcta  61380
```

aatctattgt ttgggattac tcaaagatga tttctgttga cttgtttcct aagtaaagaa 61440
cacactgctg gccaggtgca gtggctcatg cctataatcc cagcactttg ggaggctgag 61500
gcgggcggat catgaggtca agagatagag accatcctgg ccaacatggt gaaaccctat 61560
ctctactaaa aatacaaaaa ttagccgggc gccagcacgc ctgtactccc agctactcag 61620
gagactgagg caggagaatt gcttgaatcc aggaggcgga ggttgcagtg agccgagatt 61680
gcaccactgc actccagcct ggcaacagag tgagactctg tctcaaaaaa aaaaacaaaa 61740
aaaaactggc attgtacaca ttatgttata ggaatgctac attgtgattt gccccaaagg 61800
gggttgctgt ttgtatgata cacttgtctg gactaattct gtggaatttg tctccactac 61860
aatgtgaggc tgctaatgtc tgcactcaca ttttttaaag agaggctttc tagaattact 61920
cttgtttcag catattttgt cagccaaaga ttagtcagag gtttggttca aacatctcaa 61980
gccagttagg tccccactct ttgctgatag atctgtgtat ggtttggaga atgtatttgc 62040
tgtggtttga atatttgtct ccttcaaaac ttgtgttgaa atatagtcct caatgtagca 62100
atattaagag gtggggcctt taagaggtga ttggattatg agggctttgt cctcatgaat 62160
ggattaatcc attcatagat taatggatta gtgggtaaat ggattaatgg gttattttgg 62220
gaggggaact ggtgactgta taagaagagg aaaaaagacc tgtgcaagca tgttagcatg 62280
ctcattctcc tccccatgtg ataccccatg ttgccttgga actctacaga aagtccctct 62340
gttagtccat tttggggttg ctatgaagga atacttgaag gtgggtaatt tataaagaaa 62400
aaagatttat ttggttcatg gttctgcagg atgtacatga agcatggcac caacagctgc 62460
tcctgtgagg cctcaagaag cttacaatcg tggcagaagc tgaaggggga gccagcgtgt 62520
ggcatggcaa gggaaggagc aagagagaga gggaggagct gccaggctct tgaacaacca 62580
gatctcacgt gaactcacag attgaaattc actcattact gtgaggacac accaagccat 62640
ttatgaggga tgcacccccta tgacccaaac acctcctact aggcccacct ccaacatcag 62700
aggtcacatg aaacgagatg tataggggac aaaacagtca aaccatatca gtcccaccag 62760
caagaaggct ctcactggat gtggtccctt gatcttggac ttctcagcct ctgtaactgt 62820
aaaaaataaa ttttgtttct tataaattat ccggtttcgg gtattttgtt ataagtaaaa 62880
gatggactaa gaaagcattc aaagtttagg ctttcaaatc ttccctagct cttatttctt 62940
ttgagccctt tcaggccttt tctacctgtg tgcacagtct tgcagtcatc caggaatgtg 63000
tgaatagctc tagttctctc cggcctcttc tacacgtgtg tgcagctttc caataagttt 63060
gggacgtatg gagagcctat caaggttctc tatgtctatc tcatttttaa catctccttg 63120
ttaaatttct ggctagtctg ctggtgcctt gctttccccc aaccaggact gcaaccccag 63180
ggtagctgag tcattggcct ttcatatttg tttgctacct agattgctac tgtttttgat 63240
agtgttgctg ggtataccgc tttttgcact ctgcttcaag taaagtgagt tcagttcccc 63300
ctggcaggag actgtagaaa taattggccc agagaaagac attcaaatac tgacgtttaa 63360
gagaacccta actaaaaagc tggcacattg cctgattacg ggacaagcaa cagttctgaa 63420
agtgtggtcc atggacctcc cagggatcct taagattctt ttggggatcc aaaatattaa 63480
aattattttt ataatatttc atatcttatt tactttttc agtgtgttaa tttttgcaca 63540
gatggtccaa aagcaatgat aggtaacact gctggcccat ttagcatgaa tcaaagcagt 63600
agtacaaaac tatactagta gtcacttttt tcttcactgc catacaaaga atcattcaaa 63660
agccactttg gtccaggtgc agtggctcat gcttgtaatc acagcacttt gagaggccga 63720
ggcaggcagg tcacttgagg tcaggagttt gagaccagcc tggccaacat ggtgaaaccc 63780

```
cgtctctctt aaaaatataa aaatagccag gtgaggtggc caagatgccg ccattgcact  63840
acagccttgg tgacagagca agactctgtc taaaaaataa aaataaaaag ccactttggc  63900
cagacacagt ggttcacacc tgtaatccca gtactttggg aatccttggc aggtggatca  63960
cttgaggaca ggagttcgag accagcctgg gcaacatggt gaaaccccat ctctactaaa  64020
aatacaaaaa aattatccgg gtgtggtggt gcatgcttgc agtctcagct acttgggaag  64080
ctgaggtatg agaatcacgt gaacccaggt ggtggaggtt gcagcaagct gagatcgtgc  64140
cactgcactc cagcctgggt gacagagtga gactctgtct caaaaaataa aacaaaaaaa  64200
aacaaaaacg gacgggcaca gtggctcaca cctgtaatcc tagcactttg ggaagccaag  64260
gtgggtggat cacttgaagc caggagtttg agactagcct ggccaacgtg aaaccccatc  64320
tctactaaaa atacaaaaat tagccaggtg tggtggcagg cacctgtaat cccagctact  64380
tggaagcctg aggcaggaga atagcttgaa cccaagtggc agagattgca gtgagctgaa  64440
atcacgccac agcacagtga gactctatct caaaaaacaa aatcaaaaca acgccacttt  64500
tacttaagaa tgtccttgct gaagtagtaa atttattaat taaaaaaatt ctccaccctt  64560
acatacatga gtttttaata ttttgtgtga caaaatggga agcatgcata aagcatttga  64620
gcaattattt gagtttgtga gctttggtaa ctgatttttt tttttaatgt cttccctcat  64680
catccaggct agagtgcagt ggcatgatga tggctcaata caaccttgac ctcctgggct  64740
caagtgatcc tgccacctca gccttccaag taactggaac tataggagtg tgccaccatg  64800
actggttaat tttttttttt ttttttttgt agagacagtg tctcactatg ttgcccagaa  64860
ctcctgggct taagcaatcc tcctgccttg gcccccaaaa tgctcagatt acaggcatga  64920
gacatggtgc cccgcctgat tttttttttt atatgtagga aaaccatttt tctttgaatt  64980
actgatagac aaaaatatga atattcagac ttggatatct ggcaggcgtt ttctcaaaaa  65040
ttaataaaat gagcctgtca ttctgatagc atttgttgcc aatgataaaa tttgagcttt  65100
caagcaaaat ttagtatttt ggaaatttgt atctgcttct caatatttaa agatgttgct  65160
gataagatca atgataatga tatttttgat attatataaa gaattgtgct ataatcctag  65220
ctacttggga ggctgaggca agagaatcac ttgaacccag gaggtggagg ttgcggtgag  65280
ccgagattgc accactgcac ttcagtctgg gcaacagtgt gagactctgt ctcaaccaaa  65340
aaaaaaaaaa aaaaaaaaaa aaagaattgt gttaacattg gaaagccctg catatcttag  65400
tgaaccagta ttttccaaat gaccactgca tggtgtaaca aaatcatgta tgggcccatc  65460
tgataggggt ttaacattta aaatgtataa agtactcaac tcaatagcaa gaaagaaacc  65520
cacttaaaaa ataggcaaag gacctaaaag gacatttctc aaaagaagat atacaaatgg  65580
ccaacaggta catgaaaaaa tgttcagcat cacttatcac tggggggaaa tgcaaattaa  65640
aaccacaatg agatatcacc tcacacctgt tagaatgggt attatcaaaa agatgaaagt  65700
gctgaagagg ataagaggat gtggaaaaaa ggaaactctt atacattgtt agccggaagg  65760
caaattagca cagccattat ggaaaacagc aagcatgggg gttcctcaaa aaactaaata  65820
tagaactcgc ataaaaccca gtaatcccac ttctgggtat atatccaaag aaacaaatca  65880
atatgtcaaa gggatatctt cactcccatg ttcattataa cattattcat aagagccaag  65940
ctatggaaac aacccaagtg ttcatcaaca gatgaatgga taaagaaaat gtgatatata  66000
tatatgacat atatatgata tatacatcac attttcttta tccatttata tattattatt  66060
tatatatata tattccccaa tggaatacta ttcagcctta gaaaggctgt catttgtgac  66120
```

```
acgtggatga atctggagga cattatgcta aatgaaataa ggcagacaca aaaaggcaaa  66180
taccacgtaa tctaacttat ctgtggaatc taatgaaatt gaactcatag agaatagaat  66240
gaagagaact catacagaat agagaataga atgatggggg tgggagggag agaatgagga  66300
gtcattgatc aaagggtaga aagtttcata aaaggaggaa taacttttgt gatctattgc  66360
ccaacagggt gcctatagtc aacaatatgt taaatatttc aaaacaacac agttggctgg  66420
gtgcagtggc tcacacctgt aattccagtg agaggcgaag ccagctggac ttcctgggtc  66480
gagtggggac ttggagaact tttctgtctt acaagaggat tgtaaaacac accaatcagt  66540
gctctgtagt tagcaagagg attataaaat gcaccaatca gcgctctgta aaacgcacca  66600
atcagcactc tgtaaaacac accaatcagc aggatcctaa aagtagccaa ttgcagggag  66660
gattgaaaaa agggcgctct gataggacaa aacggaacat gggaggggac aaataaggga  66720
ataaaagctg gctgcccccc tccccacagc cagcagcggc aatgccctgg gggtccgttt  66780
ccgtggtgtg gaaactttgt tctttcactc ttcacaataa accttgctac agctcactcg  66840
ttgggtccct gctggtcttt aagagctgta acactcaccg tcaaagtctg tggcttcatt  66900
ctttaagtca gtgagatcac aaacccacca gaaggaacca actccagaca cactagcact  66960
ttgagagacc gaggcaggag gatcacctga tgtcaggagt tcgagaccag cctggccaac  67020
atgctgaaat cctatctcta ctaaaaacat aaaaattaac tcggcatggt ggcacatacc  67080
tgtattccca gctactactt gggaggttga ggcatgagaa tcgcttgaac aagggaggtg  67140
gaggttgcag tgagccaaaa ttgcaccact gcactccagc ctgcgtgaca gcaacactct  67200
gcctcaaaca aataaataaa aaataacagt aaatttcaga tgtctctgca caaaaaaaga  67260
taaagtgatg atatgttaat ttgtttgatt taataatccc atgttgtata cctatattaa  67320
aacatcacat tataccccat agatgtatac aattatgatt tggcaattta aaatattaat  67380
gaattttaaa aagagcagct ttctggccag gagcagtggc tcatgcctgt aatcccagca  67440
ctttgggagg ccgaggcagg ggatcaccag gtcaggagcg agaccatcct ggccaacatg  67500
gtgaaaccca gtctccacta aaaatataaa aagtacagaa attagctggg cgtggcggca  67560
cgtattccca gctactcagg aggctgaggc aggagaatgg cttgaactcg ggaggcggag  67620
gttgcagtga gccaagatca tgccactgca ttccagcccg actacagagc tagactctgt  67680
ctcaaataaa taaataaata aaagagcagc ttttcataaa aatgatttgc ctattacctt  67740
ttgagtagtc taatagtatc atttgtaaac caaaacaaaa aacagaaaac aaaattaagt  67800
gtgggtaaag atatatattc aatgtgaaaa ataagttaat ggatttaaat gtaacgagaa  67860
aaatgtattg actagtattc agatgccaca gtgcagttaa cctttaagaa accagtattt  67920
attaaatttt ggtgtggtgt caaagatgaa tatccataat tacctaaaag ggctgtttta  67980
aaatgccccc ttttccaact acaaatttgg atgaggctgt cttgtcatca tatacttcaa  68040
ccaaaaataa atatatatca gcacagaatg aaggcagaag cagatatgaa aatctacttc  68100
tattaggcca gagacattaa agagacttgc aaacacataa aacagtgcca ctcttctccc  68160
catttttgtt tggaataatg tattttttta aataaaatat taacatgcaa tagctttatt  68220
ttagctattt tattttactc tttttttttt ttagacaggg tctccctctg ttgccaaggc  68280
tggagtgctg tggtgtaatc atagctcact gcagcctcta agtcctgggt tcaagccatc  68340
atcccacctc agccttccaa gtagctggga ccacaggcat gcgccgccac cacacctcgc  68400
taattttta aatttcatag agatgaggac tcgctatgtt ggctagactg gtgtcgaact  68460
cctgggctca agtgatcctc ctgcctcagc cttccaaagt tctggggttg caggtatgag  68520
```

```
ccaccatgcc cagctatttt cgttatttaa tttttttaaa tttctaatat ggtaagtatt  68580
tgtagattta gcccacttaa acagaagctc tttatgtcct gaataatttt taagtatcta  68640
atggagtcct gagaccaaaa tatttaggga ccactgctct ggaggtcacg atatacatcc  68700
ttaacttatc atcgtctttt tttttgtttg tttgtttttg tttttttttt gatacagagt  68760
cttgctctct ctctcccagg ctggagtgca gtggcatgat cttggctcac tgcaagctcc  68820
tcccctcggg ttcaagcgat tatcctgcct cagcctcccg agtaactggg actacaggcg  68880
cccaccacca cgcccggcta attttttgtg tttttagtag agacggggtt tcaccgtgtt  68940
agccaggatg gtctcgatct cctgacctca tgatccgccc gcctcggcct cccaaagtgc  69000
tgggattaca ggcgtgagcc accacggcca gccatcattg tctgttttta agatactact  69060
ttgtgggcaa tgtaagaact ttacaacagt gtacttccaa ttgctaccct cccaaacttt  69120
atgctcttgt tgtcatatat tttactacac tatatgccag aatccccacg ttatattgtt  69180
atttttactt taaacagttg aggcacccag ggacatgtgt tgttcagcac tccacttaag  69240
aaaaactttg ctgttcacct gtgacaagtg cagttgcctg agagcctcca gctgcagggc  69300
tttcaggatc tgcctcatct ttagaactga ggacatgatc tctgtgccaa tgaatgagca  69360
tggcagactt actagggctt gaccatttcg gcacaatgca agactcctct aaagggcttg  69420
ctttgctatg aagcttctta ctgaattgcc taagattttg tcagccctcc ctgccaaatt  69480
ctgcctcctt ttccactctt tttacaggtg ttcagtttac atcgtggtct gaagccttcc  69540
cctgccaaat tctgaccctc gtttttaacc ttcccctcct caataaacct cttgcactcc  69600
taactctatc ttagcatttg cttcctaggg gacccaactg acataacagt cttcgttttt  69660
tagaaagact ttatctggtg ttttacaaat ttattcctgc agaattgagt ttctacctgg  69720
tatcatttca gcccttcagc ctaatggatt tcttttatca ttctgtgtag tttcagtctg  69780
ctagagacaa aattgtctct agcagctttt gtcagtctga cattactttg ccttcatttt  69840
tgaagactgt tttcactgga tacagaattg taagctgaca atctttgtct ttcatcattt  69900
caaaactgtc attccattgt cttccggcct ctactgcttc tggtgaaatg tcagacattt  69960
ttcttgtact gtgcctctct gtgcattatg tctttttttt tttttttttt tttctggctg  70020
ctttcaagat tttatcattg cctttggttt ttagcaggtg atgataatgg gcctatatgt  70080
ggatttcttt gcatttatcc tgcttggggt tcacagagca tcttggactt gtgggtcgat  70140
atatttgact gattttggta aatcttggcc atcaaatctt caaatattta tctgtcccat  70200
gcttccttct tgtgctgcaa tcacatatga gttaaactct tcaattctgt ctcacgtatc  70260
tcaaagagat acgtgtaaca gacactctgt cacatttttt gaaatcagct ttattaggga  70320
ataattgaca tacaataaat cacacatatt taaaatgtac acatccatgg aatcatcact  70380
ggtcaagata gtaaacatat ctatcacctc caaaagtttc cccgtactcc tttgtacact  70440
ttctctccta gtccactgtt tccagacaat gacttctctc tttcctttcc ttgccttccc  70500
ttccctttcc ctttcccttc ctttcctttc ctgtctcctt tctttctttc ctttcctttt  70560
tcctttcttt ctttcttttc ttttttgaca gagtttcact cttcttgccc aggctggagt  70620
gcaatggcac aatcttggct cactgcaacc tccacctccc aggttcaagt gactctactg  70680
tctcagtctc ctgagtagct gggattacag gcacctgcca ccatgcctgg ctaacttttg  70740
tatttttagt agagatgggg ttgagacagg gtttcaccat gttagtcagg ctggtctcga  70800
actcctgatc tcagatgatc cacccacctc ggcctcccaa agtgttgaga tgacaggtgt  70860
```

```
aagtcaccac gcctggcccc cttctctgtt ttatataact gttgattagt tgacattttc  70920
tagtgttttg tatgaatgga ataatataca ctgggaagtc gggcttcttt tacctattgg  70980
agtggctcaa attaaagact aaccatattt tgtatgtcaa ggatgtagaa gatgtttccc  71040
agcctgtact gagatgtttc tatgttactg catgtatcaa cagtctgtta ttgtttttac  71100
ttagtagtat tccattatat gggtagagca cagtctatcc attcaccatt acatggacat  71160
ttggattgtt ttcagtttgc tgttacaaac aaagctatga ggaacatttg tgtacaggta  71220
ttatatagag atacatttca ttttgggtaa atacctaaga ggagaatggc tggatcatat  71280
ggtaattata tgtttaactt ataaagaaac tgcctcagtt tcccaaagtg gttgtaccat  71340
tttcagttct caccaattgt atatcagagt tctagttcct ctacgtcctt gacaacaaaa  71400
aatatggtta gtttttaatt ttaaccatta caataggtgt ttactggtat cccattgtgg  71460
tttttatttg catttcccta ataaataatt gtattgagct tttatacacg tgcttatttg  71520
ccatccaaat atcttatttg ttaaaatttt gcttacatct tttgtttact ttaaaaataa  71580
gttgttagta ttcttgttac tgttaaacta tataaagagt tctttctata tttgggatat  71640
aagttcttta tcagatatct gctttgcaaa tatttctttc cagccaatgg ttagcctttt  71700
tcattgtctg cacagtgtct tttgaaaatc agaagtttta attttgatga agactaattt  71760
atcaattagt tcttttatgg atcatgcttt tggtgtttta tctaagaaac ctttgcctgg  71820
ccaggcgtgg tagctcacgc ctgtaatccc agcattttga gaggccaaga ctgatggatc  71880
accttaggtc agaagttcca gaccagcctg gccaacatgg tgaaacgatg tctctactaa  71940
aaatacaaaa aattagccgg gcgtggtggc aggcgcctgt agtcccagct actcggaagg  72000
ctgaggcagg agaatgacgt gaacctgggg gaggcggagc ttgcagtgag ccaagattgc  72060
gccacggcac tccagcctgg gcgacagagc gagactccgt ctcaaaaaaa aacaacaaca  72120
acaaaaaaga aaaacaagaa cctttgtcta acttaaggtc acaaagattt tctcctgtgt  72180
tttgtacgtt ttgtattgtt gtttcttaaa ctttttattt taacataact gtagattaac  72240
atacagctgt gaaataatac agatagatca catataccct ttatgcattt tttccagtag  72300
taacatcttg tataactgta agaacagtat cacaactagg aaattgacat tgatacaatc  72360
ctccactatt atttagatct caagagcttt acatttgtgt gtgtgtgtag ttctgtgtga  72420
ttttgtcata tgtgtggatt tatgtgacca gcaccacagt caagatataa aacagtttta  72480
tcagaaggat catttatgct aaccttttct agccacaact accttccttc cttccctatc  72540
cctaatccct ggttacaatt aatctgatat acatctccat gattttagta tttcaacagt  72600
tttatataaa tggaatcatg tagtacgtaa cattttgtgg ttggcttttt tctcttggca  72660
taattatccc cattttccac taagcctccc cttttgttta agctgggtag agtctggtaa  72720
acctcattgc aaccccaagt gttctgattg atagggcaac gggaaaagcc tcagggaaac  72780
attaggcagg aaatggcact gccttctaca agaaatgcct tagtttcttt acttgcaaaa  72840
tggagataaa attatgtgcc ctgtctgctt cacaagtctc ttgggagatt cttctggaat  72900
aatgaatgtg aatgagctct gtaaaatgta cattggcatg tacctgttat tactaacgat  72960
aaaagttttg tttatttgta ctgcctcatt gtctatggaa cccaggtctt ctccccttttg  73020
gtacttcaac tttctggttt gggcccatct tttctcacct ggggctttct atgtgctaga  73080
tagcctgact cggcacttta ggcatctgtg ctatccctat cacaaatatg gtctatgaat  73140
tcctgactcc agctcttact agctttgtag tgttggagaa ataatataac atccctaaat  73200
ctcagtttct ttatttgtaa actggagata aaaatagtat ataactccat aagggttgtt  73260
```

```
gtgagaaatg ccatgcttat ggtatgtgcc tggcacaccg gaagttactt gcccaaggcc  73320
acatggtcag tatacatcag agcttggcta gagtccaagt ctgtgatgcc aaagatatca  73380
ttcaggatca ctgaattctg tggtctttca atagcttact tgagttttct gcctcacctt  73440
ggttacatac tccacaagat gccaagagaa ctgagttact taaataatta aaaacaaaat  73500
aaaacaaaac accatgcttt taaggtctct cccttgtcca aagacctttg tttggttatc  73560
aatgccaggg actctctcta ccactccaga ttaattatgc taacattcaa gcctcctaac  73620
agtgctagac aaaacttatg tgtcaaatat gcctcactgc tatgtttagc ccacgagtgc  73680
cctggctgtg cctggaattc tgagcacata caaagatgga gagggctatt gatagattgg  73740
gtggtagagg gcatttccca gggggaaaat aatgggggtg aagaccaggg gacaggtaag  73800
catgatggtg tatatgggaa aaaggaaaca gtccatctaa cagcatgttg ggtacacaaa  73860
aagggggagt tgaagatgag actggaacat tagctggact gtgtaggcca tgagtgtggg  73920
tctaagatgc ctacttcctg tttaataggc aattaggaat cctcggacat gatgtcagag  73980
ctaaggacat ggccacctgt gcccctgcag gacatcttgg ctcagttttc actcagactg  74040
tctcagggtt tccatagtta gtctggggta gactctcagc actcccaccc catgtccttc  74100
ccctcatggt ctctgggagg cccagcctca ctcactatca gaagagtgct atcagcagtc  74160
tcataccact gagatgctgc aacctgaaga ccagagaaag cttctggaat gcaacatgac  74220
cacaagatct cattctctcc gcttgtctac atggaaatct ctatgcctca tagctgtaaa  74280
atggagataa cagcacctgc tttagaggag tgctatgtgg attaagtaag ataatgtaag  74340
aagagtgcat agcataggca ctaatctgcc ctggccttcc ctccagcaca ttccatacac  74400
agacttgtcc agtgtgtggg catcacctga gaagtagcca ctcagtttat gtctttcaga  74460
aaacacaaac aatccgtggt cacagaacag agataactgg tgattcagat ttccagtaca  74520
ttagaaggca cctgcgaagg tacttccctt cgcctcctgg gagccatcag tgagctctcc  74580
aggagagcag tatgatgcag agaaagaaac aaaggagatg cagatagtca tgtttctcct  74640
cattcacggg gtgaacttgg gcagcacctc cctttctctg atcctcagtt gctttgttga  74700
aatagggttg atgtgagggg ccagtgagat aatgcaggta aagtgctgca tggtggccag  74760
cactattagc tcctgatggg ggctgattct cccacgtggg tgcctgtgag actcaactaa  74820
ggggaggagc agtcaggatg gtcagaagct cccttgttgc tttctaggcc cttgctgtga  74880
cccatccctc tgggactggc tctgttgtaa gggtaaagaa gttctgtgac atccatgtgc  74940
catgtcactt tccacctggt agcagaggca ggcacatcag ctccttggct ctgtgctggt  75000
tctgctggaa ggttttataa gagcacactg tccagtagaa atgtagtgtg agctgcatgt  75060
gtaagtttaa gttttctggt aattacgtta aaaagaataa aaagcaggtg aaaataattg  75120
taatatattt attttattta acccaataga ggttgagtat tcctaatctg aaagtctaaa  75180
attcaaaatg caccaaaacc caaaatgggc attgacatga tgctcaaagg atatgctcac  75240
tggagcattt cagattttgg atattgggat taggatgctc aaccagtaag tataatgtta  75300
atgtgtcaag cccccgctc cccacccccc gcaaaaaatc agaaatttga aacatttctg  75360
gtcccaagca tagaaaagag atactcaacc catatattca aaatattatc attataatat  75420
gtaatcaata ttaaaacatt aatgagtttt tttatatgaa gtcttcaaag taccatgtgt  75480
gtcataaaca catcatggaa aatagtctta attaggacaa gtcacatttc aagaactcaa  75540
atagccatta ctatgtggcg gctgatagct tcctcattgg agagtttatg gcttagactc  75600
```

```
ggcttcctgg aaacagagcc atgctgccat ctggtggtta ctttgtcaaa taactcctca  75660
ggcatccacc ctgggctggc cccgtcgagg tcaatgaaga cagaagttac atccttcccg  75720
cccttcggtg ccctcaacct agagttcaga gcaaaggatg caaagtcccg gaagagaagc  75780
ctatctacat gccctgagat ttgaaagtga aaaggctgta acatgaggaa atctttcaca  75840
gatgtggaga tgagaagggg aaatcaccag cttggggtca tgtgataaat tcgtagctgc  75900
cctgaggtga ggacagcctt ggcccagcca ccagagtatc gtacctagac cgaggcaatt  75960
gcctagaaaa tattggggat tttttcgttg ttttttgttt gtttgttttt ttacaaagta  76020
atgaatccat tcacgtttca aaatgcaaaa gcagagtttc ccatccccac gaatcctaac  76080
tacccagttc ccctttagtg aggcatcaca ggtaatgctg tgataagctt gtacacttta  76140
ttattattat tttgagacag agtcttaagg ctggagtgca gtggcgttga tagagacagg  76200
aggcagccaa ggcacgcccc caccctcgga cccccgacac ccacctttaa ggctgaaaaa  76260
ccagactgcc ggtccagatg aagcccgccc tttgccctac tgactctttc tgaatactgc  76320
ccacctgcga actgggagga ctgggtgggg cctcgggaag ttaacaccgt ttgtagcagg  76380
aggggcctgg cctctgctgt tcctgtgtgg taacctggga ttcaatcagt caggtggaga  76440
gcctgttagc aggactccat ctcactttac tgagttgttt ttcctttctg cccaataaat  76500
tccattcccc ctcacccttc aaagtgtctg tgagcctaat cgttcctggt cgtgtgacaa  76560
gaacctggtt tgtcctacaa cagcgtgatc acagctcact gcagcctcga cctcctaagc  76620
tcaagggatc ctcccacctc agcctcctgg gtagttggga tacaggcatg agccaccaca  76680
cgtggctaat ttttggtatt ttatgtagag acagtttcac catgttgcct aggctactct  76740
caaactcctg ggctcaagca atctcccctc cttggcctcc caaaatgttg ggattacagg  76800
catgagccac catgcccagc cccacatatt atttttacat gtgcaagtat atccatagac  76860
tatacgggta tactattcaa gaatagtttc ttgaaatgga gttgttgggc ccaaggatat  76920
gtgcctatgt aattttgata gataaagaat atctttttta aaaatcagct tttaaagata  76980
caatctacat ataaaaattc actattttaa gtgtacagtt tgacaaatgt gtatagttct  77040
gtaaccacca ccacgatcat gatgtagaac attgccatca ctccaggaag ttccctagtg  77100
gtccttagca gttaatttcc ccactcccac ctcagcctct gacaactact gatctggatt  77160
ctgcccttat aattatagtg gccttttcca gaatatcata gaaatgcaat agaatgtaat  77220
cttttctgtc tggatatttt cactttgcat atagatcatg cagttcatcc atattgttgc  77280
atgtatgatg tatcaaagta cagcagatcc ttgaataata ttttgtcgaa cattgtttta  77340
ctataatgtt gacgagaaaa aaaaaatcaa ttccctgctg aggccactgt ctgtgtgatg  77400
tttgcacatt ttccccacgc ctggattgat tttctctgag tattccagat tactcccaca  77460
tccccaaaga tgtacacgct aggttaattg ttacatctac atggtcccag tgtgagtgag  77520
cttgggtgta tgagtgtggc tcaggatggg acggcatcct gtctggagtt ggctcccgcc  77580
ttgcactctg agctgctggg ataggttcca gccacctgca accctgaact ggaataagca  77640
ggttggaaag tggatgaatg agtgaataca aattattgtt aaaagaattt ctgtaaagta  77700
tatgataatc ctacaatgca tgacatcaaa gaaaacagtc tgaaagctct cagcaagccc  77760
tctgtatttg tgattgtttt tgaactgcat ggtcgtagga gatgctcctg ataatttttg  77820
ctttgcaaac atttattctt tgattcaatc caccaccact atgaacactg tcacttactg  77880
attcaccaaa agttgtgtaa ataatgatct tacttgtttt tattaatctt tctcaaatgt  77940
atgtatagct cacttctatt tcaatgttta atattagaag tatttgaagt ctttatttag  78000
```

atatttcatg atgttttaat gacagaaata tgccatagga acttaactct tatatacatc 78060
aattagccta tggtaaaatt ggtttcatta tatgtcattt cacttaaagt tgttatttcc 78120
aagaacctat tgatgttaag tgaggacttt ctgcaatacc ttttttaaat tgttaagtga 78180
tatcatattc tatagatata tcagtttatc tgtttaccag gtgatggaca ttttgtttcc 78240
agtttgggat ttctatgaat aaagcttcta tgaacattca agtatttttt tttccccccg 78300
agacggagtt tcgccctttt tacccagcct ggagtgcaat ggcataatct tggcttactg 78360
caacctctgc ctcctgggtt caggcgattc tcctgcctca gcctccctgg tagctgggat 78420
tacaggcatg cactaccatg cctggctaat ttttgcattt ttagtagaaa cggggtttca 78480
ccatgttggt caggctggtc tggaactcct gacctcaggt gatctgcccg cctcagcctc 78540
ccaaattgct gggattaaag gcgtgagaca ctgcgcccag ccaaacattt gtctttaaag 78600
tttcctttct cctgagaaaa tacctagaag tggaatttct gggtcaaatg agaagtgaat 78660
gtttagcttt gtaagaaact gccagaggtt ccaagatggc caaataggaa cagctccagt 78720
ctacagctcc tagtatgagc gatgcagaag atgggtgatt tctgcatttc caactgaggt 78780
actgggttca tctcactgcg gctttttgga cagtgggtgc aggacagtga gtgcagccca 78840
cggagtgtga gctgaagcag ggtgaggcgt tgcctcacca aggaagcaca aggggtcagg 78900
gaattccctt tcctagccaa gggaagctgt gacagacggc acctggaaaa attgggacac 78960
tcccacccta atactttgct tttctaacgg tcttagaaaa tggcacacca ggagattata 79020
tcccgcacat ggcttggagg gtcccacgcc cacagagcct cgcttactgc tagcacaaca 79080
gtatgagatc aaactgcaag gcagcaatga ggcttgggga ggggcacctg ccattgctga 79140
ggcttgagta ggtaaacaaa gcggccggga agctctaact gggtgcagcc cactgaagct 79200
caaggaggcc tgcctgcctc tgtagactcc acctctgggg gcagggcata gctgaacaaa 79260
aagcagcaga aacttctgca gacttaaaag tccctgtctg acagctttga agagagtagt 79320
ggttctccca gcatggagtt tgagatctga gaatggacag actgcctcct caagtgggtc 79380
cctgaccccc gagtagtcta actgggagga acctcccagt aggggttgac caacacctca 79440
tacagtcggg tgcccctctg agatgaagct tctagaggaa cgatcagaca gcaacatttg 79500
ctgttctgca gtatttgctg ttctgcagcc tctgctggtg atacccaggc aaacagggtc 79560
tggagtgagc ctccagcaaa ctccaacaga cctgcagctg agggtcctga ctgttagaag 79620
gaaaactaac aaacagaaag gacatacaca caaaaacccc atctgtatgt caccatcatc 79680
aaagaccaaa ggtagataaa accacaaaga tggggagaaa ccaaagcaga aaagctgaaa 79740
attcaaaaaa ttagagcacc tcctctcctc caaaggaacg cagttccttg ccagcaatgg 79800
agcaaagctg gatggagaat gactttgaca agttgagaga agaaggcttc agatgatcag 79860
taataacaaa cttctctgag ctaaaggagg atgttcgaac ccatcgcaaa taagttaaaa 79920
cccttgaaaa aagattagac gaatggctaa ctagaataaa cagtgtagag aagtccttaa 79980
atgacctgat ggagctgaga accatggcag gagaactatg tgatgcatgc acaagcttca 80040
gtagccaatt ccatcaactg gaagaaaggg tatcagtgaa tgaagatcag atgaatgaaa 80100
tgaagcgaga agagaagttt agagaaaaaa gagtaaaaag aaatgaacaa agcctccaag 80160
aaatatggga ctatgtgaaa agaccaaatc tatgtctcat tggtgtacct gaaagtgacg 80220
gggagaatgg aacaaagttg gaaaacgctc tgcaggatat tatccaggag aacttcccca 80280
atctagcaag gcaggccaac attcaaattc aggaaataca gagaactcca caaagatact 80340

```
tcttgagaag agcaactcca agatacataa ttgtcagatt caccaaagtt taaatgaagg  80400
aaaaaatgtt aagggcagcc agagagaaag gttgggttac ccacaaaggg aagcccatca  80460
gactaacagc agatctcttg gcagaaactc tacaagccag aagagagtgg gggccgatat  80520
tcaacattct tgaagaaaag aattttcaac ccagaatttc atatccagcc aaactaagct  80580
tcataagtga aggagaaata aaatccttta cagacaagca aatgctgaga gattttgtca  80640
ccaccaggcg tgccttacaa gggctcctga aggaagcact aaacatgaaa aggaacaacc  80700
ggtaccagcc actgcaaaaa catgccaaat tgtaaagacc atcaatgcta ggaagaaact  80760
gcatcaacta acgagcaaaa taaccagcta acatcataac gacaggatca aattcacaca  80820
taagaatatt aaccttaaat gtaaatgggc taaatgctcc aattaaaaga cacagactgg  80880
caaattggat aaagagtcaa gacccatcag tgtgctatat tcaggagacc catctcacgt  80940
gtggagacac acatagtctc aaaataaagg gatggaggaa gatctaccaa atggaaaaaa  81000
aaaaaaaaaa aagcaggggt tgcaatccta gtctctgata aaacagactt taaaacaaca  81060
aagatctaaa gagacagaga aggccattac ataatggtaa agggatcaat tcaacaagaa  81120
gagctaacta acctaaacat atatgcaccc aatacaggag cacccagatt cataaagcga  81180
gtccttggag acctacaaag agacttagac tcccacacaa taataatggg agactttaac  81240
accccactgt caacattaga cagatcaatg agacagaaag ttaacaagga tatccaggaa  81300
ttgaactcag ctctgcacca agcggaccta atagacatct acagaattct ccaccccaag  81360
tcaagagaat atacattctt ctcagcacca catcacactt attccaaaat tgaccacata  81420
gttggaagta aagcactcct cagaaaatgt aaaagaacag aaattataac aaactgtctc  81480
tcagaccaca gtgcaatcaa actagaactc aggattaaga aactcactca aaaccgctca  81540
actacatgga aactgaacaa cctgctcctg aatgactact gggtacataa cgaaatgaag  81600
gcagaaataa agatgttctt tgaaaccaat gagaacaaag acacaacata ccagaatctc  81660
tgggacacat ttaaagcagt gtgtagaggg aaatttatag cactaaatgc ccacaagagg  81720
aagcaggaaa gatctaaaat tgacaccaaa acatcacaat taaaagaact agagaagcaa  81780
aagcaaacac attccaaagc tagcagaagg caagaaataa ctaagatcag agcagaactg  81840
aaggagatag agacacaaaa aacccttcaa aaaatcaatg aatccaggag ctggtttttt  81900
gaaaagatca acaaaattga tagactgcta gcaagactaa taaaaaagaa aagagagaag  81960
aatcaaatag atgcaatata aaatgataaa ggggaaatca ccaccaatcc cacagaaaca  82020
caaactacca tcagagaata ctataaacac ctctacacaa ataaactaga aaatctagaa  82080
gaaatggata aattcctgga cacatacacc ctcccgagac aaaaccagga agaagttgaa  82140
tccctgaata ggccaatagc aggctctgaa attgaggcaa taattaatag cctaccaacc  82200
aaaaaaattc caggaccaga tggattcaca gccgaattct accagaggta caaggaagag  82260
ctggtaccat tccttctgaa actattccaa tcaatagaaa aagagggaat cctccctaac  82320
tcattttatg aggccagcat catcctgata ccaaagcctg gcagagacac aacaaaaaaa  82380
aagagaattt tagaccaata tccctaatga actttgatgc aaaaatccta aataaaatac  82440
tggcaaacca aatccagcac cacatcaaaa agcttatcca ccatgatcaa gtgggcttca  82500
cccctgggat gcaaggctgg ttcaacatac acaaatcaat gaatgtaatc cagcatataa  82560
acagaaccaa agacaaaaac cacatgatta tctcaataga tgcagaaaag gcctttgaca  82620
aaattcaaca gcgcttcatg ctaaaaactc tcaattaggt attgatggga catatctcaa  82680
aataataaga gctatctatg gcaaacccac agccaatatc atactgaatg ggcaaaaact  82740
```

```
ggaagcattc cctttgaaaa cgggcacaag acagggatgc cctctctcac cactcctatt  82800
caacataatg ttggaagttc tggccagggc aatcaggcag gagaaagaaa taaagggtat  82860
tcaattagga aaagaggaag tcaaattgtc cctgtttaca gatgacatga ttgtataatt  82920
agaaaacccc atcatctcag cccaaaatct ccttaagctg ataagcaact tcagcaaagt  82980
ctcaggatac aaaatcaatt gtgcaaaaat cacaagcatt cctatacacc aacaacagac  83040
taagagagcc aaatcatgag tgaactccca ttcacaattg ctacaaagac aataaaatac  83100
ctaggaatcc aatttacaag ggatgtgaag gacctcttca aggagaacta caaaccactg  83160
ctcaatgaaa taaaagagga cacaaacaaa tggaagaaca ttccatgctc atggatagga  83220
agaatcaata tcatgaaaat gggccatact tcccaaggta atttatagat tcaatgccat  83280
ccccatcaag ctaccaatga ctttcttcac agaattggaa aaaactactt taaagttcat  83340
atggaaccaa aaaagagccc acattgccaa gacaatccta agccaaaaga acaaagctgg  83400
aggcatcacg ctacctgact tcaaactata ctacaaggct atagtaacca aaagagcatg  83460
gtagtggtac caaaacagag atatagacca atggaacaga acagagccct cagaaataat  83520
accacacatt tacaaccatc tgatctttga caaacctgac aaaaacaaga aatggggaaa  83580
ggattcccta tttaataaat ggtgctggga aaactggcta gccatatgta gaaagctgaa  83640
actggatccc ttccttatgc cttatacaaa aattaattaa agatggatta aagacttaaa  83700
tgttagacct aaaaccataa aaatcctaga agaaaaccta ggcaatacca ttcaggacat  83760
aggcatgggc aaggacttca tgtctaaaac accaaaagca atggcaacaa aagccaaaat  83820
tgacaaatgg gatctaatta aactaaagag cttctgcaca gcagaagaaa ctaccatcag  83880
agtgaacacg caagctacag aatgggagaa aatttttgca atctactcat ctgacaaagg  83940
gctaatatcc agaatctaca aagaacttaa acaaatttac aagaaaaaaa tcaaacaacc  84000
ccatcaacaa gtgggcaaag gatatgaaca gacagctccc aaagaagaca tttatgcagg  84060
caacagacac atgaaaaaat gctcaccatc actggccatc agagaaatgc aaatcaaaac  84120
cacaatgaga taccatctca caccagttag aatggtgatc attaaaaagt caggaaacaa  84180
caggtgctgg agaggatgtg gagaaatagg aacactttta cactgttggt gggactgtaa  84240
actagttcaa ccattgtgga agacagtgtg gcgattcctc aaggatctag aactagaaat  84300
accgtttgac ccagccatcc cattactggg tatataccca aaggattata aatcatgctg  84360
ctataaagac acatgcacac gtatgtttat tgcagcacta ttcacaatag caaagacctg  84420
gaaccaaccc aaatgtccat cgatgacaga ctgtattaag aaaatgtggc acatacacag  84480
catggaatac tatgcagcca taaaaaggat gagttcatgt ctttgtaggg acatggatga  84540
agctggaaac catcattctg agcaaactat ctcaaggaca gaaaaccaaa cactgtatgt  84600
tctcactcat aggtgggaat tgaacgagaa cacttggacg caggatgggg aacatcatac  84660
actggggcct gtggtgtggt gaggcggggg gagggatagc attaggagct atacctaatg  84720
taaatgatga gttattgggt gcagcacacc aacatggcac atgtatacat atgttacaaa  84780
cctgcacatg taccctagaa cttaaagtat aaaaaaaaaa aaaagaaaag aaactgccat  84840
actgttttcc aaagtaactg taccattttc catcaccact cacaattagg gttccagttg  84900
cttcacaccc tcactaacac ttggcatggt cggtcttttg aattttagct attctagtgg  84960
gtgtgtagtg gtattgcatt gtagtttaaa tttacagttg actgatgact aatgatactg  85020
tccatcatgc ttgtgcttac tcactatttg tatacattct ttggtgaaat acctgttcaa  85080
```

```
atattctgtc catttttaaa ttgggctgtt tgtcttctta gtatttaggt ataagtgatc  85140
tttatatatt ccagatacaa atcctttgtc tgatatagca gtcccccatt gtctgattca  85200
agtctcttgg tcttgctttc tgcagttcca gttactagtg gtcaattgca gtctgaaaat  85260
aggtgaatat agtacaataa gatattttga gagacagaga ccacattcac ataactttta  85320
tcacagtata ttattataat tgttctattt tattaatagt tattgccgtt aatttattac  85380
tgtgtctaat ttataagtta aactatatca taggtatttg tgtgtaggaa aaaccatagt  85440
gtatataagg ttcagtacta cccaccatta cagacatcca ccgaaggtct aagacatcaa  85500
ttagcctatt ttaccatagg ctataagagc acattctcat ggctcccctt gcccaatcct  85560
gcctcatccc ctttcctttc ataagtgtta ctccttaata attgcttttc tactcctcga  85620
tctcggcatc tgcttcccag aggactcaac tgacacacat ctttaaagaa aaataggcag  85680
atttatataa aggcaattca caaaaggaat ggtgaaataa ttaggaaaat gaaaagttac  85740
ggaatagtaa gatagacgtt tttatctatc atattagcaa agtttacaga agttgaataa  85800
tatctgtgtt ggctagcatg tattgggaat gtaaattgtc aagtatgtgg tcgtgtaaat  85860
tgacatacac attttggaaa gctgttttgc aaaatatttt aaaattacat gactcagaaa  85920
tttcactttt taaatgtact ttaaagaaca tttgccaatg tatgaaatga ggcatgttta  85980
ataatatgca ttgtaacatg atatataatt gttcaaccat tctggaaaga aacaaattga  86040
aactgacaac agtatacgcc cctgaggtag ttttgtagaa ccagctgaaa ttagagatcc  86100
ctttattctt tggccaagat tatactgaat ttttaaaaat tttttattgt ggtacaatat  86160
acataatatc tctttaacca tttgtaagtg tataatttag ttgcattaaa agcattcaca  86220
tgttgttaac tatcatcact atatatactc aaaatttttct cgaccccaac ataaactctg  86280
aatccattaa acaaaaattc ctccttccct ctttcccctc gtcctctagt aatctctatc  86340
ttactttttg tctctataaa tgtgcctatt ctatctgata caagtgaatt catacaatat  86400
ttgtccttct gtatctggct tatttcacta tgcataatgt ttttgaaagc caaccatgtt  86460
gtaacatata taaaaattcc atttctttta atggttgaat aatattccat tatatgtata  86520
tagcacattt tgtttattca ttcaacagtt gatggacact tgggttgttt tcaccttttg  86580
gctattgtga ataacgctac tgtgaaaagt ggtgtacaaa tatctgttta agtccctgct  86640
ttcaattctt ttggatatat acctaagagt agaattgctg gatttctgta tttatcattt  86700
gaggaactga ctgataaatt gtatgccaca gcagctgcac tattttgcat ccccaccagc  86760
aatacaaaag gattccaact tctccacata cttgtcaaca tttattattt tgtttctgaa  86820
aaaattatag ccattctagc agatgtgaag tggtatttca ctgtcatttg atttgcagtt  86880
ccctaatggc aaatgatatt aaacagcttt ccatgtgctc attggctatt tgtgtactat  86940
ttttggagaa gtgtctattc acatcctttg cccattttta aaaattggat tgttttcctg  87000
ttgtaggggg tatttttatt tttatttatt ttttagacaa ggtctcactc tgtcaccctg  87060
gctggagtgc agtggcacga tctcagctca ctgcaacctc cacttctggg cttaagctat  87120
cctcccacct cagcctccca agtagctggg actacaggca catgccacca tatctgggta  87180
atatttgtat tttgtgtaga gacgggtttt gccatattgc ccaggctggt ctcaaactcc  87240
tgggctcaag ccatctaccc gcctgggcct cccaaaatgc tggtgagcag tgaacccagc  87300
tggacttcct gggtcgagtg gggacttgga gaacttttct gtcttacaag aggcttgtaa  87360
aaatgtacca atcagcactc tgtagctagg actgtaaaac tcaccaatca gcactctgta  87420
gctagcaagg ggattgtaaa actcaccaat cagcactctg tagctagcaa ggggattgta  87480
```

```
aaatgcacca atcagcactc tgtaaaatgc accaatcagt gctctgtaaa atgcaccaat  87540
cagcgctctg taaaatgcac caatcagcag aatcctaaaa gtagccaatc gcagggagga  87600
ttgaaaaaaa ggcattctga taggacagaa atggaaaatg ggaggggaca aataagggaa  87660
taaaagctag ccacccagcc agcagtgaca atgggctggg gtccccttcc atgctgtgga  87720
agctttgttc ttttgctctt cacaataaat attgctgctg ctcactgttt gggtccgtgc  87780
catctttaag agctgtaaca ctcactgtga aggtctgcag ctgcattcct gaagtcggcc  87840
agaccatgaa cccgctggaa ggaaccaact ctggacacac tgggagccac cacacccagc  87900
caaaagttct ttatatattc tgattactag ttctttatca ggtatgtgac ttgcaaatat  87960
tttctcccac tctaaagctt gcctttactt gatagtatcc tttgatgcag aaaagtttta  88020
aattttggtg aaacccaagt tacctacttt ttttcttttt ttttgagaca agagtctcac  88080
gctgttgccc aggctggagt gcagtggtgc gatcttggct cactgcaacc tctgcctccc  88140
aggttcaagc gattctcctg cctcagcttc ctgagtagct gggactacag gcatgcgcca  88200
ccatgcccag ctaatttttg tatttttagt agaaacaggg tttcaccatc ttggccaggc  88260
tggtctcaaa ctcctggcct caagtgatcc acccacctca gcctcccaaa gtgctgggaa  88320
tacaagtgtg agccactgca cacagcctta cttttttttct tttgttgctg gtggttttgg  88380
tgtcatatcc atgaaactgt tgccaaatac aattgtgtga agattttctc caaaattttc  88440
ttctaaaagt tttatagttt tagctcttat gtgtagatct tggatgcatt ttgagttaat  88500
tttttatgtt gtccaaggta aggatccaac ttcattcttt tgcatgtgga tattgttttc  88560
ccagtaccat ttggtgaaaa aatgtccttt ccccattgaa tggtcttggc atcattgttg  88620
caaatcaatc gatcatatat atgtgagggt ttatttctga actctattct attgcaatag  88680
tctatatgtc tggctttatg ctagcaccgt aatgttttaa ttaatgtagc tttgtagtaa  88740
gtttcaaagt taagaagtat gagtcctcca actttattct ttttaaaggc agttttagca  88800
attcaaagcc ctttgtaatt tcatatgaat ttgaggatca gtataatgtt aagtcttcct  88860
gtccataaac acaggatgtc tgtccatgta tttagattag gtctttttta atttctttca  88920
gcagtgtttt atagttttca gtgtactagt cttttgcctt cttggttaga tttattcttc  88980
actatttaat tattttagat attactgtaa atagaattgc tttctaagtt ttctttttgg  89040
attgtttgtt gctgacatat aaaaacagat aattttcata tattgatttg tacactgcaa  89100
ctttgctgaa tttgtttatt agctgtagta gctttcatgt ggatttttgg gattcctgtg  89160
aatagagata attttacctc ttcctttcaa tttgaaagcc cccccacaca cacctatttt  89220
tttatctcat ctaatagctc tggctagaaa ttacagtatc gtgttgaata gcatgactga  89280
aagcaagcat tctttcctgt tccttatctc gggggaaact ttccattttt caccattatg  89340
atgttagctg tggacttttc acaaatacct ttattatgtg gagacatttt ccctctaatc  89400
ctaattttct gagtttttat catgaaagag tatggatatt gtcaaatgcc ttttctgcat  89460
caattgagat ggtcatgttt ttttctccat tctgattatg tgatctatta cattgatttt  89520
tcatatgttg tgccactttt gctttcctga gataaatcac atttggatat cataaataat  89580
tatttttctt ttttcttttc tttttttttt tttttttggt gacagagtct tgctctgtct  89640
cccaggctgg agtgcaatgg tgcaatcttg gctcactgca acctctgcct cccgggttca  89700
agggattctc ctgcctcagt ctcccaagta gctgggatta ctggtgcacg ctgccacgct  89760
cagctaaatt tttttgtatt ttagtagaga cagggtttta ctgtattgcc caggctggtc  89820
```

```
tggaactcct gagcttaggc aatccacctg cctcgtcctc ccaaagtgct aggattacag  89880
gtgtgagccg cgcccagccc aaataatcat tttaatatgc tgttggattc agtttgctaa  89940
tattttattg aggatttttt aacctatgtt tatgagaaat attgggctat aattttctct  90000
cttgtgatgt ctttatctga cattggcatc agagtaatgt agccttgtag agtgagttag  90060
gactattctc tccgcttcag ttttgtggaa gagtttgaga aggattgatg tgaattcttc  90120
tttaaatatt tggtagaatt ctccagtaca atatctggtc caggactttt ctttgttggg  90180
aggcttttca ttaccaattc aatattctta cttgttataa agctatgcaa aatttgtttc  90240
ttcttgagtc agtttacatg attcatgtgt tttaaggaat gtgtccatta cttctaggtt  90300
atctaacttg ttggcataca gttgttcatt gtattctctt acaatcctgt ttatctgtgt  90360
aaggttgaga gtaatgtccc cactttcatt tctgatttta gttatttaca tatctctttt  90420
tttctttgtc agttgaagta aagtttagtc aatttgttga tcttttcaaa gaaccaactt  90480
ttggttttac tgacttttct ctactgtttc tctactctat tttatctaag ctctagttct  90540
tattatgttg ttccttttgc tagcctttgg cttagtatgt tcttttcctt gttcattgag  90600
gtgtaaagtt aggttataga ttttgaacat ctttttaaaa gtaggcattt tcagttctgg  90660
attaccttct gaacactgct ttttctgcat ctcaaaagtt ggatcatggg gtttttggtt  90720
tgtttttaac cattctgcca actgctgttt tttatttgag agtttaaccc atttatattt  90780
aaagtacata ctgataaggg agaacttagc ttttccattt tgctatttgt tttctatatg  90840
ccttatagcc tttttgtcct tcatttcctc cattactgcc ttcttttgtg tgtaattggt  90900
ttgtagtgga acattttgat tccattcttg aattgatgcc aacttaactt ctatatcata  90960
caaacactct gctcctatat agctccattc ttttgatgtt accactgtca caacttatat  91020
ttttatatat tgtgtgccca ataatatagt ttcataatgt ttatatatta tttttaacat  91080
acagaaaaaa agaggagtta aaaaacaaaa ttacaattat gctagcttct atgattttcc  91140
atatatttat ctttacctct gatctttctt tctttttttt cctgagacag agtcttgctc  91200
tgtcactcag gctggagcac agtggtacaa tctcagctca ctgcaacctc tgcctcccgg  91260
gttcaagtga ttctcctgcc tcaacctccc aaagtgctgg gattacaggt gtgatccact  91320
gcacccaggc tttatttctt tatatggctt caaattacta tcagtacttt tattttgact  91380
tgaaatattc cctttagcat attttgcatg gaaagttttt tttttttttt ttttgagttg  91440
gagtcttgct ctgtcaccca ggctcgagtg cagtggcatg atctcagctc actgcaacct  91500
ccacctccca ggttcaagca attctcctgc ctcggcctcc cgagcagctg ggagtacagg  91560
catgcaccac tacacctggc taatttttgt atttgtaaca gagacggggt ttcgccatgt  91620
tggccaggct ggtctcgaac tcctgacctc aagtgatctg cctgccttgg cctcccaaag  91680
tgctggtatt acaggtgtga gccactgtgc ctggccttgg aaagtcttat ggtaatgaac  91740
tccctcagct cttgtttatc tgggaatgta ttaatttctc cctcattctt taagggcagt  91800
ttttctggat atagaattct tggtagacta ttatttcttt cagcactttg gatatgttaa  91860
cccactgcct cctagcctcc aaagtttctc atgagaaatt agctggtaat cttgctgagg  91920
atctcttttg tgtgatgagt tactaatact tccaggattc tttctctgtc tttgtcttca  91980
acattttaat tataagaggt cttcgtgtgg atctctttga atttatcctt cttggaattc  92040
gttgagcctc ttgaatttgg agattcatat cttttgtcaa atttggggag ttttcagcca  92100
ttatttattt cttcaaattc tttttgccct tttcttgctt ttttttccct ttggaactcc  92160
cataatgcat atgttggtct gcttggtagt atctcaaaag tcccttatgc tctgttcact  92220
```

```
tttcttcatt tcttttttc cattcctccc actttataac ttcaattgtc ctatcttcaa  92280
ttttactgat tctttcttct gcctgttcag atctcttttt gtaaccatct agtaaaatct  92340
tcatttcagt tatcgtacat tttagttcca gaatttattt ttggttcctt ttttatattt  92400
tatatctttt tattgatatt ctcattttgt tcatacaaca ttttcctgtt ttgctcattt  92460
ctttctgtag atcttcgagt atctttaaga cagttgtttt ggccaggcgt taggcacttt  92520
gggaggctga ggcaggtgga tcatgaggtc aggagttcaa ggccagcctg gccagtatgg  92580
tgaaacccca tctctactaa caatacaaaa gttagttggg catggtggcg catgcctgta  92640
gtcccagctg cttgggaggc tgaggcagca gaatcgcttg aactcaggag gtggaggttg  92700
cagtgagccg aaatcatgcc actccactcc agcctgggtg acagagcaag actctgtctc  92760
aaaacaaaca aacaaaacaa caacaacaaa aaaaaccctt gttttaaagt gtttgtctag  92820
aagtccaatg cctgcgattt ttttggaata gtttctgaag atttaatttg ttcctttgaa  92880
tgagccatgt tttcttgttt ctttgtatgc tttgggattt gttgttgatg ttgaaaactg  92940
gatatttgtt tatcatataa tgtggtaatt ctggaaatca gattctcccc cttccccagg  93000
gttgctttct atttttatt gctgtcgggt atctctgtgc tagagatcat cctgaggcaa  93060
aagcttaaag gcttttctat actttgtctt tccctgggcg gtatggtgac attgtaaata  93120
ttctcgtata tatggttgct tttcaatgtt ctaagtttta cacgtctggc tcccaacact  93180
agaaaaaggg aggaaaaaaa agaagaaaag acccttctca caccattcta gatactgtcc  93240
ctggatgctg cttctgttgg tggggttgaa acaatggctt cacttttctg tgtctgcact  93300
tttccatcat cagaagcagc agtcagcagt tcagaataca gaattattag aggatgagat  93360
ctgtattgac caccctggct tctgaaactc tcaccaggaa tgtggccatg gctgcttacc  93420
atggtactga tgttgaagag ataggtagct atgactgaaa ttgactgaaa ttaatcagaa  93480
tttagcagct aagcccttcc ctggaagttg caagtgttca aatgacctcc agagttacaa  93540
aatagttaca tcggtagtta gttaactgat agtttctact agcgtaattg ctgtctgggt  93600
gtaaagacag attcctgatg cttcctgtta tgccatattc cttgatgtca ctctatacaa  93660
atttttaatt gctattttat atcaaaaaat acataaaaga gacagcatta gagcacaaga  93720
ggttgtatgt ggtcaatttc ccatcaagtt taaccactca catattgcta ataccagtca  93780
tgcacttgtg catatgctgg gattgtttac ttttcagaaa aaaattgagg acctcaatct  93840
agtaatgaat tacatagaac tggggagaga tgacagaaga gttgctaaca acttgtatcc  93900
aaactgctga gtgcagaagc agggactact ctgaagaaac aaagtgaggt gggggtggg  93960
ggttgcagga atgtgggccc tgaaagcatc caattactat attctttaat ttttatttgg  94020
gttattgatg cttctctttc cttaaacaaa aacatgataa atacatttaa atttctcttc  94080
tgaaaacttg gtaattcaat acaaccctat gactaatgac aattaaaaca gtggaacaaa  94140
attgtttcta aaaacttgaa ggcatttaag agctaaaaag gtagtgaaaa atctggtcaa  94200
gatgaaaaaa aggtattgta gaaatccaga gaggtgagac aagcttttgg ggattttttg  94260
tatggagata tttgtgtata ctgagaggtg gctgagaggc tgagaagtgc ttttcatagc  94320
actttggagc aagagggtac cagtccacac tctgggttgg cctctaaaac ctgtacccta  94380
gaggtaagaa tgagccagaa gtaaactagt tctcacatgg attatagctc agttttgtgt  94440
catatgggta gctcagaaaa attccaattt gtgaaacgat actaaggtga ttctggatcc  94500
cctgtaaccc aataatctga cagaagcaag taaaaatcct ctctgaagaa agatgacatc  94560
```

-continued

```
atcctaggct ctaagctcca cactttttct acaaacactt tctcaataca gtggtctagc  94620
aaacactatg tatgcaggca tacaatcgta tagaacagca taaccaaaac tcaaacaaaa  94680
aaattaacaa tagaaacaaa ctcacggggg ctgtgatact ggaattaaca gattttgact  94740
ccaaaataaa tggttactct gttcaaggag ttaaaagtca agaaggaaaa ttttgtgaga  94800
taactagaaa ttctaaaaat aaagcagata tgacaaagaa ctgtgtagac gttgtacaac  94860
tgaaaaatat aggaacttaa atttaaacca aatggatgtt tttaatagaa tattagaaac  94920
agctgataaa ataataaact gaaagatcag aatgaatatt tagaataaat aacactgaaa  94980
caaaaagaaa aacacaacag aagagatgga aaaaaacatg gaggatgcag tgtgagggtt  95040
taagaatgtc agagttttag gccaggcgca gtggctcacg catgtaatcc cagcactttg  95100
ggaggccgag gcaggtggat cacgaggtca gggattcgag accagcctga tcaaggtgaa  95160
accccgtctc tactaaaaat acaaaaatta gctgggtgtg gtgatgtgtg cctgtaatcc  95220
cagctactta ggaggctgag gcaggagaat tgcctgaacc cgggaggcag aagttgcagt  95280
gaaccaagat cacaccactg cactccagcc tgggcaacag agcgagactc catctcaaaa  95340
aataataata tcagagtttt agaagagagg gagaaaattg gacagaaaaa tcatttgaaa  95400
agtggttaag gattttccct gatccttttg tatctcataa acatgatgat tgggttttca  95460
cacacacatg taagatgtgt caccatcaat ccttgttatg acatcagcac attacccatc  95520
taacatgatt gaaaaaaaaa aaaaaagaat tttccccaaa tggtgaaaga catcaaattc  95580
catagtaaaa gtcccaatga cccctattag gatctacaaa aagaaatcca cactttgaca  95640
catcataaca aaacagaaga aaacaaaaac aaggagaaaa atcttaaaag cggccaaagc  95700
ttaaaagaca cattttgcct tcaaagacca ccaattaaga caataaaaga tcttcaaagt  95760
gttgaaaaaa taaataactg ctgaactaga aatctacacc cagcaaaggc atctttagaa  95820
aactgaggca aagaattctg tttggagcaa gatgacagtt ttgcagtttt ttcatctccc  95880
tacattctct aatcaaaata gatgaagcaa cagaatagta aaagaaacat ggacatctta  95940
actgaactga ggaacaaggt aactaataat cccagaagaa aacagggtgg gccaaactat  96000
cagcattctt gcaggaagtg tgaaaggaag agaaatgaga attctggtag tcctaagggc  96060
ttcagaacac agaaattgcc acaaatattt atccctaata ggagtagctc tgagtgtggt  96120
aataaactga agcaccaaat agatttaagc aatagacatg ggagaagttt tctccatttc  96180
taatttccag atgagtacaa aaaatgtcta tgaaggccgg gcatggtggc tcacacctgt  96240
aatcccagca ctttgggagg ccaagatggg tggatcacct gaggtcagga attcaagacc  96300
agcctgacca aagtggagaa acctcatctc tactaaaaat acaaaaaatc agccagtcgt  96360
ggtggcaggc gccagtaatc ccagctactc gggaggctga ggcaggagaa tcacttgaac  96420
ccaggaggcg gagcttgcaa tgagctgaga tcgcaccagt gtactccagc ctgggcaaga  96480
agagcaaaac tccatcacac acacacaaaa agtctatgaa ggaacagggt atacaggaca  96540
tgaatggagg tgagacttct gtgaatgtac ctttttgtaa gtgatttgca taattctagg  96600
gatttgaaat taaaatgata gaatagtgac agaagaatta gacaaaaagg cctctcagaa  96660
tttaggccag agtgtgaaga tgttccccca cccccatgtg aaaagtaatt aaataatcct  96720
ctcctgcaga ggagagtcac aataataaca ttgttaataa aatacactga atatcagcca  96780
acttctttct tggtggtggc tatgctttct cagctagtgt ttgaacaaaa tagacatggt  96840
aatagaaaca gatgttacaa atggattaac aagtggactt actctcaccc aggttcacct  96900
ggctgctgca acactgagtc ctcagccttc cagcagcaaa gaccaataat tcattgacac  96960
```

```
tgtaaacagt ttattctaga tcttaatttc ctccttttta caatgttggg ctagcaacat  97020
cttttatgga aatttgtttg ccttagtcat tgttatggca ttatacatat aattgggagg  97080
tgaagccagc tgggcttctg ggtcgggtgg ggacttggag aaattccaga catataatta  97140
cctctgaata agtgtgacac agactgctag gtttttataa tagcgttagt gtagtgcttt  97200
tttgaaagtt gagcatggca ccagctggga gatatcacct tgagaagctg gaatgttttc  97260
tttttttaa atacggagtc tcactctgtc gcccaggctg gagtgcagtg gcatgatctc  97320
agctcactgc aacctccgcc tcccgggttc aagtgatttt tgcacttcag cctcccaagt  97380
agctgggact acaggcgccc gccactcact tgtgtaagat tggaattatt ttttccttaa  97440
aatattttac aaagttcacc agaggagcaa tctgggcctg cagttttctt tgagggaaga  97500
aaagaaatgg ctaatttttg tatttttagt agacagggtt tcactatgtt ggccaggctg  97560
gtctcgaact tctgacctca agagatcctc cctcctcggc ctcccaaagt gctggaatta  97620
cagccatgag ccactgccct ggccagaatg ttttcctata ggctatagca tatgttttaa  97680
gccagtatgt gtccatgcta ccaggcaaga aaaagagata aaatgtgttc agatggaaag  97740
aaagaggtga aactgtcttt attcacaggc aacatgatcc tatatgtaga aaatcctaaa  97800
gaattcatag caaactatta gcactaataa atgaattcag gaaggtcaca gaatacaagc  97860
tcaatacaaa aaaattggtt gtatttctat atactgcaat tagcaataca aaaattcaaa  97920
taataacaga tcaaaaagaa atacttagga ataaatttaa gaaaagaggt tttaagactt  97980
gtggactaaa aactgtaaga cattgctggg gcagggtggg gggattaaag aagacctaaa  98040
taaatggaga agatatacca tgttcattga ttggaagatt caatattgtt acaatgacaa  98100
ctctctccaa attgatctat aaatgccatg taatccatgt caatattcta gcagacttct  98160
ttgcagaaat ggcaagctga tcctgaaact tatatggaaa tggaaggatg cagaatagcc  98220
aaaacaattt tgaaaaagaa gaacgatgtg ggaggacttc tgtttcttga ttttaaaatt  98280
gaacagaatg ctatggtaat gaagacagtg tggtactggt gtatagatag ccatatgaat  98340
caatagaaca gaatggagag tccagaaatt aacccacata tacatgatca attgattttt  98400
gacaaaagtg ctaaggcaat ccagtaggga aaaggatagt cttttcaaca agtggtgcta  98460
tgacaatcgg atatacatat gcaaaacaaa caatttttag accttactcc ataccaaaca  98520
caaaaaaatc aactccaaat agattataga aaagtataac tgaagcctgg gcatggtggc  98580
ttatgcctgt aatcctagca ctttgggagg ccaaggcagg aggattactt gaggtcagga  98640
gttcgggacc agcctggcca acatggtgaa accctgtttc tactaataat acaaaaaaaa  98700
aaaattagcc aggcatggtg gcacatgcct gtaatcccag ctactcagga ggctgaggca  98760
caagaattgc ttgaacccgg gaggcgtagg ttgcagttgg cagagatggt gccactgcac  98820
tccagcctag gtggcagagt gaaactgtct cacaaaataa ataaaataaa aatgcatatt  98880
tttgataatg cctacattag tcgacatgga accaaaatag caatattttt ttttaaaaag  98940
tagaactgaa aatataaaac ttttagaaaa aaataggaga aaatcttcat gatattggct  99000
agggcaaata tttcttagat atgataccaa aagcacaacc aataaagaaa aaaatgtgat  99060
aagttgaact tgatcaaaat taaaaacatt tgtatttcaa gagatatcat taagaaaata  99120
aaataattca cgtactaaga aaacttttac aaatcaaata tctgataaag gacttgtatt  99180
cagaacatat atatatattt ttttaatttt ttatttaatt tttttatttt ttgagacagc  99240
gttttgctct tgttgcccag gctggagtgc aatggcacaa tctcggctta ccacaacctc  99300
```

```
caactcccag attcaagtga ctctcctgcc tcagcctccc aagtagctga gattacaggc  99360
atgtgccacc actcccggct aattttgtat ttttagtaga gacagggttt caccatgttg  99420
gccaggctga tctcaaactc ctgacctcag gtgatccacc cacctcagcc tcccaaagtg  99480
ctaggattag aggcatgagc caccgtgcca ggcccagaat atatatttta aaactttaca  99540
acaaagtata aaagaaaaaa atagaaaaaa attaaatacg agagaatata ttcaaatggc  99600
tattaagcat gtgaaaagat gtttaacatc attattaaga aaacgcaaat taaagcagca  99660
acaaaccaat aaataactat aataactatt taaatagttg aactgtttac aataaatagt  99720
tctgtttgtc ccatagttac accatttgca ctaggtacca aaaagcaaag tggaagttat  99780
atttctacta ccaaaatgac ccattagaaa aatttttact tcttgttctc gtgactttgg  99840
gctccactgg cttagagatt ttagtactca aagggggaat aatttctctg ggcacacca  99900
cagtgattat actgaactgg aaattgagac tatctggcca ttttgagttc ttcatagcac  99960
tagagccaca gacaaaaagg ttacactggt ggaatcaatt aactagtatt ttgctaaaga 100020
tacatttata ttcatgatgg atgttggcat taattttttt gtgtaatgtc cttgtcagat 100080
tttgatatta agattatgct gttttcacaa aacaaattgg gaagtgctcc tcattcctgt 100140
gtttttgaaa gcacttaaga ttggtattat ttcttcctta aaatatttta caaagttggc 100200
cagaggagca atctgggcct gcagttttct ttgagggaat tatgactaat tcaattatat 100260
taacacatta tagctgttaa gtttcctgt ttcttctaaa gtgaggttta acaatagttt 100320
atatctttta agaaatttat tttatccaag ttattacatt tattggcata agcttgtgca 100380
taacttatta tccttttaat tctaaactgc taatcttccc agttttgttt cagatatgag 100440
gaatttgtgt tctctcatct ctctgtctct ctgtcttatt tggtgtactg gatacttgtg 100500
ctggcaactt ggtcaatctg tgaacgacat tacccagaat tcacttctcc ttatggtttt 100560
ggttagtgaa tctgcatgag attttagaag cagaagcagt ctctctctga agctgttcag 100620
tgtgagatag ttgatggaca gatgcagagt tgcctggtgg tttccagctc atcctggtgc 100680
tcctctgttt tacatccagc tctccttccc agctgctgaa cccagcccaa tcaggagatg 100740
cttggctgca aactttcaga agtgttatct aaacagagcc aacagccacc atatgacctt 100800
gtttccattc ccattttggt aactaaatgt gctaggcttc tccaattatc tatctttatc 100860
tctctctctc tctctctttt tttttttttt tttttgaga tggagtcttg ctgtgtcacc 100920
caggctggag tgctgtagtg cgatctcagc tcactgcaag ccccgcttct cgggttcacg 100980
ccattctcct gcctcagcct cccaagtagc tgggactaca ggcacctgcc accacggcca 101040
gctaattttt tgtattttta gtagagacag ggtttcaccg tgttagccag aatggtctca 101100
atctcctgac cacgtgatcc acccgccttg gcctcccaaa gtgctgggat tacaggcgtg 101160
agctactgtg cccggcctat atgagtaagt tctttaatgg ctatttgtga gattttggtg 101220
cacccattac ccgagcagta tacactgcac cttatttgca gtcttttctc cttcaccccc 101280
ttcccatcct ttccccctga gcacccaaag cccattgtgt cactcttata cctttgcatc 101340
ctcatagctt agctcccaat tatgagtgag aacataggac gtttggtttt ccatacctga 101400
gttacttcac ttagaataat actctccaat ctcatccagg ttgctgcaaa tgccattaac 101460
tcattccttt ttatggctga ctactattcc attgtatata aatataccac ggtttcttta 101520
actgcttgtt gactgatggg catttgggtt ggttccacat ttttgcaatt gcgaattgtg 101580
ctgctataaa catgtgtgtg caagtatctt tttcgaataa tgacttcttt tcctctgggg 101640
tagataccca gtagtgggat tgctggatca aatggtggtt ctacttttag ttctttaagg 101700
```

aatctccaca ctgttttcca cagtggctgt actagttccc atttccacca gcagtgtaga 101760
agtgttccct gttcaccaca tccacgccaa catctactat tttttgattt tttgattatg 101820
gccattcttg caagagtaaa gtagtattgg attgccaatt atctctttag gctccaattt 101880
gtcatctagc accaatgctt caggaggact tctgaacctt cacttctcta gctcttccca 101940
ctattatata aggtatagct cctaatctta ctctctcatc cagtaacact cattaaggct 102000
ctgctttcct gaataaaacc tgaacaatgt ccaatttgtc aatattttca aagaatcaac 102060
ttttggcatt ttaatttttt aagttgactg ttttatatgt cattgatttc tactcactat 102120
tctttccttc tgtttacatt ttaatttttt catcttaatg tggaatttta gatcactgat 102180
ttcaaaccta tttacttttt aaatgtaagc atttaaaact gtaaaatttc tgtggccagg 102240
cacggtggct cacacctgta atcctagcac tttgggaggc cgaggcgggt ggatcacctg 102300
aggtcaagag ttcaagacca gcctggccaa catggtgaaa ccccatctta accaaaaata 102360
caaaaattag ccaggcgtgg tggcaagtgc ctgtaatccc agcaactcag gaggctgaaa 102420
caggagaatt gcttggaccc aggaggtgga ggttgcagtg agctgagatt gtgccactgc 102480
attccagcct gggcgacaga gcaagactct atctcaaaaa aataaaaata aaaaataaat 102540
tgtaaaattt tctcaaatgg gatctaatta aactaaacag cttctgcaca gcaaaagaaa 102600
ctaccatcag attgaacagg caacctacag aatgggagaa aatttttgca atctacccat 102660
ctgacaaagg gctaatatcc agaatctaca atgaactcaa acaaatttac aagaaaaaaa 102720
caaacaaccc cattaaaaag tgggcaaagg atatgaacag acacttctca aaagaacaca 102780
tttatgcagc caacagacac atgaaaaaat gctcatcgtc actggtcatc agagaaatgc 102840
aaatcaaaac cacaatgaga taccatctca caccagttag agtgtgatca ttaaaaagtc 102900
aggaaacaac aggtgctgga gaggatgtgg agaaatagga acacttttac actgttggtg 102960
ggactgtaaa ctagttcaac cattgtggaa gtcagtgtgg cgattcctca aggatctaga 103020
actagaaata ccatttgacc cagcaattcc attactgggt atatacccaa agcattataa 103080
atcatgctgc tataaggaca catgcacacg tatgtttatt acggcactat tcacaatagc 103140
aaagacttgg aaccaaccca aatgtccaac aatgatagac tggattaaga aaatgtggca 103200
tatatacacc atggaatact atgcagccat aaaaaaggat cagctcatgt cctttgtagg 103260
gacatggatg aagctggaaa ccatcattct cagcaaacta tcgcaaggac aaaaaaccac 103320
tgcatattct cactcatagg tgggaattga acaatgagaa cacatggaca caggaagggg 103380
aacatcacac accggggcct gttgtggggt gggggagcag ggagggatag cattaggaga 103440
tatacctaat gttaaatgat gagttaatgg gtgcagcaca ccaacatggc acatgtatat 103500
atatttaact aacctgcacg ttgtgcacat ataccctaaa acttaaagta taataaataa 103560
ataaaaagaa gtttaaatcc agcctaggca acatagtgaa accctatctc aaaaataaat 103620
aaataaatac atacataatt aaaaaaataa aaaataatat aataaattag taaaattgaa 103680
gaaatctatt ttatatccac agaagttgag ttattattat aaacagattc ttaaataaat 103740
cccattaact acttaaaaaa acatttttct ctaagcacta cattagctaa atccccacaa 103800
atttgtattt gttgtatttt cactatcttt tttaaacttt tattttaagt tcaggggtac 103860
atgtgtaggt ttgctataaa ggtaaaccta tgtcatgggt gtttgttgta cagattattt 103920
catcatctag gtatgaagcc taatgcctat tagttatttt tcctgatcat ctccctttc 103980
ccatcctcca ccctccgata ggccccagtg tgtgttgttc ccctctatat gtccatgtgt 104040

```
tcttatcatt tagctcccac tattaagtga gaacatgtgg tatttggttt tctattctta 104100
tgttggtttg ccaaggataa tggcctccat ctcaactgat gtctctgcaa agtacatgat 104160
ctagttcttt tatatggttg cataatattc cgtggtgtat atgtaccaca tttcctttat 104220
ctaatctatc actaatgggc atttgggttg attccatgtc tttgctattg tgaatagtgc 104280
tgcaatgaac atacacatgc atgtgtcttt attacagaac aatttatatt cctttgggta 104340
tatactcagt aatgggattg ctgggttgaa caatatttct gtgtttaggt ctttgaggaa 104400
ttgccatact gttttccaca atgattgaac taatttacac tcccaccaac agtgtatagg 104460
tgttcctttc tctccgcaac ctcaccagca tctgttattt ttttacgttt tagtaatagc 104520
cattctgact ggtgtgagat ggtatctcgt ggtggttttg atttgcattt ccctaatgat 104580
cagtgatgtt gagctttttt tcatgattgt tggccacatg tgtgtcgtca tttaaaaagt 104640
gtctgttcat gtcctttgcc cactttttaa tggggttatt tggttttttc ttacaagttt 104700
gtttaaattc cttatagatg ctagatatta gacctctgtc agatgcatag tttgcaaaca 104760
ttttctccca ttctgtaggt tatttgttca ctctgttgat agtttccatt gctgtgcaga 104820
aattctttgg tttaattaga tcccatttga caatttttgc ttttgttgca attgcttttg 104880
gtgtcttcat catgaaatct ttcccgttc caaccaggca cggtggccca cgcctgtaat 104940
cccagcactt tggaaggccg aggtgggtgg atcacttgag cttaggagtt tgagaccagc 105000
ctggccaaca tggtgaaacc cagtctctac taaaaataca aaaatgagcc aggtgtgggg 105060
gctcatacct gcaatcccag ctactcggga ggctgaggca ggagaactgc ttgaacctgg 105120
gagatggagg ttgcagtgag ccgagatcat gccacttcac tccagactcc agcctgggtg 105180
acagagcgag actccatctc aaaaaaaaaa aaaaaaaaga aaaaaaaatc tttgcctatt 105240
cctatgtcct gaatggtatt gcttaggttg tctttcagga tttttacagt ttggggtttt 105300
gcatttaaac ctttaatcca tcttgagttt atttttgtat atggtgtaag gaaaggatcc 105360
agtttcaatt ttctgcatat ggctaaccag ttatctcagc accatttatt gaatagggtg 105420
ttctctctcc cattgcttgt ttctgtcagt tttgtcaaag accagataat tgtaggtgtg 105480
gccttatttc tgggttctcc attctgctcc attggtctat atgtctgttt ttgtaccagt 105540
accatgctgt tttgtttact gtagctgtgt agtatagttt gaagttgggt agcgtgatgc 105600
ctccagcttt gttcattttg cttaggattg ccttggctgt ttgggttctt ttatgcttcc 105660
atatgagttt taaaatagtc ttttctagtt ctgtaaataa tctatattgt agtttaataa 105720
gaatagcatt gaatctataa attgctttgg gcagtatggc catttttatg atattgattc 105780
ttcttatcca tgggcatgga atatttttca tttgtttgtg tcatctctga tttctttgag 105840
cagtgttttg tagttctctt tgtagagatc tttcagctcc ctgattagct gtattcctag 105900
gtattttatt atttttgtgg caattgtgaa taggattgca ttcctgattt ggctctcagc 105960
ttgactgtta ttagtgtata ggaatgtctg tggagaaagg atcctccatc ctcatctgat 106020
agcagtgaga ttgaatgaaa tggtatagat tgaagctagt cggactccac tttcccttcc 106080
ctcagtgtca gtgggttcca gtgagaagct gaacttatac atttactcag agacaatgaa 106140
tgtaagttag tgctcagctt tttctgtaaa ggtgtcagta gggctgagag tggagctgaa 106200
cttctaccct aagcatgtga aagaggcagt ataaattagt actctacttc tgcaggttgg 106260
tgtcagccag gcttatcagg gagctaaaca ttcactccca ccaagacctg tgtgctatac 106320
ctaagcaagg ggactgctgt taaaaaataa tattttttag aatgtaaagt ctcacattat 106380
aatattccaa atatccaaaa tataatttta aaaatcacac ataataccaa gaaccaggac 106440
```

```
aattacaact ttcatgagaa aaaataatca ttatcaacag atacaaacag tgatgaatca 106500
gatattgaag ttcacaggct atcataaaag cagcaatcat aaaaatgctc caataaataa 106560
ttgtgaattc tttgaaacaa atggaaacaa tagaaaatct cagcagaaaa ctgggaatat 106620
taaaaagaac caaagggaaa ttactgaact gtaaaaacaa taactgaaat tagcaactca 106680
ctgatgggca aaatagttaa ttaaacatga ctggagtact aaataatgaa ctcaggttgg 106740
gcgcggtgtc tcacacctgt agtcctagca ctttgggagg ctgaggtggg tggatcgctt 106800
gaggtcagga gtttgagacc agcctggcca acacggcgaa accccgtctc tactaaaaac 106860
acaaaaatta gccgggcatg gtggcacacg cttgtaatcc cagctactcg ggaggctggg 106920
gcaggagaat cacttgaacc cgggaggtgg agattgcagt gagctgagat cgcaccattg 106980
cactccagcc tggggaacag agtgacactc catctcaaaa aaagaaaaaa gaaaaaaaaa 107040
tgaactcagt gacagatacc tagcgactac acactcttaa caacatagag aaacagacta 107100
ggaaagaagg aatggggcct cagggtccta tgaggcaata ccaacagatg aaacatttat 107160
atcatcagag tcccagaaag agaaaagaaa gagtatgaga ctgaaaaata ttcaaggaaa 107220
taatggctga aattttccca aagttggcta aagttataaa cctacagatt caagaagctg 107280
agctaacata aataggatac gccaaaagaa atccatgcca gtacacatta taattaacct 107340
tctaaaaaca aaacacaaag atatgcttgc ttcaggctgg gcacagtggc tcacgcctgt 107400
aatctcagca ctttgggagg ccgaggcagg cagatcacct gagatcagga gttcgagacc 107460
agcctggcca acatgatgaa accctgtctc tactaaaaat acaaaaatta gctgggtgtg 107520
gtggtgtgtg cctgtaatcc cagctactag ggaggctgag gcaggagtat agcttgaacc 107580
tgggaggagg aggttgcagt gagccgaggt tgcaccactg cactccagcc tgggcaacag 107640
agaagattag catggcccct gtgcaaggat gacacacaaa ttcatgaaga cttccatatt 107700
gaaaaaaaca aaaaaactaa acacaaagaa aaaaatcctg aaagtagcat gtgagagaaa 107760
ggacacctta cctatagggg aaaagcaatt aaaatgacag cagatttctc atctgcaacc 107820
atgcatgtta gaaggaaatg gcataacatt cttcaagttg tgaaaaggat tgttggtgaa 107880
atctacatgt agcaagaata tcctcaggaa tgagtagaaa ataaagaatt ttatttctca 107940
gacaaatgaa aacaaagagt atttgttgtt agcaggccta cgttttaaaa tggcttaaaa 108000
tgtcaaaata ggatataaaa agcacaagga ggcttggaac tttggaaaaa gaacaatgga 108060
atgggtaaaa ataggaataa atatgaagga ctctcattcc cttcatgaat ttcttacatc 108120
atatttgata taaaaatttt gtcacatgat atggtgttta atgtatgtag aggaaatact 108180
taagagaatt atactttaaa actagagagg gatttctact tctgaaaaga tggaatagac 108240
atagttttcc ctatttctcc cattcagtac agataaaagc aaacataagt ccgtgaaaga 108300
tggagggatg aaacctgact gattaagtac atggagacct gaggaagaac atggaagctc 108360
ccttggtttt ctttttgcct tgtatatccc aaactgggtg ctagagaagc ctgcaacaca 108420
ataatgccag tgagcacagg caaaaataaa gacctaggaa agactgattg tctagtcaaa 108480
agatcaggaa agaagcaacc tagcaagaga taaaatttag atattaattt atccacccca 108540
aacactgcag aaaaagttca gtcccaggcc caccccacag atggctgcgt gggaagccta 108600
gaattctacc acccttgcca ggttttaatg aggcacattg atcaagtcag agtaagctga 108660
gtggggagct gagactttta tccttatgat ccttatccct cctccttcca cagtgtcaat 108720
ggagactatc tatggaatct agacttccag ccctatttgg gcttaacaag gcactcacat 108780
```

tcccacacat gggtgccaga ggagacctag tgaagattca ggactttcac cattacctag 108840
caagaatgaa gccacaccac tatggtgtta gtggaaacca catggggagc agtattaaga 108900
caccctggtg cctaccagcc agggtgatat tagcagaggc ctagagggga acctgaactc 108960
ctgtcccacc tagcagtaat gaagagcccc tttcctctgg tgtcaacaaa ggctgagtgg 109020
ggaacctgga ttttcaatcc tgaagcagaa gaatcacttg aaccgaggag gcagaggttg 109080
cagtgagctg agatcgtgcc attgcactcc agcctaggca acaagagtga aactccatct 109140
caaaaaaaaa gaaagaaaag aaaagacatg ttaacccaga agcctatatc cagagaagaa 109200
tatccccgtt tggagtgttc aagacattct ttttttttta agacagagtc tcactctaat 109260
gcccaggctg gggtgcagtg acactctctc agctcaccgc aacctccaca tcctgggttc 109320
aagctattct cctgcctcag cctcctgagt agctgggatt acaggtgtga accaccacgc 109380
ccagctaatt tttgtatttt tagtagagat ggggtttcac catgttggcc aggctggtct 109440
caaactcctg acctcaagtg atccacccac ctctgcctcc caaagtgctg gaattacagg 109500
cgcgagcacc gcacctggcc ccaagacatt cttaaaggaa ttaaaagtaa atttgtcacc 109560
agcagatata ccctgaaaga atggctaaaa gaagttctct aaacagaaaa ataaaacaaa 109620
gagtcttgga acatcaggaa gaaggaatga acaataagaa gagaaaaaat ataggtaaat 109680
gcagtgaact cttaaatttt ctgaataact ttattgaagc aaaaattata tcactgtcca 109740
atgtggttct caatgtatac aaaggcaata tttaagacaa ttataaatga gggcgggtag 109800
ggcgggcacg gtggcttaca cctgtagtca cagcattttg ggaggccaag gcaggtgaat 109860
cacccgaggt caggagttgg agaccagcct ggccaacatg atgaaaccct gtctctacta 109920
aaaactacaa atattagcct accgtggtga caggcgcctg taatcccagc aacttgggag 109980
gctgaggcag aagaatcact tgaacctggg aggtggaggt tgcagtgaac cgagatcaca 110040
ccattgcact ccagcctggg ggacaaagcg aaactcctct caaaaaaataa ataaataaat 110100
aaataaataa ataaatgagg gagggtaaaa ggatgtaaag gtaaaatgaa gtttctacac 110160
atcactggga ctggtaaaac aatattcagg aaactggcaa gatataacta ttttatttat 110220
tttttgagat ggattacagg cacgcgccac cacgcccagc taattttttt attttactag 110280
agatggggtt ttgccatgtt ggccaggcta gccttgaact cctgacctca gatgatgcac 110340
ctgcctcagc cttcccaaag tgctgggatt acagccgtga gccactgcgc ccggctaata 110400
taactttttt tttaatggtt ttttaatggt ttaactggaa gttgctccta agggcataca 110460
gcaaatcaag aaatatttat tcaagaaagt catggttaga gcagctagag tctgtggcac 110520
ttaaaccgtg gcacactctc tccatcccct acccccagct cagatttttt ggaagctcca 110580
ttctgggtag ttgtggccat gaagacaggg accccctctcc ttcagctcct aatcagggga 110640
tatggcatat cacaggaggg ataggtttcc agcattcatc atcctctttc attccacgtt 110700
gaagagacta taattcctgg tgagactgag accttacccc actcaacacc cactcctagg 110760
gtggaagctc taccccagct gaacacacca gaacaaatag gcagaatatc acaatagatg 110820
atgtaactcc caagtagttc taacagaaca ctccatcttt aacgatggaa aaatacacat 110880
tcttctcaaa agcacatgga acattttttg ggatagacca catgtaaagt aatcaaacaa 110940
gcctcaataa gtcaaaaaga ttaaaacaag acaaagtatg tctttgacca caattaagta 111000
aaattataaa ttaataacaa tgaaaatttg gaaattcaca aatatataga aatttaaaaa 111060
tacattttta accaatgggt gaaagaaatg aaaatgaagc cacaacatac caaaacttaa 111120
gggatgcagc taaagcactg cttagataga attctttttt tttttttga gatggagttt 111180

```
cgctcttatt gcccaggctg gagtgcagta gtgccatctc agctcactgc aacctccgcc 111240
gcccgggttc aagcgattct cctgcctcag ccacccaagt agctggaact acaggcgcct 111300
gccaccacgc ccagctaatt ttttgtattt ttagtaggga tggggtttca ccatgttggc 111360
caggctggtc tcaaactcct gacctcaggt gatccgcctg cctcggcctc ccaaagacca 111420
gggattacat gggagagcca ctgcacccgg ccttagatag aaattgatag ctgtaaatgc 111480
ctactttaaa aatgaagaaa gataccggcc acatggtggc tcatgcctgt aatcccagca 111540
ctttgggagg ccaaggcggg cggatcacga ggtcaggaca tcgagaccat cctggctaac 111600
acggagaaac cccatctcta ctaaaaatac caaaaattag ctgggcgcag tggcgggctc 111660
ctgtagtccc aactactcag gaggctgagg caggagaatg gcgtgaacct gggaggcaga 111720
gcttgcagtg agccgagatt gcgcccctgc gctccagcct tggccacaga gcgagactcc 111780
atctcaaaaa aaaaaaaaaa aaaaaagaag aagaaacata ccaaatgaat aacctaacct 111840
ttcacagtaa gacactggaa aaagaagagc aaatgaaaag caaggagaag gaaggaaata 111900
ataaagtgta gagttaaaat cattaaaata gtgatagtaa aaataaagaa aagaaatgca 111960
gtctaagtag tttatttgaa aagatcaatg aaattgacaa acatgtagct agactgaaca 112020
aacaaaaaag acgaaactaa aatcagaaat gacaaagggg acattactac ctaccttagg 112080
gaaataaaaa tgattaaaag gaaatactat aaaactgttt gccaacaaat tagacaactt 112140
agatgaaatg aacacattct tagaatgata caaattactg aatctgacca aggaagaaat 112200
agaaaatctg aacataccaa agtatcaggc cgttcttgtg ttgtcacaga ggaatatctg 112260
aggctgggta atttataaag aaaagaagtt taattggctc atgtttcctc agggtataca 112320
ggcatggcac cagcatatgc ttggcttctg atgaggcctc agaaagctta caatcattgt 112380
gaagccaaag ggagagcaag tatgtcacat ggcaagagca ggagaaagag agagggagaa 112440
tgatgccaca caaccaaatc ttgcatgaac tcagagcagc aactcactta tcaccaaggg 112500
gatggagcta agccattctt tgattattat catcatcatc atcatcatca tcatcattgc 112560
agggagccga aggcccgtga gacgtgacca actcagcatt ttgctggagg ctatatgatc 112620
aaacagcaga ctgtttatca tgaatgcagg atgtgggcaa actcacactg ccctgccacc 112680
aaaaggtttg ctgagagaca tcactccctg gcacggggtt ccttgcagtt atctactgag 112740
aaaattagtg cctattgttc aaaggatgca gtctcacaag cctgctgtga accaaagctg 112800
gctgacaatt acccaacaat cacccccacc tttcctgctg tctcttttgc ctaataaata 112860
cggagggctg tgtaaagctc agggcccttg tccactagag gcaaggtgcc ccctgacccc 112920
ttcttccaaa tagattcttt tgtctcttgt cttttattct catgttcacc cccgctttgt 112980
tcagtcctcc taggtccgtg caggctacaa gtggcgcccc gaacagcgac agaatcgggt 113040
gctctatggt tattttgaga caaggtcttg ctctgtcacc caagctggag tacagtggtg 113100
tgatcactgc taactgcagc cttgacctcc tgggctcaag caatcctccc acctcagcct 113160
cccaagtagc tgggaccata ggcacatacc actacatctg gctaaattta aacttttttg 113220
aagagatggg gtcccactat gttgtccagc ctggtcttga actcctggcc tagagcaatt 113280
ctcctgcctc ggcctcccaa agtgctggta ttataggcat gagccaccac ccctggccta 113340
aaccattctt gagggatctg cccccgtgat ctactcacct cccactagcc cccacctcca 113400
acatttggaa tcacatttca acttgagatc taaggggaca aacatccaaa ccatatcaac 113460
gtataacaag aaaatagata gaattcataa tgaaaacact acctacaaag ataagttcag 113520
```

```
tcccagatgc cttcactggt aaattctacc acacacttaa agatgaattc aggcctggca 113580

tggtggctca cgcctgtaat cccagcactt tgggaggctg aggcaggtgg atcacgaggt 113640

aaggagttca agaccagcct gaccaagatg gtgaaacctc gtctctacta aaaatacaaa 113700

aattagccgg gcacggtggc aggagcctgc aatcccagct acttgggagg ctgaggcagg 113760

agaatcactt gaacccagaa ggcagaagtt gcagtgagcc gagattgtgc cactctactc 113820

cagcctgggt gacagtaaga atctgtctca aaaaaaaaaa aaagatgaat ccatagcaat 113880

tcttcgcaaa ttcttctaag aaacaaaaga ggagaaaact ctttccaact cagtctttga 113940

agcaaatatt gcttcgatat taaaatcaga aaaagccatc acgaaaaaac tacaagtcaa 114000

tatatcttat gaaataggtg caaatccctc aattaaaaac tagcaaacta aatccaacaa 114060

cataaaaaag ggctaaatac cacattcaag tggaatttat cccagaaatt caagattaat 114120

ttaacatcca aaaatcaata taatgcatca tattggtgga acaaagaaca aaccccacag 114180

gattatcttc atattcagaa agagcatttg acaacattta agtggttctg ttccacttga 114240

agatttatat cttcaagatg aaaatattca acgacaaact aggaggagaa ggtaacttta 114300

ttgtgatggt taattttatt tgtcaactta agtaggctag gggataccca gatagcgggt 114360

aagacattat taatggctgt gtctgtgagg gtgtttctga aaaagattag catttgaatc 114420

agtagactga gtgaaaaaaa tcaccctcac caatgtgggc cgcatccaat ccactcaggg 114480

cccaaataaa acataaaagt agaagaaggg tgaattc                          114517
```

```
<210> SEQ ID NO 14
<211> LENGTH: 87
<212> TYPE: RNA
<213> ORGANISM: Artificial Sequence
<220> FEATURE:
<223> OTHER INFORMATION: Let-7f miRNA inhibitor with hairpin structure
      synthesized by Dharmacon

<400> SEQUENCE: 14

ucagagugag guaguagauu guauaguugu gggguaguga uuuuacccug uucaggagau     60

aacuauacaa ucuauugccu ucccuga                                          87


<210> SEQ ID NO 15
<211> LENGTH: 8
<212> TYPE: DNA
<213> ORGANISM: Artificial Sequence
<220> FEATURE:
<223> OTHER INFORMATION: CREB binding site in promoter of Let-7f miRNA
      gene

<400> SEQUENCE: 15

tgacggct                                                                8


<210> SEQ ID NO 16
<211> LENGTH: 8
<212> TYPE: DNA
<213> ORGANISM: Artificial Sequence
<220> FEATURE:
<223> OTHER INFORMATION: CREB binding site in promoter of Let-7f miRNA
      gene

<400> SEQUENCE: 16

tgaagtct                                                                8


<210> SEQ ID NO 17
<211> LENGTH: 8
<212> TYPE: DNA
```

<213> ORGANISM: Artificial Sequence
<220> FEATURE:
<223> OTHER INFORMATION: CREB binding site in promoter of Let-7f miRNA gene

<400> SEQUENCE: 17 tgaagtca 8

<210> SEQ ID NO 18
<211> LENGTH: 10221
<212> TYPE: DNA
<213> ORGANISM: Artificial Sequence
<220> FEATURE:
<223> OTHER INFORMATION: CREB mRNA GenBank Accession No.: NM_134442

<400> SEQUENCE: 18
tgtttccgtg cgcggccgct gcgcactcgg cactgggcgg cgctggctgg ctccctggct 60
gcggctcctc agtcggcggc ggctgctgct gcctgtggcc cgggcggctg ggagaagcgg 120
agtgttggtg agtgacgcgg cggaggtgta gtttgacgcg gtgtgttacg tgggggagag 180
aataaaactc cagcgagatc cgggccgtga acgaaagcag tgacggagga gcttgtacca 240
ccggtaacta aatgaccatg gaatctggag ccgagaacca gcagagtgga gatgcagctg 300
taacagaagc tgaaaaccaa caaatgacag ttcaagccca gccacagatt gccacattag 360
cccaggtatc tatgccagca gctcatgcaa catcatctgc tcccaccgta actctagtac 420
agctgcccaa tgggcagaca gttcaagtcc atggagtcat tcaggcggcc cagccatcag 480
ttattcagtc tccacaagtc caaacagttc agtcttcctg taaggactta aaaagacttt 540
tctccggaac acagatttca actattgcag aaagtgaaga ttcacaggag tcagtggata 600
gtgtaactga ttcccaaaag cgaagggaaa ttctttcaag gaggccttcc tacaggaaaa 660
ttttgaatga cttatcttct gatgcaccag gagtgccaag gattgaagaa gagaagtctg 720
aagaggagac ttcagcacct gccatcacca ctgtaacggt gccaactcca atttaccaaa 780
ctagcagtgg acagtatatt gccattaccc agggaggagc aatacagctg gctaacaatg 840
gtaccgatgg ggtacagggc ctgcaaacat taaccatgac caatgcagca gccactcagc 900
cgggtactac cattctacag tatgcacaga ccactgatgg acagcagatc ttagtgccca 960
gcaaccaagt tgttgttcaa gctgcctctg gagacgtaca aacataccag attcgcacag 1020
cacccactag cactattgcc cctggagttg ttatggcatc ctccccagca cttcctacac 1080
agcctgctga agaagcagca cgaaagagag aggtccgtct aatgaagaac agggaagcag 1140
ctcgagagtg tcgtagaaag aagaaagaat atgtgaaatg tttagaaaac agagtggcag 1200
tgcttgaaaa tcaaaacaag acattgattg aggagctaaa agcacttaag gacctttact 1260
gccacaaatc agattaattt gggatttaaa ttttcacctg ttaaggtgga aaatggactg 1320
gcttggccac aacctgaaag acaaaataaa cattttattt tctaaacatt tcttttttc 1380 tatgcgcaaa actgcctgaa agcaactaca gaatttcatt catttgtgct tttgcattaa 1440
actgtgaatg ttccaacacc tgcctccact tctcccctca agaaattttc aacgccagga 1500
atcatgaaga gacttctgct tttcaacccc caccctcctc aagaagtaat aatttgttta 1560
cttgtaaatt gatgggagaa atgaggaaaa gaaaatcttt ttaaaaatga tttcaaggtt 1620
tgtgctgagc tccttgattg ccttagggac agaattaccc cagcctcttg agctgaagta 1680
atgtgtgggc cgcatgcata aagtaagtaa ggtgcaatga agaagtgttg attgccaaat 1740
tgacatgttg tcacattctc attgtgaatt atgtaaagtt gttaagagac ataccctcta 1800

```
aaaaagaact ttagcatggt attgaaggaa ttagaaatga atttggagtg ctttttatgt   1860
atgttgtctt cttcaatact gaaaatttgt ccttggttct taaaagcatt ctgtactaat   1920
acagctcttc catagggcag ttgttgcttc ttaattcagt tctgtatgtg ttcaacattt   1980
ttgaatacat taaaagaagt aaccaactga acgacaaagc atggtatttg aattttaaat   2040
taaagcaaag taaataaaag tacaaagcat attttagtta gtactaaatt cttagtaaaa   2100
tgctgatcag taaaccaatc ccttgagtta tataacaaga tttttaaata aatgttattg   2160
tcctcacctt caaaaatatt tatattgtca ctcatttacg taaaaagata tttctaattt   2220
actgttgccc attgcactta cataccacca ccaagaaagc cttcaagatg tcaaataaag   2280
caaagtgata tatatttgtt tatgaaatgt tacatgtaga aaaatactga ttttaaatat   2340
tttccatatt aacaatttaa cagagaatct ctagtgaatt ttttaaatga aagaagttgt   2400
aaggatataa aaagtacagt gttagatgtg cacaaggaaa gttattttca gacatatttg   2460
aatgactgct gtactgcaat atttggattg tcattcttac aaaacatttt tttgttctct   2520
tgtaaaaaga gtagttatta gttctgcttt agctttccaa tatgctgtat agcctttgtc   2580
attttataat tttaattcct gattaaaaca gtctgtattt gtgtatatca tacattgttt   2640
tcaataccac ttttaattgt tactcatttt attcactaag ctcgataaat ctaacagtta   2700
ctcttaaaaa aaaaaaaaaa agactaaggt ggattttaaa aattggaaac tgacataatg   2760
ttaggttata atttctcatt tggagccggg cgcagtggct cacgcctgta atcccagcac   2820
tttgggaggc caaggtgggt ggatcacctg tggtcaagag ttcaagacca gcctggccat   2880
catggtgaaa ccccatctct actaaaaata caaaaattag ccaggcgtgg tggctggcgc   2940
ctgtaatccc agctactcag gaggttgagg cagcagaatt gcttgaaccc aggaggcaga   3000
gggttgcagt gagccgagat agcaccattg cactccagcc tgggcgactc catctcaaaa   3060
aataaaaata aaaaaaatgt ctcatttggg aaggaaattc cttttaaaaa agagttgaga   3120
cacttagaaa actaatgttt tatatttagt caagagttat ttaagaaagt caagcttgtt   3180
taacaacaaa atatgaagat ttaagtgtta attgctggat ccattttaaa ataagatttt   3240
aattaacatt tgtaaatggt atattttcgt ttgtaacaaa ccattgtctt ttttcaagga   3300
tgaacagagt ttatgaagga gcatcattct aagaattaag tgatgtagtc tttatgtttg   3360
gacagttcac cagattctca agaaggcttt caaacaacta taaagtttga tgtttgtcct   3420
gctgagctaa tggggaaagt tatagcataa aaattgtgta accgcataga tatgtcattt   3480
ttaaaaactg gtttaacaga aatcaagcaa agtcacaaat atgttcacaa gttggaatta   3540
tttattgagt caaaatgtcg aatcgaacat tttgaatgaa gtaagtgtta taaatgaaaa   3600
attgcctgat gtttagcagt ttgtattctc taaagctttt tttcaaaagt tcaggctttc   3660
tacttactgg gaagttggtg gtcctcttag tccctgataa atcaaggcaa tcacattcat   3720
gtgagctgga tgaatttata agttataaag accttatcct tcataccttg aggatgattg   3780
cactggtttt gaagtcagtt gcttaatgat gaggtgagaa atgtatcctg ttgctaaatc   3840
tgtcttagac ccttggtgaa acttgaagat ttcagtttat aaagataaaa tcaagcatct   3900
tttgtgcagt tttcttttt taatgcaaga atggtgggga ggtttgtttg taagcatgaa   3960
actttgagaa tctttattaa gaaaatgaca taatttttaa aaaccttgta gccaagaaca   4020
tatgtggcca cattaccagt aataaatgtt tttctcttta tattggccaa aagggaataa   4080
aaatgtcatc ataggaattt gtacatatgc tactgatttg cctagaaaat agcaagtttg   4140
atattgctca ctttgcaaat atagggccat gtggcacttt tatctatagg acagattaat   4200
```

```
aaaaatgaag tggggagggg tttatttttg atatattact cttatgagtt ttcaagcttt   4260
gataatgttt aactgaaaag tggcttagaa agggctagat ccaatgtgtt cattattaaa   4320
taattgctat cagatacaat tttaagttca ttctttttca aactcaagta ccatattggc   4380
aaccataata ttgtcatagg tgctctcttc atttagatat tcttgggggg ggtggcattt   4440
gtataaatata tgtgtacata tatatatata tatatatata tacatacagt atataatcta   4500
aagctctgag agctcttaag tcaggaatgc tgagtattat agtatattga ggtcagatga   4560
aattttacat ttttgtgtgt tctgttgcat tccttctggt agtttctatg actgcattac   4620
tccagcactc atgattgatt ttatcttcta attttcttcc aagtatttta tttttttatta   4680
gttttctttg gcttgatact tttaaatatg ttactagtca cttgaaagcc tctcccccaa   4740
aagtatttgg tttgtatgct ttgtctgtgg cagctataac agtggtaaga acattttgaa   4800
gatagctttt taaaggaacc actgattttt tcaaaaatca tcctggggga ggaattttgg   4860
catttcattt gagcagggat tttgtcagaa aatgtgtttt gatggtaggt cagcagcagt   4920
gctagtctct gaaagcacaa taccagtcag gcagcctatc ccatcagatg tcatctggct   4980
gaagtttatc tctgtctctc aggataaatc cctgtaggac aaatccctac tatcatttct   5040
accttttggg gtgacatgtg gaatcataca aaggcttagg aagaaatacg tttgtttaaa   5100
ccaggatgct ttacttactt gaagtgactt caatctagat ttcttttaat atttaacaaa   5160
tttttaattc tatgatcagc cacagtcagc tattaccata aattggtctc tgtttatttt   5220
gaagatcacg gctgcttcat tttgcaggat taagtagggc taatgtatct taaagttaag   5280
atcttgaatt aaagtgagtt ttagaaatag tgttacatac cttttcagtt gttttcaaga   5340
ggctttattt ttgttgcctt tgtagccctg aaagctgttg gtatattttt tccctcatgg   5400
acccaataga aaagttgtat atttatttgg attatattta cattctgtcc tttgtaaatg   5460
tttggtgtaa cttgcacttt tttaaatgac ccagtttggg tattagcaac ttaagaaatt   5520
ccctcatcaa gtaattctca actttttagt ctttctcctc tcttcaaatc atgtgacttt   5580
ttaaatggaa gtttttcatt gattaaaata ttttagcacc taaaagctag ccttaaaaac   5640
agctgtaaaa gaaaaacatc aggaaattag atatgactag cccagttaat taaaagacgg   5700
gctcaaacct tgttttattc tttttcatct tggatgaaga ttgaagggaa aataactcaa   5760
gtgcataata tttattttca atttttaatg agactttatc ctcatcacaa cattaatact   5820
gtacatagta tgccaaaata tccattaatt tgtctagaat agtacaagac tttttaaagc   5880
aattgtcctc acagagacca catgtaatat actgaaatat gttcattttt aatggctttg   5940
ttaacatcaa agaaatgctg cctaaatttg atttcagatg aggaaggaga aagtaaagtg   6000
tgcatagtaa ggctgtaggt gaagagttgt gagataaata gttcactcag ttgtacaaag   6060
cacaactaga actttttgtt gggaggctta catacatctt gaatattctt aatgtaataa   6120
tgttgactat taagttggct acacagtcac tgtatgtact aggaactggt ttccttgaca   6180
ttctagaatc aatggctagg agaggcatta atctttgagg ggctgaacat atcatgaagc   6240
tgagtcagta tggaaaattt tcaaataaac agggtgctga agttccatct gtctcatctg   6300
cttatgataa gttcttattg attagtgaat gtagcttaag cctttgtatg tgtcctcagg   6360
gggcagaccg actttaagag ggaccagata acgtttgaat ggagggatta tatttcaggt   6420
gttttagctt gaaatttatt ttttaaaaaa agaaaaattt aaaaaatata taaataaaat   6480
agaacaaagc cggtgatgca agttgatatt ataaacaggc agttttagca cagaaagaaa   6540
```

```
atactgacct gtctgcattc tggtacggtg ggtgcaggtc ccagctgggt atgacatgat   6600
acatttttaa ttattctcac cagcaagtaa aaggaaaatg aacaatcttt tggaattgtc   6660
tttgaaaagg atcaaagagt aggaaattca catttgacct aacattactt gcctatagaa   6720
gtatggcatt tccaagcttt tgtctgagga gcatctcaga gaagtgagag taaatctgag   6780
ttagcttaaa aattggtagg gaggaagaaa atctctgcaa ataatgattt tatgtttgtt   6840
ggccaagtga aatgatctat cattgtgttt gggaggtttt attttcttat gtttttaaaa   6900
ttggtaaatg ctttatagat gtatttttat ccaagtgcca ctccaatttg tgtatgtaat   6960
aaaattattt atattaaaag tgggaaataa ttgtcaacat ttttttgag tatagattta   7020
ttaggggtgg caaagaagag tgctagttag cagttttcca tgtaaagttg tccttgactg   7080
atttgtccac atgtcagttg taactccccc actccctgca aaaggaatta tttctaaccc   7140
agatgtatca cttgaaactt tttagaagca aaataatcag ggaagttcct agaaaggtgt   7200
ttggcttttt ggtttttgag ggttggggta aagaagactt cccccacaac tgtcagcaca   7260
aaacagggta ttgattttta actctgatgt ttctattgga gttgaatact aaataaataa   7320
ctataatgag ggaaatacat ttctaataaa attccctaca ttctagaaac atccctgttt   7380
taattttttt atctaaatct ttttgtgctt tatgtgtaaa gaaaaaaatg tactgagtta   7440
caatgcattt tattaacact atgtacataa tagctgcttt gtgttcagaa tagtagcagt   7500
tgctttgtat attaaagtga tccttgtgaa tttgtgaaat attgtcataa agtgcttttt   7560
cttactgtaa tctttgtggt atcaactgtc ataatgctct ttttacacaa acatttatgt   7620
gcagtcacat aaacatgctt ttaaaaactc tgtaagtctc tttttgggg atgggatctc   7680
tatattttgt tgggtttttt ttgctagtag tgtgaagcca tgttttattg gacttaaagt   7740
tacaatatat tacaagcttg tgttggaagg cagcaaaact aattcagaca acaacatgtc   7800
ttcagttact ggatccctaa ttttcaggac aaaacctgtt tttcaataag attgaacagt   7860
gcctatttgt ggatttggag atgttactgt caagatgact aatggagaca tacgaccagc   7920
tgtgtctgat gtcataaaac acgtgttcac tgaaaggaca ataagactat ataccttctc   7980
aggtcccctt gcaattctaa aactctgtga tcatataaat tggaaggaaa ggggagggga   8040
tatggttaat ctttgcttaa gctgtaagaa taaaaaagtt atctcctata ctattaactt   8100
ctgaaataag ttctgagacg agacatctga aaataagcag ctgcattatt tgtatgtttc   8160
ttcactgcca agatgtgttc aagcctgcta tacctgccat tgtattggaa ggcttaatga   8220
atttcattta ttttctgcaa caacgattac agaatttatt gcacaaaatg agacattttg   8280
agagtgatat taattacatg agggacaata ggcatgaact aggattgttc taagcaaatc   8340
ggaatcgggt caccctgcca cgttcaggtg cttggacctt caggaaaaga ttgcccatct   8400
tgtcatttga ccaggcactg aagtgacaag accatccttg agaagtcaca tccaaagata   8460
aaattctgat ccatttctag ttttagtgtt tcgccactga agacttaaca tatgtctttt   8520
acactcaggt tgcaaaacac aggcccaaga caaacttaac ttctccccca aatcttcctt   8580
ccgctggttt ttccatctcg taagtggtgc cactatccat ctgttaaatt gtttagggga   8640
aacctagaaa agcactacct taatcagtgt tatccttctt cttaactgtg cgtcctaatt   8700
tctccacatc tttcttaagt gcagtgacca aaccggatga gaattctaac acgggcctga   8760
catcaaatgg aaaggaagga taatgtccag gagttggaat gttatccttg tttttaatta   8820
agatgcaatt cacataaatt aactttttaa gtgaacaatt aagtggtagt acatccacaa   8880
tggtgtacaa ccaccacttc tatctagctc caaaacattc tcatcactcc aaaagtaaag   8940
```

```
tcccgttact ctccattttc tcctcccacc gcccttgtcc ctggcaacca ccaatctgct   9000

tcctgtttct ttggatttac atccgggtat ttcatgtgag actcatacac tgtgtattac   9060

ttctttcgtc tagctttaat gtgttgttga ggttgatcca ttgtaacatg ttatcactac   9120

ttcattcctt tttatagcta agtatacttt ttatagtaag tatgccattg tagatatata   9180

ccacaagttt atcgattcat ccagttgagt tgtttctact gtttggctaa tgttcatagt   9240

gctgttatga atgttcgtgt acaagtattt gagtccgtgt tttcaattat ttggggtata   9300

tgcctgggag tggagttgct gggtcatgtt gaaatcgcac atttaacttt ttgaggaact   9360

gtcaaacttt ccctcagcag ctgtaccgtt ttaccttcca ccattgatgt atgagggttc   9420

caatttctcc acaccttcac caacacttat tttgccattt taaaaattat agccatcctc   9480

atgggtgtgg tctctcattg tggttttgat ttgcatttcc ctgattacta atgatgtgga   9540

gcatcttttg ttgtctttgg ccatctgcgt atcttctttg aagaaatgtc tgttgaggtc   9600

ctttgttcat tgaaattttg ttgttgggtt ctgagttcct tatatattct gggtactagg   9660

cccttataat attttcgcct ataagttttt gctttataat gtcctcattg ttttcaaact   9720

tactttatgt aatatgtaca cttctaaaaa aaagaaacat ggaaaagggc aaactgtaag   9780

aagtttttttg tgttatgttt tttgtgacag tctgtgcata tatacacaaa tataatgtat   9840

gttctctcct cctccctctc ccttttttta cacaaaaggt aggtacaaac agtggtttat   9900

aaactgctgc cattgtacag atacagttta accagtcctc ttctggggac atttggctgt   9960

ttgaaatttt ttactgttac agatatacag aggttggtaa ctaggtctac acaagttgta  10020

tctccaggat actgagaagt aaaagttatt tctgaattat ggttttcttc atatttggat  10080

attgtttcct aatgattatt aggtatctgc taagcaattt ttattaactt atgttgatta  10140

ctatttttat gtcaaacttt acagtctagg catttttttc tggaattaaa attagaagtg  10200

gcacagacaa aaaaaaaaaa a                                            10221
```

<210> SEQ ID NO 19
<211> LENGTH: 1026
<212> TYPE: DNA
<213> ORGANISM: Artificial Sequence
<220> FEATURE:
<223> OTHER INFORMATION: CREB Open reading Frame

<400> SEQUENCE: 19

```
atgaccatgg aatctggagc cgagaaccag cagagtggag atgcagctgt aacagaagct     60

gaaaaccaac aaatgacagt tcaagcccag ccacagattg ccacattagc ccaggtatct    120

atgccagcag ctcatgcaac atcatctgct cccaccgtaa ctctagtaca gctgcccaat    180

gggcagacag ttcaagtcca tggagtcatt caggcggccc agccatcagt tattcagtct    240

ccacaagtcc aaacagttca gtcttcctgt aaggacttaa aaagactttt ctccggaaca    300

cagatttcaa ctattgcaga aagtgaagat tcacaggagt cagtggatag tgtaactgat    360

tcccaaaagc gaagggaaat tctttcaagg aggccttcct acaggaaaat tttgaatgac    420

ttatcttctg atgcaccagg agtgccaagg attgaagaag agaagtctga agaggagact    480

tcagcacctg ccatcaccac tgtaacggtg ccaactccaa tttaccaaac tagcagtgga    540

cagtatattg ccattaccca gggaggagca atacagctgg ctaacaatgg taccgatggg    600

gtacagggcc tgcaaacatt aaccatgacc aatgcagcag ccactcagcc gggtactacc    660

attctacagt atgcacagac cactgatgga cagcagatct tagtgcccag caaccaagtt    720
```

```
gttgttcaag ctgcctctgg agacgtacaa acataccaga ttcgcacagc acccactagc    780

actattgccc ctggagttgt tatggcatcc tccccagcac ttcctacaca gcctgctgaa    840

gaagcagcac gaaagagaga ggtccgtcta atgaagaaca gggaagcagc tcgagagtgt    900

cgtagaaaga agaaagaata tgtgaaatgt ttagaaaaca gagtggcagt gcttgaaaat    960

caaaacaaga cattgattga ggagctaaaa gcacttaagg acctttactg ccacaaatca   1020

gattaa                                                              1026
```

```
<210> SEQ ID NO 20
<211> LENGTH: 251
<212> TYPE: DNA
<213> ORGANISM: Artificial Sequence
<220> FEATURE:
<223> OTHER INFORMATION: CREB 5'UTR

<400> SEQUENCE: 20

tgtttccgtg cgcggccgct gcgcactcgg cactgggcgg cgctggctgg ctccctggct     60

gcggctcctc agtcggcggc ggctgctgct gcctgtggcc cgggcggctg ggagaagcgg    120

agtgttggtg agtgacgcgg cggaggtgta gtttgacgcg gtgtgttacg tgggggagag    180

aataaaactc cagcgagatc cgggccgtga acgaaagcag tgacggagga gcttgtacca    240

ccggtaacta a                                                         251
```

```
<210> SEQ ID NO 21
<211> LENGTH: 8944
<212> TYPE: DNA
<213> ORGANISM: Artificial Sequence
<220> FEATURE:
<223> OTHER INFORMATION: CREB 3'UTR

<400> SEQUENCE: 21

tttgggattt aaattttcac ctgttaaggt ggaaaatgga ctggcttggc cacaacctga     60

aagacaaaat aaacatttta ttttctaaac atttcttttt ttctatgcgc aaaactgcct    120

gaaagcaact acagaatttc attcatttgt gcttttgcat taaactgtga atgttccaac    180

acctgcctcc acttctcccc tcaagaaatt ttcaacgcca ggaatcatga agagacttct    240

gcttttcaac ccccaccctc ctcaagaagt aataatttgt ttacttgtaa attgatggga    300

gaaatgagga aaagaaaatc tttttaaaaa tgatttcaag gtttgtgctg agctccttga    360

ttgccttagg gacagaatta ccccagcctc ttgagctgaa gtaatgtgtg ggccgcatgc    420

ataaagtaag taaggtgcaa tgaagaagtg ttgattgcca aattgacatg ttgtcacatt    480

ctcattgtga attatgtaaa gttgttaaga gacataccct ctaaaaaaga actttagcat    540

ggtattgaag gaattagaaa tgaatttgga gtgcttttta tgtatgttgt cttcttcaat    600

actgaaaatt tgtccttggt tcttaaaagc attctgtact aatacagctc ttccataggg    660

cagttgttgc ttcttaattc agttctgtat gtgttcaaca tttttgaata cattaaaaga    720

agtaaccaac tgaacgacaa agcatggtat ttgaatttta aattaaagca aagtaaataa    780

aagtacaaag catattttag ttagtactaa attcttagta aaatgctgat cagtaaacca    840

atcccttgag ttatataaca agatttttaa ataaatgtta ttgtcctcac cttcaaaaat    900

atttatattg tcactcattt acgtaaaaag atatttctaa tttactgttg cccattgcac    960

ttacatacca ccaccaagaa agccttcaag atgtcaaata aagcaaagtg atatatattt   1020

gtttatgaaa tgttacatgt agaaaaatac tgattttaaa tattttccat attaacaatt   1080

taacagagaa tctctagtga attttttaaa tgaaagaagt tgtaaggata taaaaagtac   1140
```

```
agtgttagat gtgcacaagg aaagttattt tcagacatat ttgaatgact gctgtactgc   1200
aatatttgga ttgtcattct tacaaaacat ttttttgttc tcttgtaaaa agagtagtta   1260
ttagttctgc tttagctttc caatatgctg tatagccttt gtcattttat aattttaatt   1320
cctgattaaa acagtctgta tttgtgtata tcatacattg ttttcaatac cacttttaat   1380
tgttactcat tttattcact aagctcgata aatctaacag ttactcttaa aaaaaaaaaa   1440
aaaagactaa ggtggatttt aaaaattgga aactgacata atgttaggtt ataatttctc   1500
atttggagcc gggcgcagtg gctcacgcct gtaatcccag cactttggga ggccaaggtg   1560
ggtggatcac ctgtggtcaa gagttcaaga ccagcctggc catcatggtg aaaccccatc   1620
tctactaaaa atacaaaaat tagccaggcg tggtggctgg cgcctgtaat cccagctact   1680
caggaggttg aggcagcaga attgcttgaa cccaggaggc agagggttgc agtgagccga   1740
gatagcacca ttgcactcca gcctgggcga ctccatctca aaaaataaaa ataaaaaaaa   1800
tgtctcattt gggaaggaaa ttccttttaa aaaagagttg agacacttag aaaactaatg   1860
ttttatattt agtcaagagt tatttaagaa agtcaagctt gtttaacaac aaaatatgaa   1920
gatttaagtg ttaattgctg gatccatttt aaaataagat tttaattaac atttgtaaat   1980
ggtatatttt cgtttgtaac aaaccattgt ctttttttcaa ggatgaacag agtttatgaa   2040
ggagcatcat tctaagaatt aagtgatgta gtctttatgt ttggacagtt caccagattc   2100
tcaagaaggc tttcaaacaa ctataaagtt tgatgtttgt cctgctgagc taatggggaa   2160
agttatagca taaaaattgt gtaaccgcat agatatgtca tttttaaaaa ctggtttaac   2220
agaaatcaag caaagtcaca aatatgttca caagttggaa ttatttattg agtcaaaatg   2280
tcgaatcgaa cattttgaat gaagtaagtg ttataaatga aaaattgcct gatgtttagc   2340
agtttgtatt ctctaaagct ttttttcaaa agttcaggct ttctacttac tgggaagttg   2400
gtggtcctct tagtccctga taaatcaagg caatcacatt catgtgagct ggatgaattt   2460
ataagttata aagaccttat ccttcatacc ttgaggatga ttgcactggt tttgaagtca   2520
gttgcttaat gatgaggtga gaaatgtatc ctgttgctaa atctgtctta gacccttggt   2580
gaaacttgaa gatttcagtt tataaagata aaatcaagca tcttttgtgc agttttcttt   2640
ttttaatgca agaatggtgg ggaggtttgt ttgtaagcat gaaactttga gaatctttat   2700
taagaaaatg acataatttt taaaaacctt gtagccaaga acatatgtgg ccacattacc   2760
agtaataaat gtttttctct ttatattggc caaaagggaa taaaaatgtc atcataggaa   2820
tttgtacata tgctactgat ttgcctagaa aatagcaagt ttgatattgc tcactttgca   2880
aatatagggc catgtggcac ttttatctat aggacagatt aataaaaatg aagtggggag   2940
gggtttattt ttgatatatt actcttatga gttttcaagc tttgataatg tttaactgaa   3000
aagtggctta gaaagggcta gatccaatgt gttcattatt aaataattgc tatcagatac   3060
aattttaagt tcattctttt tcaaactcaa gtaccatatt ggcaaccata atattgtcat   3120
aggtgctctc ttcatttaga tattcttggg gggggtggca tttgtataat atatgtgtac   3180
atatatatat atatatatat atatacatac agtatataat ctaaagctct gagagctctt   3240
aagtcaggaa tgctgagtat tatagtatat tgaggtcaga tgaaatttta catttttgtg   3300
tgttctgttg cattccttct ggtagtttct atgactgcat tactccagca ctcatgattg   3360
attttatctt ctaattttct tccaagtatt ttattttttta ttagttttct ttggcttgat   3420
acttttaaat atgttactag tcacttgaaa gcctctcccc caaaagtatt tggtttgtat   3480
```

```
gctttgtctg tggcagctat aacagtggta agaacatttt gaagatagct ttttaaagga   3540
accactgatt ttttcaaaaa tcatcctggg ggaggaattt tggcatttca tttgagcagg   3600
gattttgtca gaaaatgtgt tttgatggta ggtcagcagc agtgctagtc tctgaaagca   3660
caataccagt caggcagcct atcccatcag atgtcatctg gctgaagttt atctctgtct   3720
ctcaggataa atccctgtag gacaaatccc tactatcatt tctacctttt ggggtgacat   3780
gtggaatcat acaaaggctt aggaagaaat acgtttgttt aaaccaggat gctttactta   3840
cttgaagtga cttcaatcta gatttctttt aatatttaac aaatttttaa ttctatgatc   3900
agccacagtc agctattacc ataaattggt ctctgtttat tttgaagatc acggctgctt   3960
cattttgcag gattaagtag ggctaatgta tcttaaagtt aagatcttga attaaagtga   4020
gttttagaaa tagtgttaca taccttttca gttgttttca agaggcttta tttttgttgc   4080
ctttgtagcc ctgaaagctg ttggtatatt ttttccctca tggacccaat agaaaagttg   4140
tatatttatt tggattatat ttacattctg tcctttgtaa atgtttggtg taacttgcac   4200
ttttttaaat gacccagttt gggtattagc aacttaagaa attccctcat caagtaattc   4260
tcaacttttt agtctttctc ctctcttcaa atcatgtgac tttttaaatg gaagtttttc   4320
attgattaaa atattttagc acctaaaagc tagccttaaa aacagctgta aaagaaaaac   4380
atcaggaaat tagatatgac tagcccagtt aattaaaaga cgggctcaaa ccttgtttta   4440
ttctttttca tcttggatga agattgaagg gaaaataact caagtgcata atatttattt   4500
tcaattttta atgagacttt atcctcatca caacattaat actgtacata gtatgccaaa   4560
atatccatta atttgtctag aatagtacaa gactttttaa agcaattgtc ctcacagaga   4620
ccacatgtaa tatactgaaa tatgttcatt tttaatggct ttgttaacat caaagaaatg   4680
ctgcctaaat ttgatttcag atgaggaagg agaaagtaaa gtgtgcatag taaggctgta   4740
ggtgaagagt tgtgagataa atagttcact cagttgtaca aagcacaact agaacttttt   4800
gttgggaggc ttacatacat cttgaatatt cttaatgtaa taatgttgac tattaagttg   4860
gctacacagt cactgtatgt actaggaact ggtttccttg acattctaga atcaatggct   4920
aggagaggca ttaatctttg aggggctgaa catatcatga agctgagtca gtatggaaaa   4980
ttttcaaata aacagggtgc tgaagttcca tctgtctcat ctgcttatga taagttctta   5040
ttgattagtg aatgtagctt aagcctttgt atgtgtcctc agggggcaga ccgactttaa   5100
gagggaccag ataacgtttg aatggaggga ttatatttca ggtgttttag cttgaaattt   5160
attttttaaa aaaagaaaaa tttaaaaaat atataaataa aatagaacaa agccggtgat   5220
gcaagttgat attataaaca ggcagtttta gcacagaaag aaaatactga cctgtctgca   5280
ttctggtacg gtgggtgcag gtcccagctg ggtatgacat gatacatttt taattattct   5340
caccagcaag taaaaggaaa atgaacaatc ttttggaatt gtctttgaaa aggatcaaag   5400
agtaggaaat tcacatttga cctaacatta cttgcctata gaagtatggc atttccaagc   5460
ttttgtctga ggagcatctc agagaagtga gagtaaatct gagttagctt aaaaattggt   5520
agggaggaag aaaatctctg caaataatga ttttatgttt gttggccaag tgaaatgatc   5580
tatcattgtg tttgggaggt tttattttct tatgttttta aaattggtaa atgctttata   5640
gatgtatttt tatccaagtg ccactccaat ttgtgtatgt aataaaatta tttatattaa   5700
aagtgggaaa taattgtcaa catttttttt gagtatagat ttattagggg tggcaaagaa   5760
gagtgctagt tagcagtttt ccatgtaaag ttgtccttga ctgatttgtc cacatgtcag   5820
ttgtaactcc cccactccct gcaaaaggaa ttatttctaa cccagatgta tcacttgaaa   5880
```

```
cttttagaa gcaaaataat cagggaagtt cctagaaagg tgtttggctt tttggttttt   5940
gagggttggg gtaaagaaga cttcccccac aactgtcagc acaaaacagg gtattgattt   6000
ttaactctga tgtttctatt ggagttgaat actaaataaa taactataat gagggaaata   6060
catttctaat aaaattccct acattctaga aacatccctg ttttaatttt tttatctaaa   6120
tctttttgtg ctttatgtgt aaagaaaaaa atgtactgag ttacaatgca ttttattaac   6180
actatgtaca taatagctgc tttgtgttca gaatagtagc agttgctttg tatattaaag   6240
tgatccttgt gaatttgtga aatattgtca taaagtgctt tttcttactg taatctttgt   6300
ggtatcaact gtcataatgc tctttttaca caaacattta tgtgcagtca cataaacatg   6360
cttttaaaaa ctctgtaagt ctcttttttg gggatgggat ctctatattt tgttgggttt   6420
tttttgctag tagtgtgaag ccatgtttta ttggacttaa agttacaata tattacaagc   6480
ttgtgttgga aggcagcaaa actaattcag acaacaacat gtcttcagtt actggatccc   6540
taattttcag gacaaaacct gtttttcaat aagattgaac agtgcctatt tgtggatttg   6600
gagatgttac tgtcaagatg actaatggag acatacgacc agctgtgtct gatgtcataa   6660
aacacgtgtt cactgaaagg acaataagac tatatacctt ctcaggtccc cttgcaattc   6720
taaaactctg tgatcatata aattggaagg aaaggggagg ggatatggtt aatctttgct   6780
taagctgtaa gaataaaaaa gttatctcct atactattaa cttctgaaat aagttctgag   6840
acgagacatc tgaaaataag cagctgcatt atttgtatgt ttcttcactg ccaagatgtg   6900
ttcaagcctg ctatacctgc cattgtattg gaaggcttaa tgaatttcat ttattttctg   6960
caacaacgat tacagaattt attgcacaaa atgagacatt ttgagagtga tattaattac   7020
atgagggaca ataggcatga actaggattg ttctaagcaa atcggaatcg ggtcaccctg   7080
ccacgttcag gtgcttggac cttcaggaaa agattgccca tcttgtcatt tgaccaggca   7140
ctgaagtgac aagaccatcc ttgagaagtc acatccaaag ataaaattct gatccatttc   7200
tagttttagt gtttcgccac tgaagactta acatatgtct tttacactca ggttgcaaaa   7260
cacaggccca agacaaactt aacttctccc ccaaatcttc cttccgctgg tttttccatc   7320
tcgtaagtgg tgccactatc catctgttaa attgtttagg ggaaacctag aaaagcacta   7380
ccttaatcag tgttatcctt cttcttaact gtgcgtccta atttctccac atctttctta   7440
agtgcagtga ccaaaccgga tgagaattct aacacgggcc tgacatcaaa tggaaaggaa   7500
ggataatgtc caggagttgg aatgttatcc ttgtttttaa ttaagatgca attcacataa   7560
attaactttt taagtgaaca attaagtggt agtacatcca caatggtgta caaccaccac   7620
ttctatctag ctccaaaaca ttctcatcac tccaaaagta aagtcccgtt actctccatt   7680
ttctcctccc accgcccttg tccctggcaa ccaccaatct gcttcctgtt tctttggatt   7740
tacatccggg tatttcatgt gagactcata cactgtgtat tacttctttc gtctagcttt   7800
aatgtgttgt tgaggttgat ccattgtaac atgttatcac tacttcattc ctttttatag   7860
ctaagtatac tttttatagt aagtatgcca ttgtagatat ataccacaag tttatcgatt   7920
catccagttg agttgtttct actgtttggc taatgttcat agtgctgtta tgaatgttcg   7980
tgtacaagta tttgagtccg tgttttcaat tatttggggt atatgcctgg gagtggagtt   8040
gctgggtcat gttgaaatcg cacatttaac tttttgagga actgtcaaac tttccctcag   8100
cagctgtacc gttttacctt ccaccattga tgtatgaggg ttccaatttc tccacacctt   8160
caccaacact tattttgcca ttttaaaaat tatagccatc ctcatgggtg tggtctctca   8220
```

-continued

```
ttgtggtttt gatttgcatt tccctgatta ctaatgatgt ggagcatctt ttgttgtctt   8280

tggccatctg cgtatcttct ttgaagaaat gtctgttgag gtcctttgtt cattgaaatt   8340

ttgttgttgg gttctgagtt ccttatatat tctgggtact aggcccttat aatattttcg   8400

cctataagtt tttgctttat aatgtcctca ttgttttcaa acttacttta tgtaatatgt   8460

acacttctaa aaaaaagaaa catggaaaag ggcaaactgt aagaagtttt ttgtgttatg   8520

tttttgtga cagtctgtgc atatatacac aaatataatg tatgttctct cctcctccct   8580

ctcccttttt ttacacaaaa ggtaggtaca aacagtggtt tataaactgc tgccattgta   8640

cagatacagt ttaaccagtc ctcttctggg gacatttggc tgtttgaaat tttttactgt   8700

tacagatata cagaggttgg taactaggtc tacacaagtt gtatctccag gatactgaga   8760

agtaaaagtt atttctgaat tatggttttc ttcatatttg gatattgttt cctaatgatt   8820

attaggtatc tgctaagcaa tttttattaa cttatgttga ttactatttt tatgtcaaac   8880

tttacagtct aggcattttt ttctggaatt aaaattagaa gtggcacaga caaaaaaaaa   8940

aaaa                                                                8944
```

COMPOSITIONS AND METHODS TO REDUCE BETA-AGONIST-MEDIATED TACHYPHYLAXIS

CROSS-REFERENCE TO RELATED APPLICATIONS

This application claims the benefit of and priority to U.S. Provisional Patent Application No. 62/624,165, filed on Jan. 31, 2018, entitled "Method to reduce Beta2-Adrenergic Receptor Downregulation," the contents of which is incorporated by reference herein in its entirety.

STATEMENT REGARDING FEDERALLY SPONSORED RESEARCH

This invention was made with Government support HL045967 and HL114471 awarded by the National Institutes of Health. The Government has certain rights in the invention.

SEQUENCE LISTING

This application contains a sequence listing filed in electronic form as an ASCII.txt file entitled 292105-1840_ST25.txt, created on Jan. 31, 2019. The content of the sequence listing is incorporated herein in its entirety.

BACKGROUND

Tachyphylaxis is a term used to describe a decrease, often a rapid decrease, in a subject's response to a drug after its administration. This can be a problem in subjects receiving β-agonists, thus decreasing the efficacy of these therapeutics in these subjects. As such, there exists a need to improve response to β-agonists in a subject.

SUMMARY

Described herein is a method of reducing β-agonist-mediated $\beta_2$-Adrenergic Receptor ($\beta_2$AR) down regulation in a subject in need thereof that can include the step of reducing the amount of let-7f miRNA in a cell of the subject in need thereof that expresses $\beta_2$AR and that has been exposed to a β-agonist, wherein the step of reducing the amount of let-7f miRNA comprises administering an amount of a let-7f miRNA inhibitor to the subject in need thereof. The let-7f miRNA inhibitor can be a direct let-7f miRNA inhibitor. The direct let-7f miRNA inhibitor can be a single stranded let-7f miRNA gene silencing oligonucleotide. The single stranded let-7f miRNA gene silencing oligonucleotide can include or be composed of an oligonucleotide having a sequence that is about 20-100% identical to 3 or more consecutive nucleotides of SEQ ID NO: 11. The single stranded let-7f miRNA gene silencing oligonucleotide can be a let-7f miRNA inhibitor polynucleotide. The let-7f miRNA inhibitor polynucleotide can include an oligonucleotide consists essentially of an oligonucleotide having a sequence that is about 20-100% identical to SEQ ID NO: 11. The let-7f miRNA inhibitor can include an indirect let-7f miRNA inhibitor. The indirect let-7f miRNA inhibitor can a CREB gene silencing oligonucleotide. The cell can be an airway cell. The subject in need thereof ca have an airway disease.

Also described herein is a method of treating an airway disease in a subject in need thereof that can include administering a beta-agonist to the subject in need thereof and administering an amount of an let-7f miRNA inhibitor effective to reduce the amount of let-7f miRNA in an airway cell that expresses $\beta_2$AR. The let-7f miRNA inhibitor can be a direct let-7f miRNA inhibitor. The direct let-7f miRNA inhibitor can be a single stranded let-7f miRNA gene silencing oligonucleotide. The single stranded let-7f miRNA gene silencing oligonucleotide comprises an oligonucleotide having a sequence that can be about 20-100% identical to 3 or more consecutive nucleotides of SEQ ID NO: 11. The single stranded let-7f miRNA gene silencing oligonucleotide can a let-7f miRNA inhibitor polynucleotide. The let-7f miRNA inhibitor polynucleotide can include an oligonucleotide is composed essentially of an oligonucleotide having a sequence that is about 20-100% identical to SEQ ID NO: 11. The let-7f miRNA inhibitor can be an indirect let-7f miRNA inhibitor. The indirect let-7f miRNA inhibitor can be a CREB gene silencing oligonucleotide. The beta-agonist can be selected from the group of: albuterol and pharmaceutically acceptable salts thereof, levalbuterol and pharmaceutically acceptable salts thereof, metaproterenol and salts thereof, salmeterol and pharmaceutically acceptable salts thereof, fomoterol and pharmaceutically acceptable salts thereof, afromoterol and pharmaceutically acceptable salts thereof, olodaterol and pharmaceutically acceptable salts thereof, vilanterol and pharmaceutically acceptable salts thereof, fenoterol and pharmaceutically acceptable salts thereof, epinephrine and pharmaceutically acceptable salts thereof, and combinations thereof. The airway cell can be a smooth muscle airway cell.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 1A and 1B) HASM cells from nonasthmatic or asthmatic lung donors were maintained in culture and treated with 100 mM ascorbic acid (control) or ascorbic acid with 30 mM ISO for 18 h at 37° C. The ascorbic acid is utilized to protect the agonist from oxidation. RNA and protein were derived from these cells and let-7f miRNA and $\beta_2$AR protein expression were determined as described in Materials and Methods (n=4 experiments each from a different donor). FIG. 1C) The 2 greatest and 2 least changes in $\beta_2$AR expression found in experiments from panels FIGS. 1A and 1B are indicated with the changes in let-7f levels. FIG. 1D) ADRB2 mRNA is not altered in HASM cells by 18 h ISO treatment (n=4 experiments from the D9 line). FIG. 1E) Knockdown of let-7f attenuates ISO promoted down-regulation of $\beta_2$AR in HASM cells (n=6 experiments) *$P<0.01$.

FIGS. 2A to 2B) Cultured HASM cells derived from asthmatic (FIG. 2A) and nonasthmatic (FIG. 2B) donor lungs were treated with 10 mM H89, 30 mM ISO, H89+ISO, 10 mM forskolin, or H89+forskolin for 18 h at 37° C. and let-7f miRNA expression was determined by quantitative RT-PCR. The expression of let-7f miRNA was increased by ISO and forskolin, which was blocked by the PKA inhibitor H89 (n=4 experiments, each from a different donor). FIGS. 2C and 2D) The same cells in panels A and B were treated with 100 mM cell-permeable cAMP analog dibutyryl cAMP (dB-cAMP) and let-7f miRNA expression was determined by quantitative RT-PCR. dB-cAMP increased let-7f expression, which was blocked by H89. (n=4 experiments, each from a different donor) *P<0.01, #P>0.05.

FIG. 3A) Transfection of CREB increases let-7f expression in HASM cells (n=3). FIG. 3B) Knockdown of CREB by siCREB ablates agonist promoted increases in let-7f (n=4). FIG. 3C) Knockdown of CREB impairs agonist-promoted down-regulation of $\beta_2$AR. A representative experiment (1 of 4) shows the silencing of CREB expression by siCREB, and the lack of ISO-promoted downregulation under these conditions. FIG. 3D) Knockdown of CREB attenuates ISO-promoted down-regulation of $\beta_2$AR (n=5). All experiments performed with ISO used a concentration of 30 mM with an exposure period of 18 h at 37° C. *P<0.01.

FIG. 4A) Potential CREB binding sites in the 5'-upstream region of pri-let-7f as identified by JASPER. FIG. 4B) Chromatin immunoprecipitation results using a CREB antibody and pri-let-7f primers for PCR. Sites 1, 2, and 3 were identified as CREB binding sites based on the presence of a PCR product. Results are representative of 4 experiments performed. IgG was utilized as a negative control in the immunoprecipitation step. The input refers to cell extracts prior to immunoprecipitation and the primers were validated by the presence of PCR products.

DETAILED DESCRIPTION

Figures 1A, 1B:
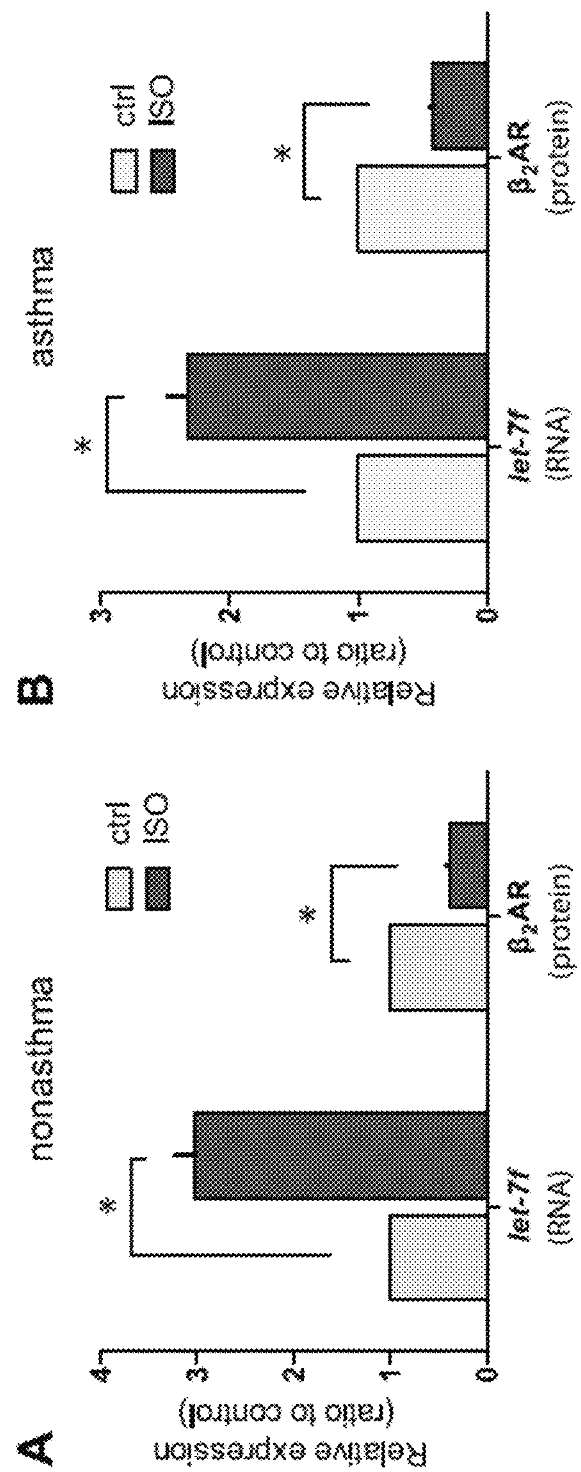
FIGS. 1A-1E shows graphs that can demonstrate agonist regulation of $\beta_2$AR and let-7f in HASM cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, biochemistry, physiology, cell biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intradermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "control" can refer to an alternative subject or sample used in an experiment for comparison purpose and included to minimize or distinguish the effect of variables other than an independent variable.

The term "copolymer" as used herein, generally refers to a single polymeric material that is comprised of two or more different monomers. The copolymer can be of any form, such as random, block, graft, etc. The copolymers can have any end-group, including capped or acid end groups.

As used herein with reference to the relationship between DNA, cDNA, cRNA, RNA, protein/peptides, and the like "corresponding to" or "encoding" (used interchangeably herein) refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct or molecule, which can include but is not limited to short hairpin RNA (shRNA), siRNA, and any vector containing sequences encoding the RNAi construct or molecule), siRNA (short interfering RNA), microRNA (miRNA), or ribozymes, aptamers, guide RNA (gRNA) or coding mRNA (messenger RNA).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "DNA molecule" can include nucleic acids/polynucleotides that are made of DNA.

As used herein, "dose," "unit dose," or "dosage" can refer to physically discrete units suitable for use in a subject, each unit containing a predetermined quantity of a let-7f miRNA inhibitor (direct or indirect) and/or a pharmaceutical formulation thereof calculated to produce the desired response or responses in association with its administration.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function. The "effective amount" can refer to the amount of a let-7f miRNA inhibitor or pharmaceutical formulation thereof described herein that can reduce β-agonist-mediated tachyphaylaxis in a subject in need thereof. The "effective amount" can refer to the amount of a let-7f miRNA inhibitor or pharmaceutical formulation thereof described herein that directly or indirectly reduce the amount of and/or activity of let-7f miRNA. The "effective amount" can refer to the amount of a let-7f miRNA inhibitor or pharmaceutical formulation thereof described herein that can directly or indirectly reduce the amount of $\beta_2$AR down-regulation that is caused by β-agonist administration and interaction with $\beta_2$AR. In some aspects, the effect is present in an airway cell of the subject in need thereof. In some aspects, the effect is present in a smooth muscle cell in the airway of the subject in need thereof. The "effective amount" can refer to the amount of a let-7f miRNA inhibitor or pharmaceutical formulation thereof described herein that can treat and/or prevent an airway disease or disorder or a symptom thereof in the subject in need thereof. In some embodiments the airway disease or disorder a reactive and/or obstructive airway disease. In some embodiments, the airway disease or disorder is asthma. In some embodiments, the airway disease can be a reversible or partially reversible obstructive airway disease, a reactive airway disease, or chronic obstructive pulmonary disease. In some embodiments, the airway disease is asthma, emphysema, bronchitis, chronic bronchitis, cystic fibrosis, reactive airways disease, and/or allergic bronchospasm.

As used herein, the term "encode" can refer to principle that DNA can be transcribed into RNA, which can then be translated into amino acid sequences that can form proteins.

As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "gene silencing oligonucleotide" refers to any oligonucleotide that can alone or with other gene silencing oligonucleotides utilize a cell's endogenous mechanisms, molecules, proteins, enzymes, and/or other cell machinery or exogenous molecule, agent, protein, enzyme, and/or polynucleotide to cause a global or specific reduction or elimination in gene expression, RNA level(s), RNA translation, RNA transcription, that can lead to a reduction or effective loss of a protein expression and/or function of a non-coding RNA as compared to wild-type or a suitable control. This is synonymous with the phrase "gene knockdown" Reduction in gene expression, RNA level(s), RNA translation, RNA transcription, and/or protein expression can range from about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, to 1% or less reduction. "Gene silencing oligonucleotides" include, but are not limited to, any antisense oligonucleotide, ribozyme, any oligonucleotide (single or double stranded) used to stimulate the RNA interference (RNAi) pathway in a cell (collectively RNAi oligonucleotides), small interfering RNA (siRNA), microRNA, short-hairpin RNA (shRNA), and gRNAs for CRISPR. The gene silencing oligonucleotide can be a miRNA inhibitor polynucleotide as defined elsewhere herein. Commercially available programs and tools are available to design the nucleotide sequence of gene silencing oligonucleotides for a desired gene, based on the gene sequence and other information available to one of ordinary skill in the art.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

As used herein, "identity," can refer to a relationship between two or more nucleotide or polypeptide sequences, as determined by comparing the sequences. In the art, "identity" can also refers to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

The term "lipophilic", as used herein, refers to compounds having an affinity for lipids.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

As used herein, "microRNA" can refer to a small non-coding RNA molecule containing about 21 to about 23 nucleotides found in organisms, which functions in transcriptional and post-transcriptional regulation of transcription and translation of RNA. "MicroRNA" can exist as part of a larger nucleic acid molecule such as a stem-loop structure that can be processed by a cell and yield a microRNA of about 21-23 nucleotides.

As used herein, "miRNA target" or "miRNA target sequence" can refer to the nucleic acid sequence, typically RNA, that a miRNA specifically binds to. The miRNA target can be or include a sequence that is complementary to the miRNA. As an example, microRNA 126 (miR-126) can specifically bind a miR-126 target. Binding of a miRNA to a miRNA target can result in transcription and/or translation inhibition of the nucleic acid sequence, such as through degradation of the nucleic acid sequence (typically mRNA or other type of RNA), that the miRNA target is part of). The miRNA target can be in a 3' and/or 5' untranslated region of a RNA molecule. A micro RNA does not have to have perfect complementarity to a miRNA target for specific binding or translation inhibition/to occur.

As used herein, "target miRNA" can refer to a microRNA that is the target molecule of a microRNA inhibitor polynucleotide.

As used herein, "microRNA inhibitor polynucleotide" refers to a polynucleotide of any length (includes oligonucleotides) that is single stranded and can specifically bind to a target microRNA and can prevent the target miRNA from binding to normal cellular binding sites (e.g. a target mRNA), can inhibit the miRNA association with the RISC or other RNAi molecules, and/or result in the degradation of the miRNA. The microRNA inhibitor polynucleotide can be 10%, 20%, 30%, 40%, 50%, 60%, 70%, 80%, 90% to 100% identical to the complementary or antisense strand of a target microRNA.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "operatively linked" in the context of recombinant DNA molecules, vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to effect expression or other characteristic of the coding sequence or transcribed non-coding sequence. This same term can be applied to the arrangement of coding sequences, non-coding and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "overexpressed" or "overexpression" refers to an increased expression level of an RNA and/or protein product encoded by a gene as compared to the level of expression of the RNA or protein product in a normal or control cell. The amount of increased expression as compared to a normal or control cell can be about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.3, 3.6, 3.9, 4.0, 4.4, 4.8, 5.0, 5.5, 6, 6.5, 7, 7.5, 8.0, 8.5, 9, 9.5, 10, 11, 12, 13, 14, 15, 16, 17, 18, 19, 20, 25, 30, 35, 40, 45, 50, 60, 70, 80, 90, 100 fold or more greater than the normal or control cell.

As used herein, the terms "optional" or "optionally" means that the subsequently described event or circumstance can or cannot occur, and that the description includes instances where said event or circumstance occurs and instances where it does not.

As used herein, "patient" can refer to an organism, host, or subject in need of treatment.

As used herein "peptide" can refer to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "polypeptides" or "proteins" refers to amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, "promoter" includes all sequences capable of driving transcription of a coding or a non-coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "specific binding" can refer to binding which occurs between such paired species such as enzyme/substrate, receptor/agonist, receptor/antagonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected. the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used herein, "substantially free" can mean an object species is present at non-detectable or trace levels so as not to interfere with the properties of a composition or process.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

A "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as β-agonist-mediated tachyphaylaxis, an airway disease or disorder, or a combination thereof. The effect can be therapeutic in terms of a partial or complete cure of a disease, condition, symptom or adverse effect attributed to the disease, disorder, or condition. The term "treatment" as used herein covers any treatment of β-agonist-mediated tachyphaylaxis, in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain. The disease or disorder being treated can include an airway disease or disorder or a symptom thereof, including but not limited to a reactive and/or obstructive airway disease. In some embodiments, the airway disease or disorder is asthma. In some embodiments, the airway disease can be a reversible or partially reversible obstructive airway disease, a reactive airway disease, or chronic obstructive pulmonary disease. In some embodiments, the airway disease is asthma, emphysema, bronchitis, chronic bronchitis, cystic fibrosis, reactive airways disease, and/or allergic bronchospasm.

As used herein, "underexpressed" or "underexpression" can refer to decreased expression level of an RNA (coding or non-coding RNA) or protein product encoded by a gene as compared to the level of expression of the RNA or protein product in a normal or control cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

DISCUSSION $\beta_2$ARs are expressed in airway smooth muscle cells to relax the muscle, leading to bronchodilation and increased airflow. Agonists to $\beta_2$ARs, often termed "β-agonists," are the primary therapy for acute reversal of airway narrowing in asthma and chronic obstructive pulmonary disease (COPD). These drugs are also utilized in chronic conditions to maintain airway patency and prevent exacerbations. Repetitive or prolonged β-agonist treatment has been shown to result in loss of bronchodilator sensitivity to acute β-agonists, a decrease in the bronchoprotective effect of β-agonists to inhaled bronchoconstrictors, tachyphylaxis (also called resistance to clinical effectiveness), and adverse effects including increased exacerbations and death. As such, there exists a need for decreasing the tachyphaylaxis in subjects in response to β-agonists, particularly in subjects having airway diseases or disorders.

With that said, described herein compositions capable of and methods of reducing β-agonist-mediated tachyphaylaxis in a subject. The method can include administering a compound to a subject that can directly or indirectly decrease the amount of let-7f miRNA in a cell. In some aspects, the cell is an airway cell. In some aspects, the cell is a smooth muscle cell. In some aspects, the cell is a smooth muscle airway cell. In some aspects, the compound capable of directly or indirectly decreasing the amount of let-7f miRNA can be a co-therapy to a β-agonist. In some aspects, the subject to which the compound capable of directly or indirectly decreasing the amount of let-7f miRNA can have an airway disease or disorder. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods to Reduce β-Agonist-Mediated Tachyphaylaxis

Tachyphaylaxis has been observed in subjects with airway diseases or disorders that are receiving β-agonists as treatment for these disease or disorders. As demonstrated herein, a significant portion of the tachyphaylaxis can be attributed to a negative feedback response mediated by binding of a β-agonist to the $\beta_2$AR on smooth muscle cells, particularly in the airway. As is demonstrated herein binding of a β-agonist to the $\beta_2$AR on smooth muscle cells can activate a cAMP-mediated signaling pathway within a smooth muscle cell and result in an increase in the expression and production of a mature let-7f miRNA. let-7f miRNA binds the 3' untranslated region (UTR) of ADRB2 mRNA transcripts causing transcript degradation via RISC-mediated transcript degradation. This results in a decrease in the amount of 2AR and subsequently a reduced responsiveness to β-agonist treatment.

Described herein are methods of reducing β-agonist-mediated tachyphaylaxis that can include directly or indirectly reducing the amount of a mature let-7f miRNA in a cell. Table 1 shows various let-7f miRNA and related sequences. The mature let-7f miRNA is produced from a precursor pri-miRNA transcribed from the genome. Processing by the enzyme Drosha produces a pre-miRNA, which is further cleaved by the enzyme Dicer to generate the mature and antisense miRNA products. The mature miRNA strand is incorporated into the RNA-induced silencing complex (RISC), which ultimately binds the complementary target mRNA (e.g. ARDB2 mRNA) through imperfect base pairing resulting in translation inhibition, mRNA destabilization, and/or mRNA degradation. This can reduce the expression of $\beta_2$AR and thus contribute to β-agonist-mediated tachyphaylaxis.

TABLE 1

Let-7f miRNA sequences

| Description | SEQ ID NO: | Database Identification | Sequence (5'→3') |
|---|---|---|---|
| Mature Let-7f miRNA 5p | 10 | miRBase Accession No.: MIMAT0000067 | UGAGGUAGUAGAUUGUAUAGUU |
| Anti-sense mature Let-7f miRNA 3p (*) | 11 | miRBase Accession No.: MIMAT004486 | CUAUACAAUCUAUUGCCUUCCC |
| pri-miRNA let-7f (human chromosome 9q22.2-31.1) | 12 | GenBank Accession No.: NR_029483 | TCAGAGTGAGGTAGTAGATTGTATA GTTGTGGGGTAGTGATTTTACCCTG TTCAGGAGATAACTATACAATCTAT TGCCTTCCCTGA |

TABLE 1-continued

| Let-7f miRNA sequences | | | |
|---|---|---|---|
| Description | SEQ ID NO: | Database Identification | Sequence (5'→3') |
| | | (miRBase Accession No.: M10000067) | |
| Sequence surrounding and including pri-miRNA let-7f human | 13 | GenBank Accession No.: AL158152.18 (AL158152v.18) | See Sequence Listing. |

In some embodiments, the method can include the step of directly reducing the amount of mature let-7f miRNA in a cell. By directly reducing the amount of mature let-7f miRNA (SEQ ID NO: 10) there is less mature let-7f miRNA that operate to reduce the amount of ARDB2 mRNA via the RNAi pathway and maintain and/or increase the amount of $\beta_2$AR available to interact with and respond to β-agonist. In this way, β-agonist-mediated tachyphaylaxis can be reduced and/or mitigated. let-7f miRNA can be directly reduced by administering to a subject an amount of a direct let-7f miRNA inhibitor. As used herein a direct let-7f miRNA inhibitor is a compound or molecule that can be capable of acting on a mature let-7f miRNA, pre-let-7f miRNA, and/or pri-let-7f miRNA that results in a reduction of the amount of the mature let-7f in the cell and/or inhibits either partially or completely the activity of the mature let-7f by decreasing the ability of the let-7f miRNA from interacting with RNAi machinery of the cell (e.g. RISC) and/or binding of its target RNA.

In some embodiments, the direct let-7f miRNA inhibitor can be a let-7f miRNA gene silencing oligonucleotide. In some embodiments, the let-7f miRNA gene silencing oligonucleotide is a single stranded gene silencing oligonucleotide. The let-7f miRNA gene silencing oligonucleotide can be composed essentially of or produce a single stranded oligonucleotide that can be composed essentially of an oligonucleotide having a sequence that is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to 100% identical to SEQ ID NO: 11. The let-7f miRNA gene silencing oligonucleotide can include or produce a single stranded oligonucleotide that can include an oligonucleotide having a sequence that is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to 100% identical to SEQ ID NO: 11. The let-7f miRNA gene silencing oligonucleotide can be a let-7f microRNA inhibitor polynucleotide. The let-7f miRNA gene silencing oligonucleotide can specifically bind a mature let-7f miRNA (e.g. SEQ ID NO: 10). In some embodiments, the let-7f microRNA inhibitor polynucleotide can have a sequence that is identical to a SEQ ID NO: 14. In some embodiments, the let-7f miRNA inhibitor polynucleotide can be produced by Dharmacon (Cat. No.: IH-30048-07).

Suitable let-7f microRNA gene silencing oligonucleotide (s) and let-7f miRNA inhibitor polynucleotides that can specifically bind the ORF, 5'UTR, and/or the 3'UTR can be designed using any suitable RNAi or miRNA inhibitor polynucleotide design tool or commercially available design service based on the precursor, mature, and anti-sense let-7f microRNA sequences provided and described herein. Such tools and services are available online and via companies such as, but not limited to, Sigma, Invitrogen, Eruofins, and Dharmacon. Further, one of ordinary skill in the art will appreciate how to synthesize the designed let-7f microRNA gene silencing oligonucleotide(s) and let-7f miRNA inhibitor polynucleotides using polynucleotide synthesis techniques generally known in the art. Further, one of ordinary skill in the art can perform appropriate in vitro experiments to determine which designed and synthesized gene silencing oligonucleotides can specifically bind and/of result in the translation inhibition and/or degradation of let-7f mature microRNA without undue experimentation.

In some embodiments, the let-7f miRNA gene silencing oligonucleotide can be expressed from an expression vector that can include a polynucleotide that can encode the let-7f miRNA gene silencing oligonucleotide. Once inside a cell the expression vector can generate short hairpin RNA molecules or other gene silencing oligonucleotides that can be processed by the cell and can lead to the inhibition or degradation of the mature let-7f miRNA as previously described.

As previously discussed, in addition to directly inhibiting the activity of or reducing the amount of let-7f miRNA, β-agonist-mediated tachyphaylaxis can also be reduced by indirectly inhibiting the activity of or reducing the amount let-7f miRNA. In this context, indirectly inhibiting the activity of or reducing the amount let-7f miRNA refers to inhibiting the activity of or reducing the amount of a molecule that is part of the upstream pathway in the production of let-7f miRNA in response to β-agonist binding or otherwise activating $\beta_2$AR such that let-7 miRNA production is reduced.

In some embodiments, let-7f miRNA can be indirectly inhibited/reduced by reducing the amount of and/or inhibiting the activity of CREB. As demonstrated elsewhere herein, CREB can be activated by PKA and can bind to one or more binding sites within the pri-et-7f miRNA gene promoter. The CREB binding site can be TGACGGCT (SEQ ID NO: 15), TGAAGTCT (SEQ ID NO:16), TGAAGTCA (SEQ ID NO: 17), or any combination thereof. Binding of CREB to one or more CREB binding sites, which can stimulate transcription of the pri-let-7f. By reducing the amount of CREB and/or the activity of CREB transcription of the pri-let-7 miRNA can be reduced, thereby indirectly inhibiting and/or reducing the amount of let-7f miRNA.

In some embodiments, let-7f miRNA can be indirectly reduced and/or inhibited by administering a CREB inhibitor. In some embodiments, the amount of or activity of CREB can be reduced by administering a CREB inhibitor. As used herein, a CREB inhibitor is a compound or molecule that can be capable of acting on CREB such that the amount or activity of CREB or the specific binding of CREB to a CREB binding site on the promoter region of the pri-let-7f gene is reduced. In some embodiments, the CREB inhibitor can reduce the phosphorylation of CREB.

In some embodiments, the CREB inhibitor can be a CREB gene silencing oligonucleotide. The CREB gene silencing oligonucleotide can be introduced to a cell and can specifically bind CREB mRNA, which can result in the inhibition of CREB mRNA translation, CREB mRNA destabilization, and/or CREB mRNA degradation via an RNAi pathway. In some embodiments, the CREB gene silencing oligonucleotide can be expressed from an expression vector that can include a polynucleotide that can encode the CREB gene silencing oligonucleotide(s). Once inside a cell the expression vector can generate short hairpin RNA molecules or other gene silencing oligonucleotides that can be processed by the cell and can lead to/result in the inhibition of mRNA translation and/or degradation of CREB mRNA as previously described. In some embodiments, the CREB gene silencing oligonucleotide can specifically bind to a polynucleotide that is about 50, 60, 70, 80, 90, 95, 99, to 100 percent identical to SEQ ID NO: 18 The open reading frame for SEQ ID NO: 18 is from nucleotide 252-1277 in SEQ ID NO: 18. The 5' untranslated region (UTR) of SEQ ID NO: 18 is from nucleotide 1 to 251 of SEQ ID NO: 18. The 3' UTR of SEQ ID NO: 18 is from nucleotide 1278 to 10221 of SEQ ID NO: 18. In some embodiments, the CREB gene silencing oligonucleotide can specifically bind to the open reading frame (SEQ ID NO: 19) of SEQ ID NO: 18. In some embodiments, the CREB gene silencing oligonucleotide can specifically bind to the 5' UTR (SEQ ID NO: 20) of SEQ ID NO: 18. In some embodiments, the CREB gene silencing oligonucleotide can specifically bind to the 3' UTR (SEQ ID NO: 21) of SEQ ID NO: 18. In some embodiments, the CREB gene silencing oligonucleotide can be siCREB (Dharmacon, Cat. No.: M-003619-01).

The CREB gene silencing oligonucleotide(s) that can specifically bind the ORF, 5'UTR, and/or the 3'UTR can be designed using any suitable RNAi design tool or commercially available design service based on the CREB ORF, 5'UTR, and 3'UTR sequences provided and described herein. Such tools and services are available online and via companies such as, but not limited to, Sigma, Invitrogen, Eruofins, and Dharmacon. Further, one of ordinary skill in the art will appreciate how to synthesize the designed CREB gene silencing oligonucleotides using polynucleotide synthesis techniques generally known in the art. Further, one of ordinary skill in the art can perform appropriate in vitro experiments to determine which designed and synthesized gene silencing oligonucleotides can specifically bind and/of result in the translation inhibition and/or degradation of CREB mRNA without undue experimentation.

In some embodiments, the CREB inhibitor can be a small molecule inhibitor that is not a gene silencing oligonucleotide. In some embodiments, the CREB inhibitor can be compound 666-15 (CAS ID No.: 1433286).

(666-15)

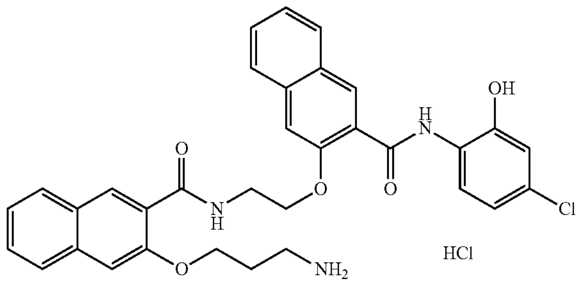

In some embodiments, a gene therapy approach can be used to modify one, two, or three of the CREB binding sites on the let-7f miRNA gene promoter, which can alter the ability of CREB to stimulate production of let-7f miRNA. In some embodiments, the gene therapy can be cell specific and alter the CREB binding sites in the let-7f miRNA gene in only smooth muscle or airway smooth muscle cells. Any suitable gene therapy approach can be used, including but not limited to viral vectors, CRISPR, Talens, or any other method known in the art.

In some embodiments, a direct let-7f miRNA inhibitor and/or an indirect let-7f miRNA inhibitor (collectively a let-7f miRNA inhibitor) as described above can be administered to a subject in need thereof. In some embodiments, the direct let-7f miRNA inhibitor and/or an indirect let-7f miRNA inhibitor can be a co-therapy to a β-agonist and thus can be co-administered with a β-agonist.

The let-7f miRNA inhibitor or pharmaceutical formulation thereof can be co-administered with a secondary agent (e.g. a co-therapy) by any convenient or appropriate route. The secondary agent can be a separate compound and/or formulation from the let-7f miRNA inhibitor or pharmaceutical formulation thereof. In some embodiments, the secondary agent is an auxiliary agent that is in addition to an auxiliary agent already present in the let-7f miRNA inhibitor or pharmaceutical formulation thereof. The secondary agent can be administered simultaneously with the let-7f miRNA inhibitor or pharmaceutical formulation thereof. The secondary agent can be administered sequentially with the let-7f miRNA inhibitor or pharmaceutical formulation thereof. In some embodiments, the secondary agent is a β-agonist. Suitable β-agonists include, but are not limited to, albuterol and pharmaceutically acceptable salts thereof, levalbuterol and pharmaceutically acceptable salts thereof, metaproterenol and salts thereof, salmeterol and pharmaceutically acceptable salts thereof, fomoterol and pharmaceutically acceptable salts thereof, afromoterol and pharmaceutically acceptable salts thereof, olodaterol and pharmaceutically acceptable salts thereof, vilanterol and pharmaceutically acceptable salts thereof, fenoterol and pharmaceutically acceptable salts thereof, epinephrine and pharmaceutically acceptable salts thereof, and combinations thereof.

In embodiments where the let-7f miRNA inhibitor or pharmaceutical formulation thereof are simultaneously co-administered with a β-agonist, the let-7f miRNA inhibitor or pharmaceutical formulation thereof can be administered to the subject at substantially the same time as the secondary agent. As used in this context "substantially the same time" refers to administration of the let-7f miRNA inhibitor or pharmaceutical formulation thereof and a secondary agent where the period of time between administration of the let-7f miRNA inhibitor or pharmaceutical formulation thereof and the secondary agent is between 0 and 10 minutes.

In embodiments where the let-7f miRNA inhibitor or pharmaceutical formulation thereof is/are sequentially co-administered with a β-agonist, the let-7f miRNA inhibitor (collectively referring to direct or indirect let-7f miRNA inhibitors as described elsewhere herein) or pharmaceutical formulation thereof can be administered first, and followed by administration of the β-agonist after a period of time. In other embodiments where the let-7f miRNA inhibitor or pharmaceutical formulation thereof is/are sequentially co-administered with a β-agonist, the β-agonist can be administered first, and followed by administration of the let-7f miRNA inhibitor or pharmaceutical formulation thereof after a period of time. The period of time between administration of the let-7f miRNA inhibitor or pharmaceutical formulation thereof and the β-agonist can range from 10 minutes to about 96 hours. In some embodiments, the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

In some embodiments, the let-7f miRNA inhibitor or pharmaceutical formulation thereof and/or β-agonist can be administered to a subject in need thereof one or more times per day, week, month, or year. In some embodiments, the amount administered can be the therapeutically effective amount of the let-7f miRNA inhibitor or pharmaceutical formulation thereof and/or β-agonist. For example, the let-7f miRNA inhibitor or pharmaceutical formulation thereof and/or β-agonist can be administered in a daily dose. This amount may be given in a single dose per day. In other embodiments, the daily dose may be administered over multiple doses per day, in which each contains a fraction of the total daily dose to be administered (sub-doses). In some embodiments, the amount of doses delivered per day is 2, 3, 4, 5, or 6. In further embodiments, the let-7f miRNA inhibitor or pharmaceutical formulation thereof and/or β-agonist can be administered one or more times per week, such as 1, 2, 3, 4, 5, or 6 times per week. In other embodiments, the let-7f miRNA inhibitor or pharmaceutical formulation thereof and/or β-agonist can be administered one or more times per month, such as 1 to 5 times per month. In still further embodiments, the let-7f miRNA inhibitor or pharmaceutical formulation thereof and/or β-agonist can be administered one or more times per year, such as 1 to 11 times per year.

The amounts, including effective amounts, of the let-7f miRNA inhibitor or pharmaceutical formulation thereof that can be administered are described elsewhere herein. The amount of the β-agonist will vary depending on the β-agonist, and can include the recommended amount as approved by the appropriate governing body such as the US Federal Drug Administration (often included in the "patient information insert". In some embodiments, the dosage of β-agonist can be more, or less, than the recommended dosage due to the level of severity of the disease. In some embodiments the amount can be consistent with what a clinician determines to be a therapeutically effective amount on an as patient basis. In some embodiments, the effective amount of the β-agonist ranges from 0.001 micrograms to about 1 milligram. In other embodiments, the amount of the β-agonist can range from about 0.01 IU to about 1000 IU. In further embodiments, the amount of the β-agonist can range from 0.001 mL to about 5 mL. In yet other embodiments, the amount of the β-agonist can range from about 0.01% w/w to about 50% w/w of the total pharmaceutical formulation. In additional embodiments, the amount of the β-agonist can range from about 0.01% v/v to about 50% v/v of the total pharmaceutical formulation. In still other embodiments, the amount of the β-agonist can range from about 0.01% w/v to about 50% w/v of the total β-agonist composition or pharmaceutical formulation.

Where the β-agonist is albuterol or a pharmaceutically acceptable salt thereof, the effective amount can range from 90 micrograms to about 180 micrograms delivered via an inhaler as a dry powder or a liquid mist at 1-2 puffs at a time. Where the β-agonist is levalbuterol or a pharmaceutically acceptable salt thereof, the effective amount ca be 0.31 mg, to 1.25 mg or 0.63 mg to 1.25 mg, which can be provided in a liquid and administered via nebulization 1-3 times per day. Where the β-agonist is metaproterenol or a pharmaceutically acceptable salt thereof, the effective amount can range from 0.4 to 2.6 mg/kg per day or 1.6 to 2.6 mg/kg per day administered orally, divided into 1, 2, 3, or 4 doses daily. In some embodiments, the therapeutically effective amount of metaproterenol can range from 10-20 or 15 to 20 mg administered orally and divided into 1-4 does per day. In some embodiments, the therapeutically effective amount of metaproterenol can be 10-15 mg delivered via inhalation at 2-3 inhalations (or puffs) 1-4 times per day. Where the β-agonist is salmeterol or a pharmaceutically acceptable salt thereof, the effective amount can range from 50 micrograms provided via inhalation up to twice daily. Where the β-agonist is fomoterol or a pharmaceutically acceptable salt thereof, the therapeutically effective amount can range from 6 micrograms to 12 micrograms provided via inhalation 1-8 times per day for a maximum dose per day of 48 micrograms. Where the β-agonist is olodaterol or a pharmaceutically acceptable salt thereof, the therapeutically effective amount can be 5 mcg/day or less as inhaled at 1-2 puffs or actuations 1-2 times per day. Where the β-agonist is vilanterol or pharmaceutically acceptable salts thereof, the dose can be 25 mcg fenoterol and provided as a powder or contained in a liquid that can be inhaled or in 1-2 actuations 1-2 times per day. Other dosing for these β-agonists can be found as previously described. Where the β-agonist is epinephrine or a pharmaceutically acceptable salt thereof, the therapeutically effective dose can range from about 0.001 mg to about 5 mg or more as delivered intravenously, intramuscularly, subcutaneously, or any other suitable route.

In some embodiments, the let-7f miRNA inhibitor or pharmaceutical formulation thereof and/or β-agonist can be administered to a patient via an injection. Suitable methods of injection include, but are not limited to, intravenous, intraperitoneal, subcutaneous, intramuscular, or intradermal injection. Other suitable methods of administering the let-7f miRNA inhibitor or pharmaceutical formulation thereof and/or secondary agent (e.g. a β-agonist) can include, but are not limited to oral, intravenous, subcutaneous, transdermal, nasal, or inhaled delivery. Delivery can be local or systemic. In some embodiments, delivery is local to the airways of a subject in need thereof. In some embodiments, delivery is local to the smooth muscle of the airways of the subject. Such local delivery can be achieved, via nebulization or aerosol inhalation. Suitable dosage forms are discussed elsewhere herein.

Pharmaceutical Formulations.

The direct and indirect let-7f miRNA inhibitors (collectively let-7f miRNA inhibitors) described herein can be contained in a pharmaceutical formulation that can be administered to a subject in need thereof. The subject in need thereof can have an airway disease or disorder. In some aspects the subject is undergoing β-agonist therapy for the airway disease or disorder. In some aspects the airway disease can be a reversible or partially reversible obstructive airway disease, a reactive airway disease, or chronic obstructive pulmonary disease. In some embodiments, the airway disease is asthma, emphysema, bronchitis, chronic bronchitis, cystic fibrosis, reactive airways disease, and/or allergic bronchospasm.

Pharmaceutically Acceptable Carriers and Auxiliary Ingredients and Agents

The pharmaceutical formulations described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of the let-7f miRNA inhibitor or pharmaceutical formulation thereof and/or a β-agonist described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Effective Amounts of the let-7f miRNA Inhibitors

As discussed elsewhere herein, an advantage of the let-7f miRNA inhibitor can be that it can mitigate β-agonist-mediated tachyphaylaxis. The pharmaceutical formulations described herein can contain a therapeutically effective amount and/or a minimum effective amount of a let-7f miRNA inhibitor. The therapeutically effective amount of the let-7f miRNA inhibitor can range from about 1 pg to about 10 g, and can vary depending on the specific let-7f miRNA inhibitor. In some embodiments, the therapeutically effective amount of the let-7f miRNA inhibitor can range from about 10 nL to about 10 mL, and can vary depending on the specific let-7f miRNA inhibitor. In some embodiments, the therapeutically effective amount of the let-7f miRNA inhibitor can range from about 10 nL to about 1 μL, and can vary depending on the specific let-7f miRNA inhibitor. In some embodiments, the therapeutically effective amount of the let-7f miRNA inhibitor can range from about 1 μg/kg to about 10 mg/kg, and can vary depending on the specific let-7f miRNA inhibitor. In further embodiments, the therapeutically effective amount of the let-7f miRNA inhibitor can range from 1 ng/g bodyweight to about 0.1 mg/g bodyweight, and can vary depending on the specific let-7f miRNA inhibitor.

In some embodiments, the pharmaceutical formulation can include an effective amount of a β-agonist. Effective amounts of a β-agonist are discussed elsewhere herein. In some embodiments, the let-7f miRNA inhibitor and/or β-agonist containing pharmaceutical formulation can include or be co-administered with an auxiliary agent. In embodiments where there is an auxiliary active agent, contained in the pharmaceutical formulation in addition to the let-7f miRNA inhibitor and/or β-agonist, the therapeutically effective amount of the auxiliary active agent will vary depending on the auxiliary active agent. In some embodiments, the effective amount of the auxiliary active agent can range from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, subcutaneous, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the let-7f miRNA inhibitor, β-agonist, and/or auxiliary agent. The oral dosage form can be administered to a subject in need thereof.

Where appropriate, the dosage forms described herein can be microencapsulated. The dosage form can also be prepared to prolong or sustain the release of any ingredient. In some embodiments, the let-7f miRNA inhibitor can be the ingredient whose release is delayed. In other embodiments, the release of an optionally included β-agonist and/or auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, let-7f miRNA inhibitor, β-agonist and/or auxiliary agent can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the let-7f miRNA inhibitor, β-agonist, and/or auxiliary agent (e.g. a β-agonist) can be in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the let-7f miRNA inhibitor, β-agonist, and/or auxiliary agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the let-7f miRNA inhibitor, β-agonist, and/or auxiliary agent, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a let-7f miRNA inhibitor, β-agonist, and/or auxiliary agent. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, 8, 10, 12, 14, 16, 18, 20 or 24 times daily, in which 1, 2, or 3 doses are delivered each time.

For some dosage forms suitable and/or adapted for inhaled administration, the pharmaceutical formulation is a dry powder inhalable formulation. In addition to the let-7f miRNA inhibitor, β-agonist, and/or auxiliary agent such a dosage form can contain a powder base such as lactose, glucose, trehalose, manitol, and/or starch. In some of these embodiments, the let-7f miRNA inhibitor, β-agonist, and/or auxiliary agent can be in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the let-7f miRNA inhibitor and/or auxiliary agent described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the let-7f miRNA inhibitor, β-agonist, and/or auxiliary agent per unit dose. In some embodiments, the predetermined amount of the let-7f miRNA inhibitor is an amount effective to treat or prevent an airway disease or disorder or a symptom thereof. In some embodiments, the predetermined amount of the let-7f miRNA inhibitor is an amount effective to reduce β-agonist-mediated tachyphaylaxis in a subject in need thereof. The subject in need thereof can have an airway disease or disorder. Exemplary airway diseases or disorders are discussed elsewhere herein. In other embodiments, the predetermined amount of the let-7f miRNA inhibitor, β-agonist, and/or auxiliary agent can be an appropriate fraction of the therapeutically effective amount of the active ingredient (e.g. let-7f miRNA inhibitor, β-agonist, and/or auxiliary agent). Such unit doses may therefore be administered once or more than once a day. Such pharmaceutical formulations may be prepared by any of the methods well known in the art.

Kits Containing the Let-7f miRNA Inhibitor or Pharmaceutical Formulations Thereof The let-7f miRNA inhibitor or pharmaceutical formulation thereof and/or secondary agent(s) (e.g. a β-agonist), and/or auxiliary agent described herein can be presented as a combination kit. As used herein, the terms "combination kit" or "kit of parts" refers to the let-7f miRNA inhibitor or pharmaceutical formulation thereof and/or secondary agent (e.g. a β-agonist), and/or auxiliary agent and any additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agent(s)) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof described herein, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the let-7f miRNA inhibitor or pharmaceutical formulation thereof and/or secondary agent(s) (e.g. a β-agonist), and/or auxiliary agent described herein, safety information regarding the content of let-7f miRNA inhibitor or pharmaceutical formulation thereof and/or secondary agent(s) (e.g. a β-agonist) described herein and/or other auxiliary contained therein, information regarding the dosages, indications for use, and/or recommended treatment regimen(s) for let-7f miRNA inhibitor or pharmaceutical formulation thereof and/or secondary agent(s) (e.g. a β-agonist) described herein and/or other auxiliary contained therein. In some embodiments, the instructions can provide directions for administering let-7f miRNA inhibitor or pharmaceutical formulation thereof and/or secondary agent(s) (e.g. a β-agonist) described herein and/or other auxiliary to a subject having an airway disease or disorder. In some aspects the subject is undergoing β-agonist therapy for the airway disease or disorder. In some aspects the airway disease can be a reversible airway disease, a reactive airway disease, or chronic obstructive pulmonary disease. In some embodiments, the airway disease is asthma. In some embodiments, the airway disease can be a reversible or partially reversible obstructive airway disease, a reactive airway disease, or chronic obstructive pulmonary disease. In some embodiments, the airway disease is asthma, emphysema, bronchitis, chronic bronchitis, cystic fibrosis, reactive airways disease, and/or allergic bronchospasm.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Introduction

Like many other 7 transmembrane-spanning GPCRs, the β2-adrenergic receptor (β2AR) undergoes agonist-promoted desensitization (1, 2). Desensitization is defined as the loss of receptor function during continuous agonist activation, and represents a homeostatic mechanism by which cells and organs regulate receptor function within the context of multiple signals. Receptor desensitization is considered integral to normal physiologic conditions, and can be adaptive or maladaptive in disease states (3). GPCR desensitization is also the basis for reduced effectiveness of therapeutic agonists administered on a chronic basis, clinically recognized as tolerance or tachyphylaxis. Early events in agonist-promoted desensitization of $\beta_2$ARs include phosphorylation of the agonist-occupied receptor by GPCR kinases (GRKs). This establishes a substrate for receptor binding of β-arrestins, which partially disrupt the coupling of the receptor to the G protein (4). For $\beta_2$ARs and many other GPCRs, b-arrestins also mediate receptor internalization from the cell surface to the interior of the cell. At this juncture, the internalized receptor either proceeds toward a degradation pathway, or can be recycled to the cell surface if an agonist is no longer present (5). Owing to their adapter functions, β-arrestins also initiate other signaling events, as reviewed in Lefkowitz et al. (6) These early processes are followed by a gradual decrease in $\beta_2$AR expression (regardless of cellular localization) when agonist exposure is on the order of several hours, a process termed down-regulation. This decrease in expression can be substantial, resulting in a $90% loss of cell surface expression. For many cell types, down-regulation represents the main mechanism of desensitized cellular responses during long-term agonist exposure.

$\beta_2$ARs are expressed in airway smooth muscle cells to relax the muscle, leading to bronchodilation and increased airflow. Agonists to $\beta_2$ARs, often termed "β-agonists," are the primary therapy for acute reversal of airway narrowing in asthma and chronic obstructive pulmonary disease (COPD). These drugs are also utilized in chronic conditions to maintain airway patency and prevent exacerbations. Repetitive or prolonged β-agonist treatment has been shown to result in loss of bronchodilator sensitivity to acute β-agonists (7, 8), a decrease in the bronchoprotective effect of β-agonists to inhaled bronchoconstrictors (9, 10), tachyphylaxis (8, 11-14), and adverse effects including increased exacerbations and death (15-18). Thus, there continues to be interest in the molecular basis of long-term agonist-promoted downregulation of $\beta_2$ARs in human airway smooth muscle (HASM) cells. As detailed in the Discussion section of this Example, there is ample evidence suggesting additional mechanisms in play during down-regulation other than degradation of R-arrestin-mediated internalized receptors. This evidence can suggest that down-regulation is not simply the result of a continuum from the short-term events to this long-term outcome. It has been recently shown that expression of the gene encoding the $\beta_2$AR, adrenoreceptor $\beta_2$ (ADRB2), is significantly regulated by the small, noncoding microRNA (miRNA) let-7f, which binds to ADRB2 3' untranslated regions and represses translation (19). In model transfected cell systems and in cells that endogenously express $\beta_2$ARs, the expression levels of let-7f are inversely proportional to the expression of $\beta_2$ARs, consistent with the role of miRNAs in repressing translation.

In this Example, the potential for chronic β-agonists to alter let-7f expression in HASM cells was examined and observed, and studies were carried out to determine the mechanism by which this occurs. This novel let-7f-mediated mechanism appears to be responsible for about 50% of the total $\beta_2$AR down-regulation found with chronic b-agonist exposure, and accounts for the majority of the previously unexplained down-regulation observed in HASM cells.

Materials and Methods

Cell culture.

The HASM cells, derived from donor lungs of asthmatic and non-asthmatic patients, have been previously described (20, 21). Cells between passages 5 and 7 were used, which were cultured in DMEM supplemented with 10% fetal bovine serum in an environment composed of 95% air and 5% $CO_2$ at 37° C. The immortalized HASM cell line denoted D9 hTERT was developed as described (22), and was grown in the same manner. For the treatment with isoproterenol (ISO), cells between 80 and 90% confluency were placed in fresh medium with either 30 μM ISO, 100 μM isobutylmethylxanthine (to inhibit phosphodiesterase), and 100 μM ascorbic acid (to inhibit oxidation of ISO), or ascorbic acid alone, and incubated for 18 h. Cells were then washed 3 times with room temperature PBS and processed for protein or for RNA. In a similar manner, cells were treated with 100 M dibutyryl-cAMP or 10 mM forskolin. In some experiments, pretreatment with 10 μM N-(2-[p-bromocinnamylamino]ethyl)-5-isoquinoline-sulfonamide (H89) occurred for 1 h prior to the aforementioned treatments.

Transfections

HASM cells in 6-well plates were transfected using Lipofectamine 2000 (Thermo Fisher Scientific, Waltham, Mass., USA) as described in detail elsewhere (22, 23). Cells were in a final volume of 1.0 ml and the indicated constructs along with 10 ml of Lipofectamine 2000 were added to initiate the transfection. The constructs and final concentrations were: cAMP receptor element-binding protein [CREB (in pcDNA3, 4 μg/ml)], siCREB (40 nM of siGenome SmartPool; Dharmacon, Lafayette, Colo., USA), and to inhibit let-7f, a competitive inhibitor (Dharmacon) that binds to let-7f (24, 25) at a final concentration of 40 nM (24, 25). The cells were studied 48 h after transfection. If cells were also treated with a drug, the agent was added at the indicated concentration at the 48-h point for an additional 18 h.

Western Blots and Quantitative RT-PCR.

SDS-PAGE was performed over 7 h using 12% polyacrylamide gels on whole-cell lysates solubilized in RIPA buffer (about 10 μg), which were then transferred to PVDF membranes over 16 h, as previously described (22, 23). The titer (v/v) and antibodies were: SC-569 ($\beta_2$AR, 1:500; Santa Cruz Biotechnology, Dallas, Tex., USA), 9197 (CREB, 1:1000; Cell Signaling Technology, Danvers, Mass., USA), A1978 (actin, 1:2000; Sigma-Aldrich, St. Louis, Mo., USA). Secondary antibody for chemoluminescence (Thermo Fisher Scientific) was at a titer of 1:10,000. ChemiDoc (Bio-Rad, Hercules, Calif., USA) was used to detect bands, which were quantitated using ImageJ (National Institutes of Health, Bethesda, Md., USA). RT-PCR was performed using a LightCycler 96 system (Roche, Basel, Switzerland) and TaqMan polymerase (Applied Biosystems, Foster City, Calif., USA) as previously described (26, 27). The RT reactions utilized Oligo d(T)16 for ADRB2 and glyceraldehyde-3 phosphate dehydrogenase (control), and the primers included with the TaqMan MicroRNA assay (Applied Biosystems) for the reaction with let-7f and U6 snRNA (control). The following assay IDs (Thermo Fisher Scientific) were used for PCR:ADRB2 (Hs00240532_sl), glyceraldehyde-3 phosphate dehydrogenase (Hs02786624_gl), let-7f (000382), and U6 snRNA (001973). Quantitation of transcripts was made by the 22DCt method (28, 29).

Chromatin Immunoprecipitation.

Adhered HASM cells were treated with 1% formaldehyde in media for 10 min at 25° C., followed by the addition of 125 mM glycine to quench the fixation. After washing 3 times with PBS, cells were lysed and sheared by sonication. After brief centrifugation, pellets were diluted in 0.01% SDS, 1.1% Triton X-100, 1.2 mM EDTA, 167 mM NaCl, 16.7 mM Tris, (pH 8.0) buffer and precleared by incubation with sheared salmon sperm DNA and A/G agarose beads for 1 h at 4° C. and then centrifuged at 2000 rpm for 4 min at 4° C. An aliquot of the supernatant was collected to represent the input. The remaining supernatants were subjected to immunoprecipitation (12 h at 4° C.) using A/G agarose beads and an anti-CREB antibody (1:100; Cell Signaling Technology) or normal rabbit IgG as a control (Thermo Fisher Scientific). Subsequently, the agarose beads were sequentially washed with a low salt, high salt, and LiCl-based buffers as described in Qiu et al. (30), and then eluted with a 1% SDS, 0.1 M $NaHCO_2$ buffer. Crosslinking, RNase A treatment, and DNA purification were performed as previously described (30). PCR to identify predicted CREB binding sites in pri-let-7f was carried out using GoTaq (Promega, Madison, Wis., USA) and the following primers: 5'-TGTGTGTTTTGCACACCAGTT-3' (forward) (SEQ ID NO: 1) and 5'-AGACAATTCAACTGGGAATCG-3' (reverse) (site 1) (SEQ ID NO: 2), 5'-GCTACCTCCTAAATATGAAGTCTGT-3' (forward) (SEQ ID NO: 3) and 5'-TGAAGGCAGAGTCCAAAATCT 3' (reverse) (site 2) (SEQ ID NO: 4), 5'-TCGTTGTATGTTAGTGCATTTGGA-3' (forward) (SEQ ID NO: 5) and 5'-CAGAAAAACATGACAGCCTCTAA-3' (reverse) (site 3) (SEQ ID NO: 6), and 5'-ACACCCACCACTGGGAGATAA-3' (forward) (SEQ ID NO: 7) and 5'-ACTGACTTTCTATCAGACCGCC-3' (reverse) (site 4) (SEQ ID NO: 8).

Radioligand binding. Confluent cells in 10 cm dishes were washed 3 times with cold PBS followed by disruption with a cell scraper in buffer consisting of 5 mM Tris and 2 mM EDTA at 4° C. (pH 7.4). Crude membranes were collected by centrifugation at 30,000 g for 15 min at 4° C., and resuspended in assay buffer consisting of 75 mM Tris, 12 mM $MgCl_2$, and 5 mM EDTA at 25° C. (pH 7.4). Saturation radioligand binding was performed using about 20 μg membranes and the 2AR radioligand [125]-cyanopindolol in the absence (total binding) and presence (nonspecific binding) of 10 mM alprenolol as described in Mialet Perez et al. (31). After incubation for 1.5 h at 25° C., bound radioligands were separated from free radioligands by rapid dilution and vacuum filtration with buffer containing 15 ml of 5 mM Tris and 2 mM EDTA at 25° C. (pH 7.4) over Whatman GF/C filters (GE Healthcare Bio-Sciences, Piscataway, N.J., USA) using a Brandel cell harvester (Brandel, Gaithersberg, Md., USA). Specific binding was divided by the added cell membrane protein and $\beta_2$AR expression stated as femtomoles per milligram.

Informatics and Statistical Analysis.

Potential CREB binding sites in pri-miRNA let-7f (GenBank NR_029483; National Center for Biotechnology Information, Bethesda, Md., USA: (ncbi.nlm.nih.gov/genbank/) were determined using the JASPAR database (jaspar.genereg.net) (32). The sequence surrounding pri-miRNA let-7f was taken from human chromosome 9q22.2-31.1 sequence deposited as GenBank AL158152 v.18. Queries were made for CREB binding sites 1750 bp upstream of the initiator ATG. The consensus CREB binding sequence was considered TGACGTCA (SEQ ID NO: 9) and the profile score threshold set at 80%. Statistical comparisons of biochemical studies were made using GraphPad Prism 6.0 (La Jolla, Calif., USA) using 2-tailed, paired Student's t tests with a value of P<0.05 considered significant. Data are shown as means 6SE.

Results.

Figures 1C, 1D:
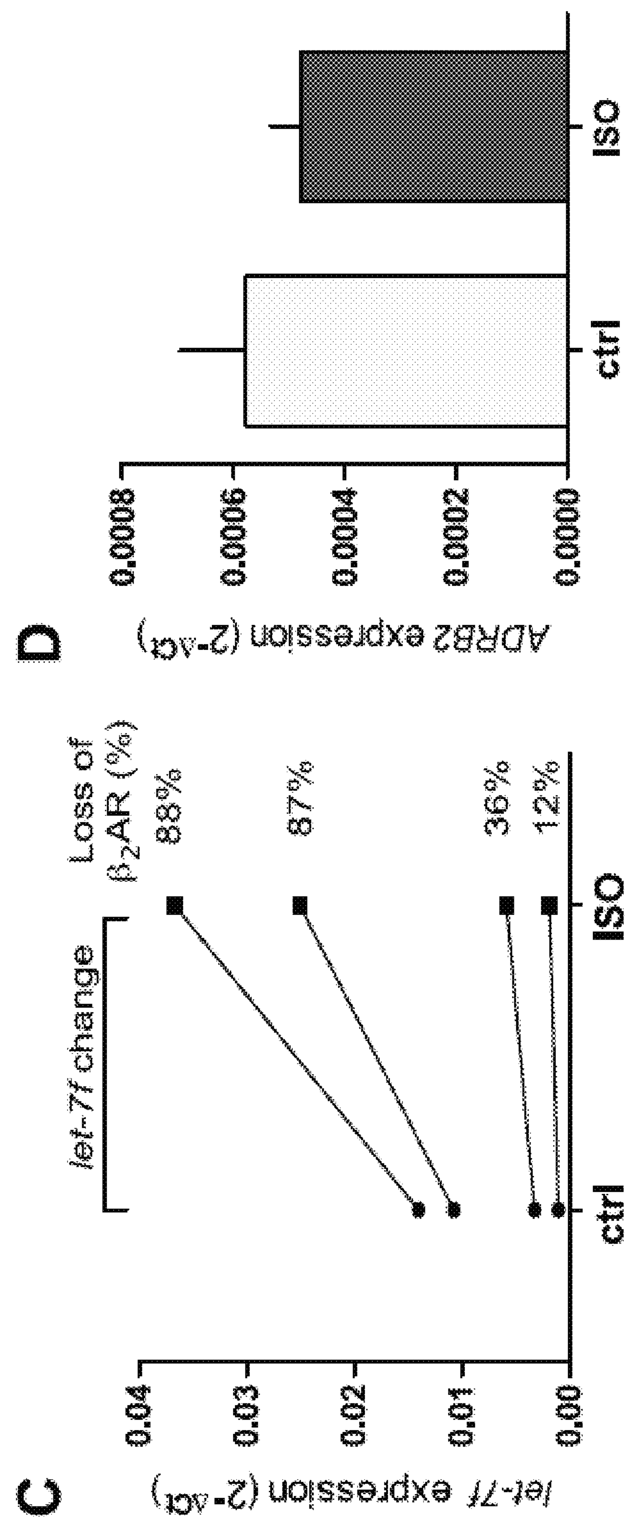
Figure 1E:
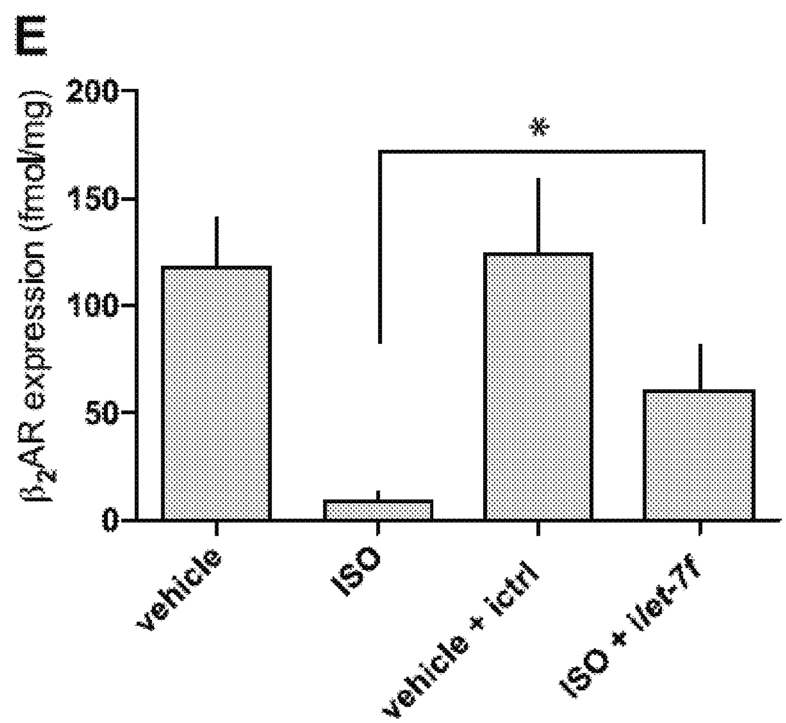

It has previously been shown that HASM cells from asthmatic lungs maintained in culture retain signaling characteristics consistent with a bronchospastic phenotype (33). Thus, this Example can demonstrate the relevance of let-7f to $\beta_2$AR expression and regulation not only in cells of physiologic relevance, and also to confirm that results found in HASM cells obtained from normal lungs were recapitulated in those from asthmatic lungs. Initial efforts were focused on whether let-7f in HASM cells is regulated by long-term β-agonist exposure, and the consequences of such regulation on $\beta_2$AR expression. As shown in FIGS. 1A-1B, 18 h of exposure to the β-agonist ISO caused about a 3-fold increase in let-7f miRNA expression in both asthmatic and non-asthmatic HASM ells. This was also accompanied by a decrease in $\beta_2$AR expression in both groups of cells. In addition, cells that displayed the most $\beta_2$AR down-regulation had the greatest change in let-7f, while those with the least change in $\beta_2$AR expression had the smallest change in let-7f after ISO exposure, consistent with a potential causal relationship (FIG. 1C). Immortalized D9 HASM cells were utilized in certain studies because these are more readily transfected compared with the primary lines. These cells showed the same $\beta_2$AR and let-7f responses to ISO as the primary HASM cells (data not shown). In D9 HASM cells, ADRB2 mRNA was not found to be changed due to ISO exposure (FIG. 1D). Furthermore, inhibition of let-7f markedly attenuated (but did not fully abrogate) $\beta_2$AR downregulation by ISO, further indicating a causal relationship between the change in let-7f and b $\beta_2$AR down-regulation by agonist exposure (FIG. 1E).

Figures 2A, 2B:
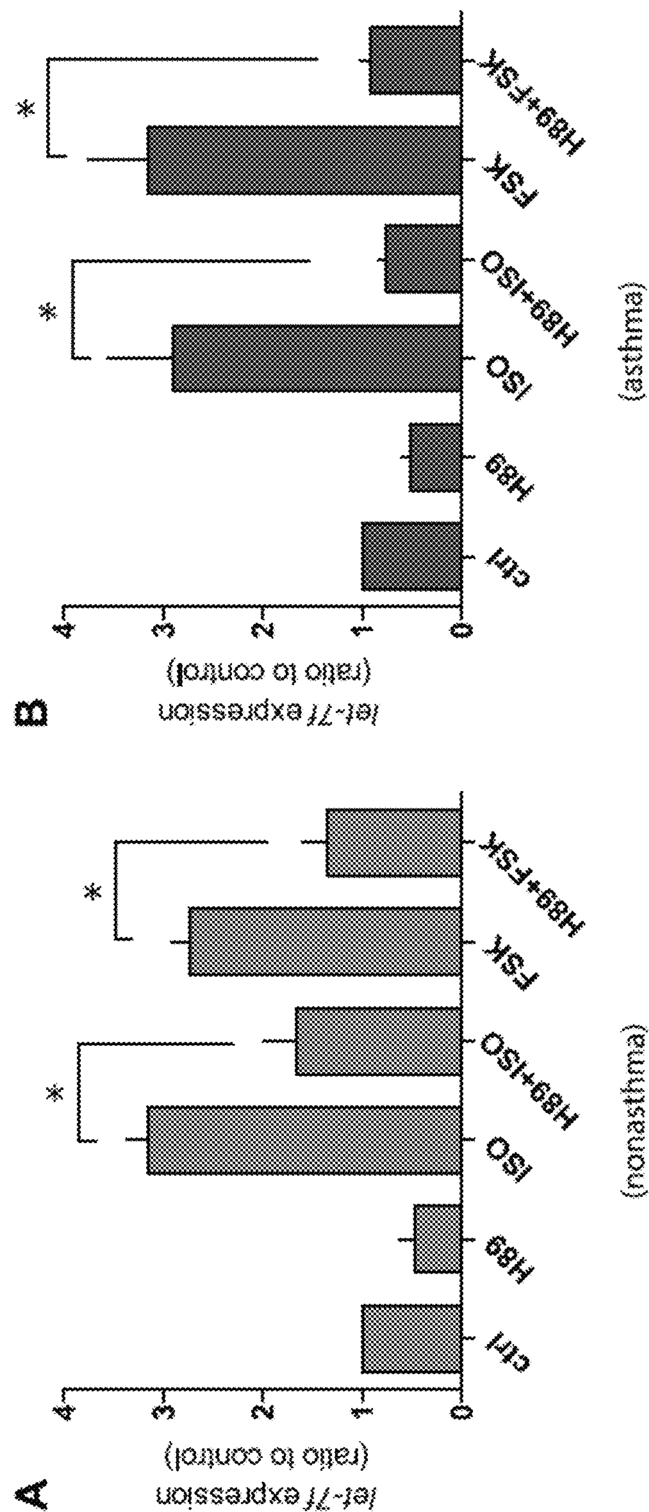
FIGS. 2A-2D show graphs that can demonstrate cAMP/PKA-dependent agonist regulation of let-7f in HASM cells.
Figures 2C, 2D:
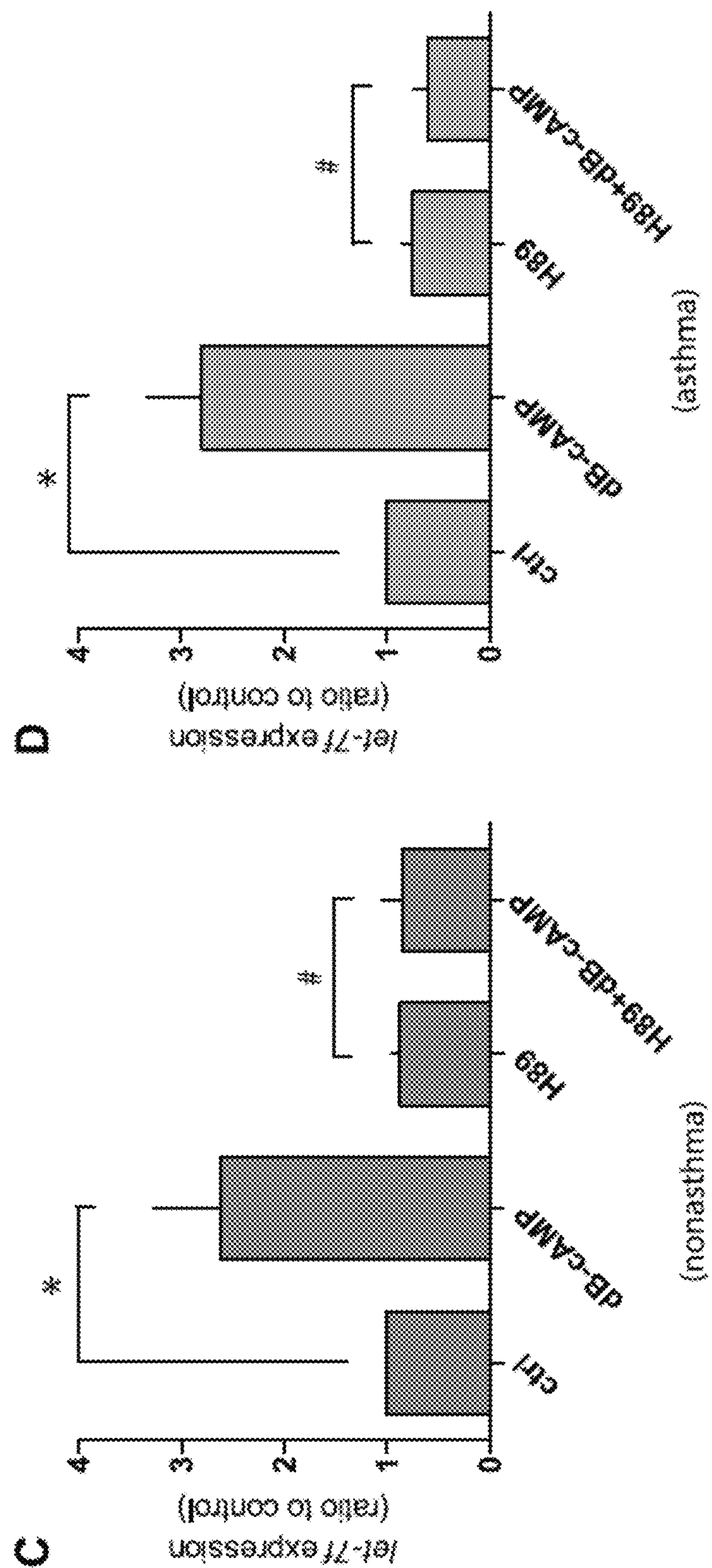

Having established a link between let-7f increases from β-agonist exposure and agonist-promoted downregulation of 2AR, studies were undertaken to ascertain the mechanism by which let-7f is increased by agonists. It was considered that the increase in let-7f might be dependent on activation of PKA, which is promoted by $\beta_2$AR stimulation of intracellular cAMP. To address this, cells were treated with the diterpene forskolin, thus activating adenylyl cyclase and increasing cAMP in a receptor-independent fashion. The dose of forskolin was equieffective in stimulating cAMP as ISO (data not shown). To separate a PKA-dependent mechanism from a non-PKA event evoked by cAMP, the PKA inhibitor H89 was also utilized. As shown in FIGS. 2A-2B, forskolin increased let-7f to a similar extent as ISO in non-asthmatic and asthmatic HASM cells. Both responses were inhibited by H89. Additional studies were also performed using the cell-permeable cAMP analog dibutyryl-cAMP, to further confirm the dependency on cAMP. The expression of let-7f increased after an 18 h treatment with dibutyryl-cAMP, which was blocked by H89 (FIGS. 2C to 2D).

Figures 3A, 3B:
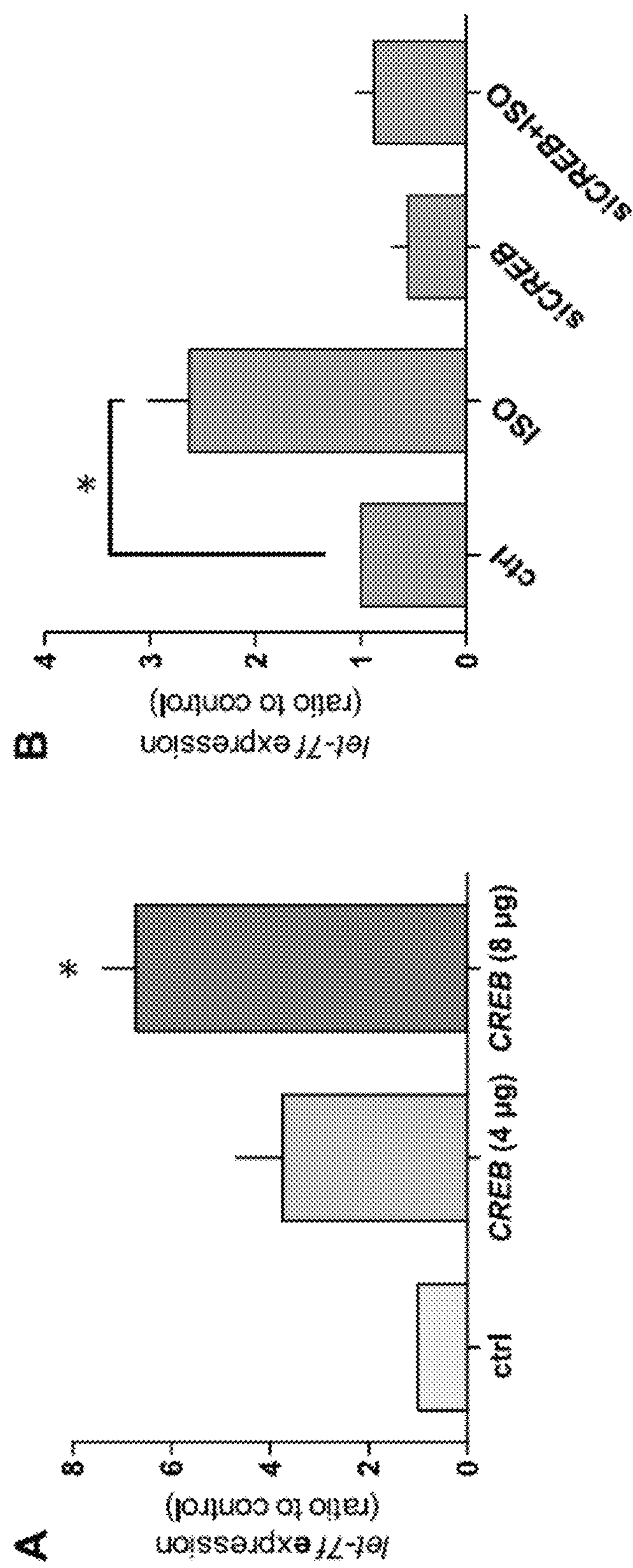
FIGS. 3A-3D show graphs that can demonstrate that CREB modulates let-7f expression and long-term agonist-promoted down-regulation of $\beta_2$AR in HASM cells.

These results indicated that a PKA-mediated event promotes the increase in let-7f observed with chronic β-agonist exposure. It was hypothesized that the mechanism of this response could be due to activation of CREB, which then binds to a putative binding site in the promoter of let-7f. Initial studies of CREB overexpression in HASM cells (in the absence of an agonist) were performed, which showed an increase of let-7f in a gene-dose-dependent fashion (FIG. 3A). A moderate degree of native CREB expression was found in HASM cells, so the CREB was silenced using siRNA, and then the primary phenotype of β-agonist-induced increase in let-7f expression was examined.

Figure 4A:
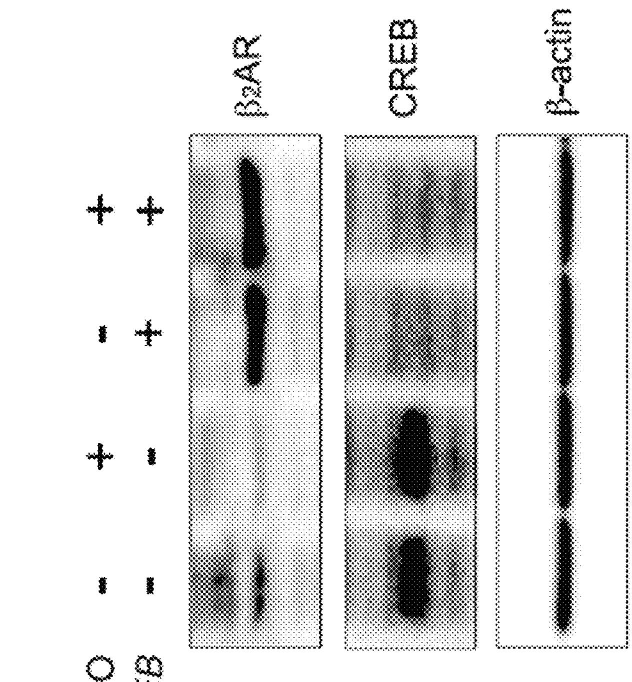
FIGS. 4A-4B can demonstrate localization of CREB binding sites in the let-7f pri-miRNA promoter.
Figure 4B:
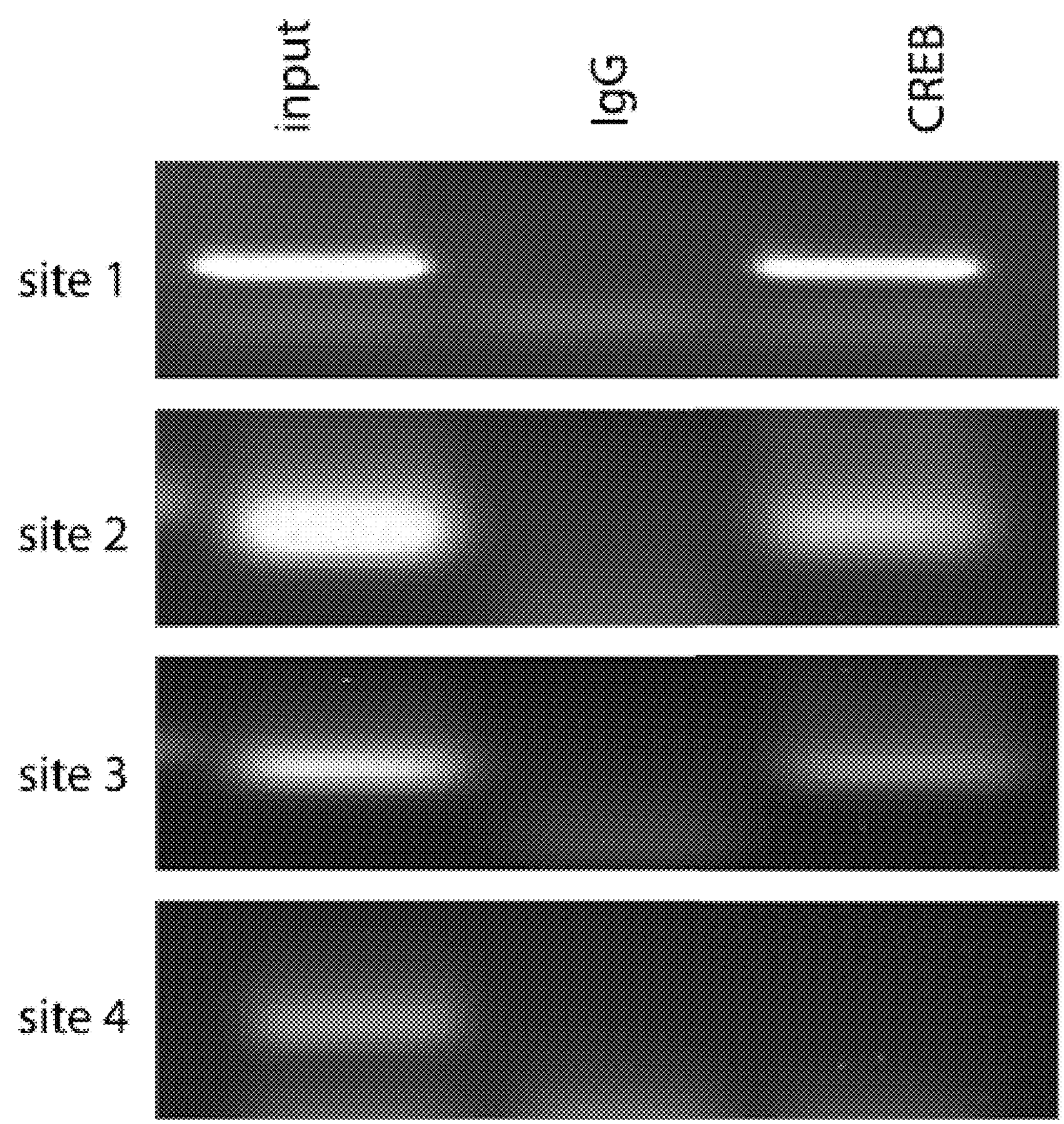

As shown in FIG. 3B, siCREB reduced the baseline expression of let-7f. More importantly, 18 h ISO exposure in siCREB-transfected cells caused no increase in let-7f, in contrast to nontransfected control cells studied in parallel (FIG. 3B). Taken together, the data indicated a PKA-mediated, CREB-based regulation of let-7f expression. Using the program JASPAR, 4 potential CREB sites in the promoter of the let-7f pri-miRNA sequence, as found in human chromosome 9q 22.2-31.1 sequence (GenBank) were found. (The pri-miRNA is initially transcribed and subsequently cleaved to the 22 bp let-7f miRNA). These potential CREB sites are arbitrarily defined as sites 1, 2, 3, and 4 (FIG. 4A). The binding scores for the 4 sites were 6.51, 6.36, 7.86, and 6.9, respectively. PCR primers were established to amplify each potential site after chromatin immunoprecipitation (see Materials and Methods section in this Example). Sheared DNA protein complexes from HASM cells were immunoprecipitated with a CREB antibody, and the subsequent DNA was subjected to site-specific PCR. As shown in FIG. 4B, PCRs for predicted sites 1, 2, and 3 in the let-7f promoter were amplified, which indicates binding of these regions to CREB. Site 4 was not amplified, indicating that CREB did not bind to this region. When IgG was utilized instead of the CREB antibody, no specific PCR products were detected. PCR with the input DNA (prior to immunoprecipitation) revealed products of the expected molecular size, indicating the validity of the primers.

Figures 3C, 3D:
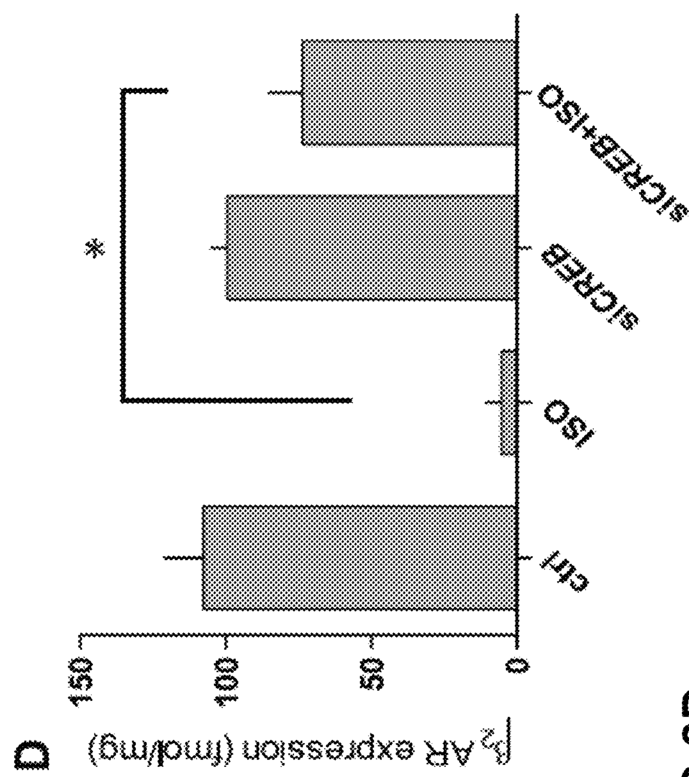

PKA activation evoked by β-agonists was considered to cause CREB phosphorylation, leading to its binding to the CREs in the promoter of let-7f. This binding increases let-7f and leads to translational repression of ADRB2, and a subsequent decrease in $\beta_2$AR protein expression. This was tested by knocking down CREB in HASM cells in the absence and presence of long-term ISO exposure, and measuring $\beta_2$AR expression. A representative experiment wherein $\beta_2$AR expression was ascertained by Western blot is shown in FIG. 3C. The top panel shows the downregulation of $\beta_2$AR by agonists in control cells and that this effect is not observed when CREB is silenced. FIG. 3D shows the results of multiple experiments in which $\beta_2$AR expression was quantitatively determined through radioligand binding. Under control conditions, ISO treatment resulted in a significant decrease in $\beta_2$AR expression (>90%). With CREB knockdown, down-regulation by ISO was only about 20% (FIG. 3D), indicating that this CREB-let-7f mechanism is a significant component of agonist-promoted down-regulation in HASM cells. The magnitude of this effect on $\beta_2$AR down-regulation observed in the CREB knock down experiments is remarkably similar to that observed when let-7f is ablated (compare FIGS. 3D and 1D), consistent with the serial nature of the pathway identified.

Discussion

The mechanisms at play in the regulation of $\beta_2$AR function during continuous agonist exposure have been relatively well-established for short-term exposure, but there are multiple gaps in our understanding of events responsible for long-term agonist regulation. There has been a general assumption that the early events dictate or are a prerequisite for down-regulation, which has led to the belief that the early and late events represent a simple continuum. Applying this linear paradigm suggests that the dominant mechanism in long-term regulation is agonist promoted phosphorylation by GRKs, which promote β-arrestin binding (early events) leading to ongoing receptor internalization and ultimate degradation of internalized receptors (late events), resulting in a net reduction in $\beta_2$AR expression (down-regulation).

Several lines of evidence, however, do not support this as the singular mechanism. For example, studies have shown that, with impaired short-term desensitization, mutated $\beta_2$AR s lacking all potential serine or threonine GRK phosphorylation sites nevertheless display long-term down-regulation similar to that of wild-type receptors (34). In other studies, mutations of the $\beta_2$AR that alter the agonist bound "active" state (equivalent to the GRK-phosphorylated and β-arrestin-bound state) have no effect on agonist mediated internalization (35). Similarly, others have observed that mutants with wild-type agonist-promoted phosphorylation and internalization exhibit impaired long term down-regulation, again showing a separation between these processes and suggesting additional mechanisms (35). Furthermore, some agonists that cause similar degrees of GRK-mediated phosphorylation of wild-type $\beta_2$ARs display markedly different degrees of down-regulation (36). Of particular interest is the observation that $\beta_2$AR down-regulation can be evoked to nearly the same extent as that induced by β-agonists through incubating cells with dibutyryl-cAMP and forskolin, pointing to cAMP-dependent events that lead to decreased receptor expression (37).

The intronless human ADRB2 gene does not have a CRE in the 5'-region including the promoter, so feedback at this level due to a cAMP/PKA mechanism is not expected. It was postulated, however, that a CREB dependent mechanism evoked by receptor activation, cAMP generation, and PKA activation might downregulate another gene whose product participates in $\beta_2$AR down-regulation. It has been previously shown that there is a 100% match between the seed region for the miRNA let-7f and a 3' UTR sequence of the ADRB2 (19).

Using a reporter system with human embryonic kidney 293 cells, transfected wild-type let-7f inhibited translation of the reporter linked to wild-type ADRB2 3' UTR. In contrast, mutation of the ADRB2 sequence within the predicted binding site, or mutation of let-7f in the seed region, resulted in no change in reporter expression (19). These results prompted studies of endogenous expression of $\beta_2$ARs in H292 cells (an epithelial carcinoma cell line). As has been previously established (38, 39), the guide miRNA strand is assembled into the miRNA-induced silencing complex (miRISC) while the passenger strand is degraded. A core component of miRISC is Ago2, a member of the Argonaute endonucleases, which binds to the guide miRNA strand and silences translation of the targeted mRNA. Overexpression of let-7f was found to increase in ADRB2 mRNA immunoprecipated with Ago2, thus confirming that let-7f binds to ADRB2 and functional interaction with the silencing mechanism occurs (19).

Furthermore, there was a correlation between $\beta_2$AR protein expression and let-7f expression. So, these studies revealed that let-7f regulates $\beta_2$AR expression, but its potential role in $\beta_2$AR down-regulation by agonist in HASM cells, or the mechanism of such a potential effect, was not defined.

In this Example, it is shown in HASM cells that let-7f expression increases with chronic β-agonist exposure, and, greater increases in let-7f are associated with greater degrees of down-regulation. Furthermore, agonist promoted down-regulation was attenuated in HASM cells by about 50% when let-7f was silenced, indicating a nontrivial role of this mechanism in the down-regulation process. Multiple approaches showed that the agonist promoted increase in let-7f was cAMP and PKA dependent, indicating that let-7f was the intermediate component in a negative feedback loop. Informatic analysis revealed 4 potential CRE sequences in the 5' promoter of let-7f, and chromatin immunoprecipitation studies in HASM cells showed that 3 of these sites bind CREB. When CREB was silenced, agonist-promoted down-regulation was attenuated by about 50%, an effect with a magnitude similar to that observed when let-7f was silenced.

Figure 5:
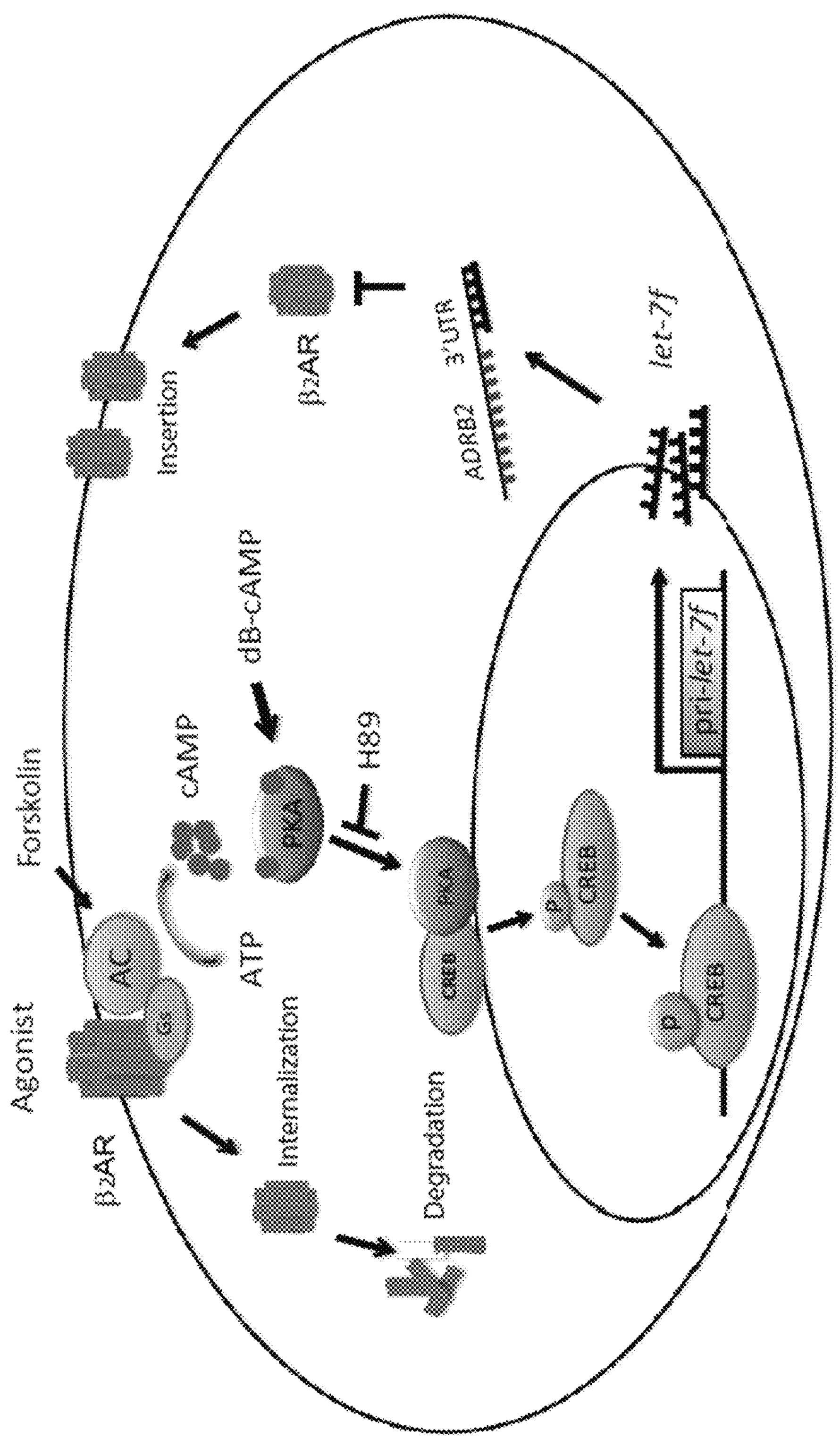
FIG. 5 shows a schematic that can demonstrate a summary of the mechanisms responsible for $\beta_2$AR down-regulation by CREB-mediated/let-7f processes in HASM cells. HASM cells express 2AR at a stable level when receptor production and degradation are at an equilibrium. Upon agonist activation of $\beta_2$AR, intracellular cAMP levels increase due to receptor-Gs coupling. cAMP activates PKA, which in turn activates the CREB transcription factor. The transcription factor subsequently binds to the promoter of pri-let-7f, increasing expression of let-7f. Then let-7f binds to the 3' UTR of ADRB2 and represses translation, contributing to agonist-promoted long-term down-regulation of $\beta_2$AR. Another mechanism of down-regulation that is apparent in HASM cells is the degradation of β-arrestin-mediated internalized receptors.

Thus, in HASM cells a mechanism has been delineated that accounts for about 50% of the magnitude of the long-term agonist-promoted down-regulation response (summarized in FIG. 5). This mechanism is due to a cAMP dependent transcriptional regulation of let-7f by CREB, which represses translation of $\beta_2$AR. The other components of down-regulation include the degradation of internalized receptors (40), and potentially other mechanisms. The HASM cell type is of particular interest because chronic β-agonists, acting on $\beta_2$ARs on smooth muscle cells of the airway, are utilized for the treatment of airflow obstruction in asthma and COPD. Long-term treatment with β-agonists is not uncommon, and is utilized for maintenance or preventative treatment in chronic asthma and COPD. And, as indicated in the Introduction section of this Example, there are multiple adverse effects with chronic β-agonist exposure. Many of these, such as a decrease in bronchodilation, a decrease insensitivity to acute β-agonists, and loss of the bronchoprotective effects of acute β-agonists against inhaled constrictive agents, are consistent with depressed airway smooth muscle $\beta_2$AR function evoked by prolonged $\beta_2$AR activation. Furthermore, the corollary to these physiologic measurements may be adverse clinical outcomes, such as increased exacerbations and hospitalizations. This let-7f-mediated down-regulation of $\beta_2$ARs occurs regardless of how cAMP levels are increased, as indicated by the fact that 2AR activation, a cAMP analog, and activation of adenylyl cyclase with forskolin, all evoke the response. Thus, any potential new bronchodilator that acts via binding to a Gs-coupled receptor (41), would ultimately lead to $\beta_2$AR down-regulation. This event would be deleterious for asthma therapy, as b-agonist responsiveness would be reduced, leaving less "b-agonist reserve" for acute treatment of severe bronchospasm. Bronchodilators acting via completely different mechanisms, such as agonists for bitter taste receptors, which relax HASM cells via a non-cAMP-dependent mechanism, have been proposed for add-on (or replacement) therapy to b-agonists, in part because of this lack of crosstalk (42). Interestingly, the upregulation of let-7f by b-agonists may be cell-type dependent.

A small decrease in let-7f from whole lung homogenates from mice chronically treated with β-agonists has been observed (19). However, the lung consists of about 40 cell types, of which many express $\beta_2$ARs. Indeed, in whole lung homogenates the great majority of $\beta_2$ARs come from type II cells of the alveoli (43). The physiologic role of $\beta_2$ARs in these cells is not well established, and they are not utilized as therapeutic targets, so while this response is intriguing, its relevance is unclear. Nevertheless, these results suggest the potential for cell type specificity in the let-7f mediated regulation of $\beta_2$AR down-regulation. In addition, the relative contribution of cAMP-dependent vs. agonist-dependent down-regulation of $\beta_2$ARs appears to differ based on cell type or experimental conditions. For example, stably transfected human embryonic kidney 293 cells greatly overexpressing $\beta_2$ARs have been reported to have a relatively small degree of dibutyryl cAMP-mediated down-regulation of $\beta_2$ARs compared with that of ISO (40). This may be due to cell type characteristics, the expression vector, or the marked overexpression. In contrast, a cAMP-mediated pathway predominates in Chinese hamster fibroblast 1102 cells transfected to express $\beta_2$ARs (37). This Example exclusively utilized HASM cells that endogenously express $\beta_2$AR, so artifacts from overexpression are avoided. Regardless, the characteristics of the down-regulation phenotype in these cells is relevant, since $\beta_2$ARs in HASM cells have a well-recognized physiologic role and are targets for β-agonists in the treatment of obstructive lung disease.

In summary, a previously undescribed mechanism that is responsible for at least 50% of the agonist-promoted down-regulation of $\beta_2$ARs has been identified (FIG. 5). This mechanism is instigated by a $\beta_2$AR-mediated increase in intracellular cAMP, which activates PKA, and PKA in turn activates CREB. CREB then binds to several CREs in the promoter of the miRNA let-7f. This causes increased cellular expression of let-7f, which then binds to the 3' UTR of ADRB2 and represses ADRB2 translation, leading to a progressive loss of 2AR protein expression. This pathway was established in the pharmacologically relevant HASM cell, where $\beta_2$ARs act as targets for β-agonist treatment to relieve airway obstruction in asthma. These events were also observed in HASM cells derived from donor lungs of asthmatics, indicating that this regulatory pathway is intact in a pathophysiologic model. Given that the adverse effects of prolonged β-agonist treatment can be attributed to 2AR down-regulation, adjunct therapy aimed at blocking this pathway may prove clinically useful.

REFERENCES FOR EXAMPLE 1

1. Liggett, S. B. (1991) Desensitization of the b-adrenergic receptor: distinct molecular determinants of phosphorylation by specific kinases. Pharmacol. Res. 24(Suppl 1), 29-41
2. Kohout, T. A., and Lefkowitz, R. J. (2003) Regulation of G protein-coupled receptor kinases and arrestins during receptor desensitization. Mol. Pharmacol. 63, 9-18
3. Lohse, M. J., Engelhardt, S., and Eschenhagen, T. (2003) What is the role of b-adrenergic signaling in heart failure? Circ. Res. 93, 896-906
4. Liggett, S. B. (2011) Phosphorylation barcoding as a mechanism of directing GPCR signaling. Sci. Signal. 4, pe36
5. Hanyaloglu, A. C., and von Zastrow, M. (2008) Regulation of GPCRs by endocytic membrane trafficking and its potential implications. Annu. Rev. Pharmacol. Toxicol. 48, 537-568
6. Lefkowitz, R. J. (2013) Arrestins come of age: a personal historical perspective. In Progress in Molecular Biology and Translational Science, Vol. 118 (Ed. Luttrell, L. M.), pp. 3-18, Academic Press, New York
7. Lipworth, B. J. (1997) Airway subsensitivity with long-acting β2-agonists. Is there cause for concern? Drug Saf. 16, 295-308
8. Newnham, D. M., Grove, A., McDevitt, D. G., and Lipworth, B. J. (1995) Subsensitivity of bronchodilator and systemic beta 2 adrenoceptor responses after regular twice daily treatment with eformoterol dry powder in asthmatic patients. Thorax 50, 497-504
9. Kalra, S., Swystun, V. A., Bhagat, R., and Cockcroft, D. W. (1996) Inhaled corticosteroids do not prevent the development of tolerance to the bronchoprotective effect of salmeterol. Chest 109, 953-956
10. Harvey, J. E., and Tattersfield, A. E. (1982) Airway response to salbutamol: effect of regular salbutamol inhalations in normal, atopic, and asthmatic subjects. Thorax 37, 280-287
11. Bhagat, R., Kalra, S., Swystun, V. A., and Cockcroft, D. W. (1995) Rapid onset of tolerance to the bronchoprotective effect of salmeterol. Chest 108, 1235-1239
12. Grove, A., and Lipworth, B. J. (1995) Bronchodilator subsensitivity to salbutamol after twice daily salmeterol in asthmatic patients. Lancet 346, 201-206
13. Booth, H., Bish, R., Walters, J., Whitehead, F., and Walters, E. H. (1996) Salmeterol tachyphylaxis in steroid treated asthmatic subjects. Thorax 51, 1100-1104
14. Israel, E., Chinchilli, V. M., Ford, J. G., Boushey, H. A., Cherniack, R., Craig, T. J., Deykin, A., Fagan, J. K., Fahy, J. V., Fish, J., Kraft, M., Kunselman, S. J., Lazarus, S. C., Lemanske, R. F., Jr., Liggett, S. B., Martin, R. J., Mitra, N., Peters, S. P., Silverman, E., Sorkness, C. A., Szefler, S. J., Wechsler, M. E., Weiss, S. T., and Drazen, J. M.; National Heart, Lung, and Blood Institute's Asthma Clinical Research Network. (2004) Use of regularly scheduled albuterol treatment in asthma: genotype-stratified, randomised, placebo-controlled crossover trial. Lancet 364, 1505-1512

15. Salpeter, S. R., Buckley, N. S., Ormiston, T. M., and Salpeter, E. E. (2006) Meta-analysis: effect of long-acting β-agonists on severe asthma exacerbations and asthma-related deaths. Ann. Intern. Med. 144, 904-912
16. Sears, M. R. (1998) Role of β2-agonists in asthma fatalities. In Fatal Asthma (Sheffer, A. L., ed.), pp. 457-481, Vol. 115, Marcel Dekker, New York
17. Nelson, H. S., Weiss, S. T., Bleecker, E. R., Yancey, S. W., and Dorinsky, P. M.; SMART Study Group. (2006) The salmeterol multicenter asthma research trial: a comparison of usual pharmacotherapy for asthma or usual pharmacotherapy plus salmeterol. Chest 129, 15-26
18. Grainger, J., Woodman, K., Pearce, N., Crane, J., Burgess, C., Keane, A., and Beasley, R. (1991) Prescribed fenoterol and death from asthma in New Zealand, 1981-7: a further case-control study. Thorax 46, 105-111
19. Wang, W. C. H., Juan, A. H., Panebra, A., and Liggett, S. B. (2011) MicroRNAlet-7 establishes expression of β2-adrenergic receptors and dynamically down-regulates agonist-promoted down-regulation. Proc. Natl. Acad. Sci. USA 108, 6246-6251
20. Deshpande, D. A., Wang, W. C. H., McIlmoyle, E. L., Robinett, K. S., Schillinger, R. M., An, S. S., Sham, J. S. K., and Liggett, S. B. (2010) Bitter taste receptors on airway smooth muscle bronchodilate by localized calcium signaling and reverse obstruction. Nat. Med. 16, 1299-1304
21. Aisenberg, W. H., Huang, J., Zhu, W., Rajkumar, P., Cruz, R., Santhanam, L., Natarajan, N., Yong, H. M., De Santiago, B., Oh, J. J., Yoon, A.-R., Panettieri, R. A., Homann, O., Sullivan, J. K., Liggett, S. B., Pluznick, J. L., and An, S. S. (2016) Defining an olfactory receptor function in airway smooth muscle cells. Sci. Rep. 6, 38231
22. Kim, D., Woo, J. A., Geffken, E., An, S. S., and Liggett, S. B. (2017) Coupling of airway smooth muscle bitter taste receptors to intracellular signaling and relaxation is via Gai1,2,3. Am. J. Respir. Cell Mol. Biol. 56, 762-771
23. Kim, D., Pauer, S. H., Yong, H. M., An, S. S., and Liggett, S. B. (2016) β2-adrenergic receptors chaperone trapped bitter taste receptor 14 to the cell surface as a heterodimer and exert unidirectional desensitization of taste receptor function. J. Biol. Chem. 291, 17616-17628
24. Xue, H., Gao, X., Xu, S., Zhang, J., Guo, X., Yan, S., Li, T., Guo, X., Liu, Q., and Li, G. (2016) MicroRNA-Let-7f reduces the vasculogenic mimicry of human glioma cells by regulating periostin-dependent migration. Oncol. Rep. 35, 1771-1777
25. Barnes, N. A., Stephenson, S., Cocco, M., Tooze, R. M., and Doody, G. M. (2012) BLIMP-1 and STAT3 counter regulate microRNA-21 during plasma cell differentiation. J. Immunol. 189, 253-260
26. Panebra, A., Wang, W. C., Malone, M. M., Pitter, D. R. G., Weiss, S. T., Hawkins, G. A., and Liggett, S. B. (2010) Common ADRB2 haplotypes derived from 26 polymorphic sites direct β2-adrenergic receptor expression and regulation phenotypes. PLoS One 5, e11819
27. Panebra, A., Schwarb, M. R., Swift, S. M., Weiss, S. T., Bleecker, E. R., Hawkins, G. A., and Liggett, S. B. (2008) Variable-length poly-C tract polymorphisms of the β2-adrenergic receptor 3'-UTR alter expression and agonist regulation. Am. J. Physiol. Lung Cell. Mol. Physiol. 294, L190-L195
28. Schmittgen, T. D., and Livak, K. J. (2008) Analyzing real-time PCR data by the comparative CT method. Nat. Protoc. 3, 1101-1108
29. Livak, K. J., and Schmittgen, T. D. (2001) Analysis of relative gene expression data using real-time quantitative PCR and the $2^{-\Delta\Delta CT}$ method. Methods 25, 402-408
30. Qiu, Z., Dyer, K. D., Xie, Z., Radinger, M., and Rosenberg, H. F. (2009) GATA transcription factors regulate the expression of the human eosinophil-derived neurotoxin (RNase 2) gene. J. Biol. Chem. 284, 13099-13109
31. Mialet Perez, J., Rathz, D. A., Petrashevskaya, N. N., Hahn, H. S., Wagoner, L. E., Schwartz, A., Dorn G. W. II, and Liggett, S. B. (2003) β1-adrenergic receptor polymorphisms confer differential function and predisposition to heart failure. Nat. Med. 9, 1300-1305
32. Sandelin, A., Alkema, W., Engstr¨om, P., Wasserman, W. W., and Lenhard, B. (2004) JASPAR: an open-access database for eukaryotic transcription factor binding profiles. Nucleic Acids Res. 32(Suppl 1), D91-D94
33. An, S. S., Mitzner, W., Tang, W.-Y., Ahn, K., Yoon, A.-R., Huang, J., Kilic, O., Yong, H. M., Fahey, J. W., Kumar, S., Biswal, S., Holgate, S. T., Panettieri, R. A., Jr., Solway, J., and Liggett, S. B. (2016) An inflammation-independent contraction mechanophenotype of airway smooth muscle in asthma. J. Allergy Clin. Immunol. 138, 294-297.e4
34. Liggett, S. B., Bouvier, M., Hausdorff, W. P., O'Dowd, B., Caron, M. G., and Lefkowitz, R. J. (1989) Altered patterns of agonist-stimulated cAMP accumulation in cells expressing mutant beta 2-adrenergic receptors lacking phosphorylation sites. Mol. Pharmacol. 36, 641-646
35. Campbell, P. T., Hnatowich, M., O'Dowd, B. F., Caron, M. G., Lefkowitz, R. J., and Hausdorff, W. P. (1991) Mutations of the human beta 2-adrenergic receptor that impair coupling to Gs interfere with receptor down-regulation but not sequestration. Mol. Pharmacol. 39, 192-198
36. Swift, S. M., Schwarb, M. R., Mihlbachler, K. A., and Liggett, S. B. (2007) Pleiotropic b-agonist-promoted receptor conformations and signals independent of intrinsic activity. Am. J. Respir. Cell Mol. Biol. 36, 236-243
37. Bouvier, M., Collins, S., O'Dowd, B. F., Campbell, P. T., de Blasi, A., Kobilka, B. K., MacGregor, C., Irons, G. P., Caron, M. G., and Lefkowitz, R. J. (1989) Two distinct pathways for cAMP-mediated down-regulation of the β2-adrenergic receptor: phosphorylation of the receptor and regulation of its mRNA level. J. Biol. Chem. 264, 16786-16792
38. Han, J., Lee, Y., Yeom, K.-H., Kim, Y.-K., Jin, H., and Kim, V. N. (2004) The Drosha-DGCR8 complex in primary micro RNA processing. Genes Dev. 18, 3016-3027
39. Chendrimada, T. P., Gregory, R. I., Kumaraswamy, E., Norman, J., Cooch, N., Nishikura, K., and Shiekhattar, R. (2005) TRBP recruits the Dicer complex to Ago2 for microRNA processing and gene silencing. Nature 436, 740-744
40. Moore, R. H., Tuffaha, A., Millman, E. E., Dai, W., Hall, H. S., Dickey, B. F., and Knoll, B. J. (1999) Agonist-induced sorting of human beta2-adrenergic receptors to lysosomes during downregulation. J. Cell Sci. 112, 329-338
41. Mizuta, K., Zhang, Y., Xu, D., Mizuta, F., D'Ovidio, F., Masaki, E., and Emala, C. W. (2013) The dopamine D1 receptor is expressed and facilitates relaxation in airway smooth muscle. Respir. Res. 14, 89
42. Liggett, S. B. (2013) Bitter taste receptors on airway smooth muscle as targets for novel bronchodilators. Expert Opin. Ther. Targets 17, 721-731
43. McGraw, D. W., Fukuda, N., James, P. F., Forbes, S. L., Woo, A. L., Lingrel, J. B., Witte, D. P., Matthay, M. A., and Liggett, S. B. (2001) Targeted transgenic expression of β2-adrenergic receptors to type II cells increases alveolar fluid clearance. Am. J. Physiol. Lung Cell. Mol. Physiol. 281, L895-L903

I claim:

1. A method of reducing β-agonist-mediated $\beta_2$-Adrenergic Receptor ($\beta_2$AR) down regulation in a subject in need thereof, the method comprising:

reducing the amount of let-7f miRNA in a cell of the subject in need thereof that expresses $\beta_2$AR and that has been exposed to a β-agonist, wherein the step of reducing the amount of let-7f miRNA comprises administering an amount of a let-7f miRNA inhibitor to the subject in need thereof, wherein the let-7f miRNA inhibitor is a single stranded let-7f miRNA gene silencing oligonucleotide.

2. The method of claim 1, wherein the single stranded let-7f miRNA gene silencing oligonucleotide comprises the nucleic acid sequence SEQ ID NO: 11.

3. The method of claim 1, wherein the cell is an airway cell.

4. The method of claim 1, wherein the subject in need thereof has an airway disease.

5. A method of treating an asthma or chronic obstructive pulmonary disease (COPD) in a subject in need thereof, the method comprising:

administering a beta-agonist to the subject in need thereof; and administering an amount of an let-7f miRNA inhibitor effective to reduce the amount of let-7f miRNA in an airway cell that expresses $\beta_2$AR, wherein the let-7f miRNA inhibitor is a single stranded let-7f miRNA gene silencing oligonucleotide.

6. The method of claim 5, wherein the single stranded let-7f miRNA gene silencing oligonucleotide comprises the nucleic acid sequence SEQ ID NO: 11.

7. The method of claim 5, wherein the beta-agonist is selected from the group consisting of: albuterol and pharmaceutically acceptable salts thereof, levalbuterol and pharmaceutically acceptable salts thereof, metaproterenol and pharmaceutically acceptable salts thereof, salmeterol and pharmaceutically acceptable salts thereof, fomoterol and pharmaceutically acceptable salts thereof, afromoterol and pharmaceutically acceptable salts thereof, olodaterol and pharmaceutically acceptable salts thereof, vilanterol and pharmaceutically acceptable salts thereof, fenoterol and pharmaceutically acceptable salts thereof, epinephrine and pharmaceutically acceptable salts thereof, and combinations thereof.

8. The method of claim 5, wherein the airway cell is a smooth muscle airway cell.

* * * * *